United States Patent [19]
Ulevitch et al.

[11] Patent Number: 5,871,937
[45] Date of Patent: Feb. 16, 1999

[54] ACUTE PHASE PROTEIN MODULATING ENDOTOXIC ACTIVITY OF LIPOPOLYSACCHARIDES, ASSAY METHODS AND POLYPEPTIDES

[75] Inventors: Richard J. Ulevitch, Del Mar; Peter S. Tobias, Encinitas, both of Calif.

[73] Assignee: The Scripps Research Institute, La Jolla, Calif.

[21] Appl. No.: 990,849

[22] Filed: Dec. 15, 1997

Related U.S. Application Data

[62] Division of Ser. No. 240,328, May 10, 1994, Pat. No. 5,698,680, which is a division of Ser. No. 847,562, Mar. 2, 1992, Pat. No. 5,310,879, which is a continuation-in-part of Ser. No. 367,454, Jun. 16, 1989, Pat. No. 5,245,013, which is a continuation-in-part of Ser. No. 6,710, Dec. 30, 1986, abandoned, which is a continuation-in-part of Ser. No. 728,833, Apr. 30, 1985, abandoned.

[51] Int. Cl.$^6$ ............ G01N 33/53; G01N 33/52
[52] U.S. Cl. .......... 435/7.1; 435/7.32; 435/7.92; 424/1.49; 424/1.69; 424/9.1; 424/9.322
[58] Field of Search ............ 435/7.1, 7.32, 435/7.92; 424/1.49, 1.69, 9.1, 9.322

[56] References Cited

U.S. PATENT DOCUMENTS

| | | | |
|---|---|---|---|
| 5,245,013 | 9/1993 | Ulevitch et al. | 530/380 |
| 5,310,879 | 5/1994 | Ulevitch et al. | |
| 5,698,680 | 12/1997 | Ulevitch et al. | 530/388.25 |

OTHER PUBLICATIONS

Goding et al., Monoclonal Antibodies: Principles and Practice, pp. 70–77.
Tobias et al., J. Exp. Med., 164:777, 1986.

*Primary Examiner*—Frank C. Eisenschenk
*Attorney, Agent, or Firm*—Fish & Richardson P.C.

[57] ABSTRACT

A lipopolysaccharide binding protein is disclosed as are an assay method, polypeptides and antibodies related to that binding protein. The binding protein: (a) is present in impure form in acute phase serum, but is substantially absent from normal serum; (b) binds to Gram-negative bacterially secreted lipopolysaccharide in vitro in the serum of the animal treated; (c) retards in vitro binding of the lipopolysaccharide to high density lipoprotein present in the normal serum of the animal host; and (d) immunoreacts with antibodies raised to a polypeptide having the amino acid residue sequence, from left to right and in the direction from amino-terminus to carboxy-terminus, or Thr—Asn—Pro—Gly—Leu—Ile—Thr—Arg—Ile—Thr—
Asp—Lys—Gly—Leu—Glu—Tyr—Ala—Ala—Arg—Glu—
Gly—Leu—Leu—Ala—Leu—Gln—Arg—Lys—Leu—Asn(Leu)—
Gly—Val—Thr—Leu—Pro—Asp—Phe(Ser)—Asp—Gly;

wherein each of said parenthesized amino acid residues is an alternative to the immediately preceding residue in said sequence.

13 Claims, 18 Drawing Sheets

FIG. 17

```
  1  MGTWARALLG STLVSLLLAA APGALGTNPG LITRITDKGL EYAAREGLLA
 51  LQRKLLEVTL PDSDGDFRIK HFGRAQYKFY SLKIPRFELL RGTLRPLPGQ
101  GLSLDISDAY IHVRGSWKVR KAFLRLKNSF DLYVKGLTIS VHLVLGSESS
151  GRPTVTTSSC SSDIQNVELD IEGDLEELLN LLQSQIDARL REVLESKICR
201  QIEEAVTAHL QPYLQTLPVT TQIDSFAGID YSLMEAPRAT AGMLDVMFKG
251  EIFPLDHRSP VDFLAPAMNL PEAHSRMVYF SISDYVFNTA SLAYHKSGYW
301  NFSITDAMVP ADLNIRRTTK SFRPFVPLLA NLYPNMNLEL QGTVNSEQLV
351  NLSTENLLEE PEMDIEALVV LPSSAREPVF RLGVATNVSA TLTLNTRKIT
401  GFLKPGRLQV ELKESKVGGF NVELLEALLN YYILNNLYPK VNEKLAHRFP
451  LPLLRHIQLY DLLLQTHENF LLVGANIQYR RV
```

FIG. 19

```
  1  MGALARALPS ILLALLLTST PEALGANPGL VARITDKGLQ YAAQEGLLAL
 51  QSELLRITLP DFTGDLRIPH VGRGRYEFHS LNIHSCELLH SALRPVPGQG
101  LSLSISDSSI RVQGRWKVRK SFFKLQGSFD VSVKGISISV NLLLGSESSG
151  RPTGYCLSCS SDIADVEVDM SGDSGWLLNL FHNQIESKFQ KVLESRICEM
201  IQKSVSSDLQ PYLQTLPVTT EIDSFADIDY SLVEAPRATA QMLEVMFKGE
251  IFHRNHRSPV TLLAAVMSLP EEHNKMVYFA ISDYVFNTAS LVYHEEGYLN
301  FSITDDMIPP DSNIRLTTKS FRPFVPRLAR LYPNMNLELQ GSVPSAPLLN
351  FSPGNLSVDP YMEIDAFVLL PSSSKEPVFR LSVATNVSAT LTFNTSKITG
401  FLKPGKVKVE LKESKVGLFN AELLEALLNY YILNTLYPKF NDKLAEGFPL
451  PLLKRVQLYD LGLQIHKDFL FLGANVQYMR V*
```

FIG. 18

```
   1 ATGGGGACCT GGGCCAGGGC CCTGCTGGGG TCCACCCTGG TGAGCCTGCT
  51 GCTCGCAGCT GCCCCGGGAG CTCTGGGCAC CAACCCCGGC CTCATCACCA
 101 GGATCACCGA CAAAGGCCTG GAGTACGCGG CCAGGGAGGG GCTGCTGGCT
 151 CTGCAGAGAA AGCTCCTGGA AGTCACGCTG CCGGATTCCG ATGGGGACTT
 201 CAGGATCAAA CATTTCGGGC GTGCACAGTA CAAGTTCTAC AGTCTGAAAA
 251 TCCCCAGATT CGAGCTGCTC CGTGGCACCC TGAGGCCCCT CCCCGGCCAG
 301 GGCCTGAGTC TCGACATCTC CGACGCCTAC ATCCACGTGC GGGGCAGCTG
 351 GAAGGTGCGC AAGGCGTTCC TGAGACTGAA GAACTCCTTT GACCTGTATG
 401 TCAAGGGCCT CACCATTTCC GTCCACCTCG TGTTGGGCAG CGAGTCCTCC
 451 GGGAGGCCCA CGGTCACCAC CTCCAGCTGC AGCAGCGACA TCCAGAACGT
 501 GGAGTTGGAC ATAGAGGGGG ACCTGGAGGA GCTGCTGAAC CTCCTCCAAA
 551 GCCAGATCGA TGCCAGGCTG CGCGAAGTGC TGGAGAGCAA GATTTGCAGG
 601 CAGATTGAGG AAGCCGTGAC GGCCCACCTG CAGCCTTATC TACAGACACT
 651 GCCAGTCACA ACGCAGATCG ACAGCTTTGC CGGCATTGAC TACAGCTTGA
 701 TGGAGGCCCC CCGGGCAACA GCTGGGATGT GGATGTGAT GTTTAAGGGT
 751 GAAATTTTCC CTCTGGATCA CCGCAGCCCA GTGGACTTCC TTGCTCCAGC
 801 CATGAACCTC CCCGAGGCTC ACAGCCGAAT GGTCTACTTT TCCATCTCCG
 851 ATTACGTCTT CAACACCGCC AGCCTGGCCT ACCACAAGTC AGGGTACTGG
 901 AACTTCTCCA TCACAGACGC CATGGTTCCG GCCGACCTCA ACATCCGGCG
 951 GACCACCAAG TCCTTCCGAC CCTTCGTTCC CCTGCTTGCC AATCTCTACC
1001 CCAACATGAA CTTGGAGCTC CAAGGGACAG TGAACTCGGA CAACTGGTG
1051 AACCTCAGCA CCGAGAATCT GTAGAGGAA CCCGAGATGG ATATTGAGGC
1101 CTTGGTGGTC CTGCCCAGCT CTGCCAGGGA GCCTGTCTTC CGGCTGGGTG
1151 TGGCCACTAA TGTGTCTGCC ACACTGACCT TGAACACCAG GAAGATCACT
1201 GGGTTCCTGA AGCCGGGAAG GCTACAGGTG GAACTGAAAG AATCCAAAGT
1251 CGGAGGATTC AATGTGGAGC TGTTGGAAGC TCTCCTCAAC TACTACATTC
1301 TCAACAACCT CTACCCCAAG GTCAATGAGA AGTTGGCCCA CCGCTTCCCG
1351 CTCCCTCTGC TGAGGCACAT TCAGCTCTAC GACCTGCTTC TCCAGACCCA
1401 CGAGAACTTC CTGCTCGTGG GCGCCAACAT CCAGTACAGG AGAGTT
```

FIG. 20

```
   1 ATGGGGGCCT TGGCAAGAGC CCTGCCGTCC ATACTGCTGG CATTGCTGCT
  51 TACGTCCACC CCAGAGGCTC TGGGTGCCAA CCCCGGCTTG GTCGCCAGGA
 101 TCACCGACAA GGGACTGCAG TATGCGGCCC AGGAGGGGCT ATTGGCTCTG
 151 CAGAGTGAGC TGCTCAGGAT CACGCTGCCT GACTTCACCG GGGACTTGAG
 201 GATCCCCCAC GTCGGCCGTG GGCGCTATGA GTTCCACAGC CTGAACATCC
 251 ACAGCTGTGA GCTGCTTCAC TCTGCGCTGA GGCCTGTCCC CGGCCAGGGC
 301 CTGAGTCTCA GCATCTCCGA CTCCTCCATC CGGGTCCAGG GCAGGTGGAA
 351 GGTGCGCAAG TCATTCTTCA AACTACAGGG CTCCTTTGAT GTCAGTGTCA
 401 AGGGCATCAG CATTTCGGTC AACCTCCTGT TGGGCAGCGA GTCCTCCGGG
 451 AGGCCCACAG GTTACTGCCT CAGCTGCAGC AGTGACATCG CTGACGTGGA
 501 GGTGGACATG TCGGGAGATT CGGGGTGGCT CTTGAACCTC TTCCACAACC
 551 AGATTGAGTC CAAGTTCCAG AAAGTACTGG AGAGCAGGAT TTGCGAAATG
 601 ATCCAGAAAT CAGTGTCCTC CGATCTACAG CCTTATCTCC AAACTCTGCC
 651 AGTTACAACA GAGATTGACA GTTTCGCCGA CATTGATTAT AGCTTAGTGG
 701 AAGCCCCTCG GGCAACAGCC CAGATGCTGG AGGTGATGTT TAAGGGTGAA
 751 ATCTTTCATC GTAACCACCG TTCTCCAGTT ACCCTCCTTG CTGCAGTCAT
 801 GAGCCTTCCT GAGGAACACA ACAAAATGGT CTACTTTGCC ATCTCGGATT
 851 ATGTCTTCAA CACGGCCAGC CTGGTTTATC ATGAGGAAGG ATATCTGAAC
 901 TTCTCCATCA CAGATGACAT GATACCGCCT GACTCTAATA TCCGACTGAC
 951 CACCAAGTCC TTCCGACCCT TCGTCCCACG GTTAGCCAGG CTCTACCCCA
1001 ACATGAACCT GGAACTCCAG GGATCAGTGC CCTCTGCTCC GCTCCTGAAC
1051 TTCAGCCCTG GGAATCTGTC TGTGGACCCC TATATGGAGA TAGATGCCTT
1101 TGTGCTCCTG CCCAGCTCCA GCAAGGAGCC TGTCTTCCGG CTCAGTGTGG
1151 CCACTAATGT GTCCGCCACC TTGACCTTCA ATACCAGCAA GATCACTGGG
1201 TTCCTGAAGC AGGAAAGGT AAAAGTGGAA CTGAAAGAAT CCAAAGTTGG
1251 ACTATTCAAT GCAGAGCTGT TGGAAGCGCT CCTCAACTAT TACATCCTTA
1301 ACACCCTCTA CCCCAAGTTC AATGATAAGT TGGCCGAAGG CTTCCCCCTT
1351 CCTCTGCTGA AGCGTGTTCA GCTCTACGAC CTTGGGCTGC AGATCCATAA
1401 GGACTTCCTG TTCTTGGGTG CCAATGTCCA ATACATGAGA GTTTGAGGAC
1451 AAGAAAGATG AAGCTTGGAG GTCACAGGCT GGATCTGCTT GTTGCATTTC
1501 CAGCTGTGCA GCACGTCTCA GAGATTCTTG AAGAATGAAG ACATTTCTGC
1551 TCTCAGCTCC GGGGGTGAGG TGTGCCTGGC CTCTGCCTCC ACCCTCCTCC
1601 TCTTCACCAG GTGCATGCAT GCCCTCTCTG AGTCTGGACT TTGCTTCCCC
1651 TCCAGGAGGG ACCACCCTCC CCGACTGGCC TGGGATATCT TTACAAGCAG
1701 GCACTGTATT TTTTATTCG CCATCTGATC CCCATGCCTA GCAGAGTGCT
1751 GGCACTTAGT AGGTCCTCAA TAAATATTTA GGTCGACGAG CTCGAGAATT
1801 C
```

ACUTE PHASE PROTEIN MODULATING ENDOTOXIC ACTIVITY OF LIPOPOLYSACCHARIDES, ASSAY METHODS AND POLYPEPTIDES

CROSS-REFERENCE TO RELATED APPLICATION

This is a divisional of U.S. patent application Ser. No. 08/240,328 filed May 10, 1994, issuing on Dec. 16, 1997 as U.S. Pat. No. 5,698,680, which is a divisional application of Ser. No. 07/847,562, issued on May 10, 1994 as Pat. No. 5,310,879, which was filed on Mar. 2, 1992, which is a continuation-in-part of application Ser. No. 07/367,454, filed Jun. 16, 1989, now U.S. Pat. No. 5,245,013, which is a continuation-in-part of application Ser. No. 07/006,710 filed Dec. 30, 1986, now abandoned, which was a continuation in part of application Ser. No. 06/728,833 filed Apr. 30, 1985, now abandoned, both of whose disclosures are incorporated by reference.

This invention was made with government support by grant no. AI15136 from the National Institutes of Health. The government has certain rights to the invention.

TECHNICAL FIELD

The present invention relates to a protein that binds to lipopolysaccharides secreted by Gram-negative bacteria in an infected host animal, and particularly to the use of that protein in assaying for Gram-negative bacterially secreted lipolysaccharide.

BACKGROUND ART

The wide variety of microorganisms commonly found in the gastrointestinal tract, particularly the Gram-negative, nonsporulating bacilli, have become increasingly important in clinical medicine. They are the principal organisms found in infections of the abdominal viscera, peritoneum, and urinary tract, as well as being frequent secondary invaders of the respiratory tract, burned or traumatized skin, and sites of decreased host resistance and instrumentation. Currently, they are the most frequent cause of life- threatening bacteremia.

The gastrointestinal flora are exceedingly complex. The large intestine contains about $10^{10}$ to $10^{11}$ organisms per gram of contents. Of these, 90 to 95 percent are obligate anaerobes. Most common are the Gram-negative bacilli, Bacteroides and Fusobacterium, gram-positive bacilli, including Bifidobacterium, Eubacterium, and Corynebacterium species, and a wide variety of anaerobic *streptococci*. Other anaerobes include the Gram-positive spore-forming rods of the *clostridia* species and Gram-negative cocci, Veillonella. Enterococci are also present. The well-known aerobic Gram-negative rods, which are members of the family Enterobacteriaceae, account for only 5 to 10 percent of the total flora. These include the most common, *E. coli*, as well as the Klebsiella-Enterobacter group, Proteus, Providencia, Edwardsiella, Serratia, and under pathologic conditions, Salmonella and Shigella.

The Gram-negative bacteria of the gastrointestinal tract produce disease by invasion of tissue and by release of a pharmacologically active lipopolysaccharide (LPS) from the cell wall, known as endotoxin. Endotoxins from a wide variey of unrelated species behave quite similarly, regardless of the inherent pathogenicity of the microorganism from which they are derived or their antigenic structure.

In the intact microorganism, endotoxins exist as complexes of lipid, polysaccharide, glycolipid and non-covalently-bound protein. The biologic activity seems to be a property of a lipid and carbohydrate portion.

The lipopolysaccharides of Gram-negative bacteria may be roughly divided into three structural regions. The outermost region contains the chains of specific sugars that characterize the O-specific antigens and determine individual serotypes within a species. The specific sugars are linked to a core polysaccharide that is of similar structure among related groups of bacteria. The core is in turn linked through 2-keto-3-deoxyoctonate disaccharides to the major lipid component termed lipid A. Evidence has now accumulated to indicate that the properties of endotoxins may be accounted for by this complex lipid substance.

Lipid A is a glucosamine disaccharide esterified with phosphoric and pyrophosphoric acid and also contains ester- or amide-linked lauric, palmitic, and myristic acids. Perhaps the most important finding in recent years is that the lipid A and core- polysaccharide regions are immunogenic and can induce antibodies that cross-react among the Gram-negative bacteria.

Animal studies reveal that antibodies prepared against these components of endotoxin protect against challenge from heterologous Gram-negative bacteria. However, better protection is reportedly obtained by immunization with specific O-antigens that induce opsonizing antibodies.

Upon entry into the bloodstream and initiation of endotoxemia, LPS and blood humoral and cellular elements interact. The work of several groups has shown that the blood-borne LPS partitions between the tissues and plasma lipoproteins, with specific binding to high density lipoprotein (HDL). Freudenberg et al. (1980) *Infec. Immun.* 28:373; Mathison and Ulevitch (1979) *J. Immunol.* 123:2133; Munford et al. (1982) *J. Clin. Invest.* 70:877; and Ulevitch et al. (1981) *J. Clin. Invest.* 67:827.

Depending upon the source and isolated form of LPS, about 10–50 percent of the initially administered LPS partitions to the plasma lipoproteins (HDL), with the remainder going to the tissues. Clearance from the animal body appears to be via the tissues and into bile. Thus, if the partitioning between plasma lipoproteins and tissues could be adjusted to be less favorable to HDL, LPS could be more quickly cleared from the body of the infected animal.

In view of the above reports and the findings discussed hereinafter, an early example of improved clearance may have been reported by Filkins (1976) *Proc. Soc. Exptl. Biol. Med.* 151:89. It was there reported that rats treated with whole rat blood plasma and serum from either post-endotoxic or post-trauma donors manifested detoxifying potential in rats into which *Salmonella enteritidis* LPS had been injected. In contrast, normal rat blood and phosphate-buffered saline controls exhibited no detoxification. A role for the reticuloendothelial system in elaboration of the blood anti-endotoxin system was postulated.

It has also been reported that acute phase rabbit serum (APRS) modifies the interactions of LPS with HDL by retarding the in vitro rate of binding of LPS to HDL, thereby modulating the endotoxic effect of the LPS. Tobias and Ulevitch (1983) *J. Immunol.* 131:1913. Binding of LPS to components of normal rabbit serum (NRS) has also been reported. Ulevitch and Johnston (1978) *J. Clin. Invest.* 62:1313; Ulevitch et al. (1979) *J. Clin. Invest.* 64:1516; Ulevitch et al. (1981) *J. Clin. Invest.* 67:827; Munford et al. (1981) *J. Clin. Invest.* 70:877; and Freudenberg et al. (1980) *Infect. Immun.* 28:373.

In rabbits, the interaction of LPS with HDL can be accounted for by a two-step mechanism in which the LPS is first disaggregated by the action of serum proteins. The disaggregated LPS thereafter binds with HDL to form the observed complex. It is believed that similar mechanisms apply in other animals, including man.

Mixtures of LPS with rabbit serum that are permitted to react for 30 minutes at 37 degrees C. provide an LPS complex with a density of less than about 1.2 grams per cubic centimeter (g/cc). When NRS is used, the complex contains components of HDL including apolipoprotein AI (apo AI) [Ulevitch et al. (1981) *J. Clin. Invest.* 67:827], while with APRS the complex contains apo AI and also serum amyloid A apolipoprotein (apo SSA) [Tobias et al. (1982) *J. Immunol.* 128:1420].

While complexes with densities of about 1.2 g/cc are ultimately formed by admixture of LPS with NRS and with APRS, the times for formation of similar amounts of those complexes differ. Thus, for NRS, the formation of the 1.2 g/cc complex is about 90 percent complete within about 30 minutes, while in APRS, the complex is about 95 percent formed after a time period of about 6 hours. Tobias and Ulevitch (1983) *J. Immunol.* 131:1913.

In addition to the time courses of complex formation being different in NRS as compared to APRS, initial complexes formed in the two serum types also differ in density. Thus, in NRS, the density of the initially formed complex is 1.33 g/cc, while in APRS, the density of the intial complex is 1.3. An LPS- containing serum complex with a density of 1.3 g/cc was also reported when Balbc/Strong mice were injected with $AgNO_3$ or LPS. Tobias and Ulevitch (1983) *J. Immunol.* 131:1913.

Precipitated euglobulin fractions formed from mixtures of LPS and NRS or APRS were examined for their solubilities in saline. It was found that substantially all of the LPS in the NRS-formed precipitate dissolved leaving only about 1 percent of the recovered, precipitated LPS undissolved, while most of the LPS that precipitated from APRS did not dissolve in saline.

Dissolution of the saline-insoluble precipitates followed by SDS-PAGE analysis indicated that the APRS-formed precipitated complex contained a newly identified protein having an apparent relative molecular weight of about 60,000. That new protein was found to be a glycoprotein by staining with periodic acid-Schiff stain, and was referred to as gp60. Tobias and Ulevitch (1983) *J. Immunol.* 131:1913.

Data for the time-dependent shift of density and LPS precipitability from NRS and APRS showed similar time courses. In addition, SDS-PAGE analysis of precipitates taken at various times after admixture of LPS with APRS showed the gp60 material as well as possibly two other proteins of molecular weights of about 57,000 and about 79,000 interact with LPS to modify LPS/HDL binding kinetics. Tobias and Ulevitch (1983) *J. Immunol.* 131:1913.

It thus appeared that at least the before- described gp60 material was involved in mediating the binding of LPS to HDL. Subsequent work, discussed hereinafter, has however shown that that gp60 material is not the substance that retards binding between HDL and LPS, and it was believed that the homologous human protein was a known protein, an $alpha_2,beta_1$-glycoprotein first reported by Iwasaki and Schmid (1970) *J. Biol. Chem.* 245:1814. That belief has now been found in error. The substance that retards binding is a newly identified glycoprotein, and is refered to hereinafter as lipopolysaccharide binding protein (LBP), or just a binding protein.

BRIEF SUMMARY OF THE INVENTION

The present invention relates to a protein that binds to lipopolysaccharides secreted by Gram-negative bacteria that infect a host animal, an assay for the presence of lipopolysaccharide utilizing that binding protein, a polypeptide and antibodies.

One aspect of the invention constitutes a purified binding protein that binds to lipopolysaccharide that can be present in the bloodstream of an animal host that is susceptible to infection by lipopolysaccharide-secreting Gram-negative bacteria. The purified binding protein has the following properties:

(a) it is a material that is identical or homologous to a binding protein that is present in impure form in the acute phase serum of the animal host, but is substantially absent from the normal serum of the host; i.e., it is present at a concentration of less than about 0.5 micrograms per milliliter of normal serum; (b) it binds to a Gram-negative bacterially-secreted lipopolysaccharide when the purified binding protein and lipopolysaccharide are admixed in vitro in normal serum of the animal host to form a LBP-LPS complex having a density of 1.3 g/cc; (c) it retards the in vitro binding of the lipopolysaccharide to high density lipoprotein present in the normal serum of the host animal but permits formation of a LPS-HDL complex having a density of 1.2 g/cc or less; (d) it immunoreacts with antibodies raised to a polypeptide having the amino acid residue sequence, from left to right and in the direction from amino-terminus to carboxy-terminus, of Thr—Asn—Pro—Gly—Leu—Ile—Thr—Arg—Ile—Thr—
Asp—Lys—Gly—Leu—Glu—Tyr—Ala—Ala—Arg—Glu—
Gly—Leu—Leu—Ala—Leu—Gln—Arg—Lys—Leu—Asn(Leu)—
Gly—Val—Thr—Leu—Pro—Asp—Phe(Ser)—Asp—Gly;

wherein each of the parenthesized amino acid residue is an alternative to the immediately preceding residue in the sequence; and (e) it is substantially homogeneous. The purified binding protein is often referred to herein as lipopolysaccharide binding protein (LBP).

Two purified LBP homologs have thus far been isolated and are illustrative of the similar molecules present in impure form in the acute phase serum of other animals. The purified human binding protein is preferably isolated from human serum or is prepared by genetic engineering techniques as a recombinant protein, having a molecular weight of about 59,500 daltons [or 59.5 kilodaltons (kD)] when glycosylated, about 53,000 when expressed without glycosylation and including a 26-residue leader sequence, or about 50,000 from the unglycosylated mature protein. The purified lapine LBP molecule has a molecular weight of about 60 kD and is five residues longer than the human protein. Weights can differ with glycosylation depending on expression system when used and the animal providing the gene or protein so the molecular weight of the mature secreted protein present in impure form in acute phase sera is broadly referred to as being about 55 kD to about 75 kD.

A further aspect of the present invention contemplates a method of assaying an animal body sample for the presence of a lipopolysaccharide endotoxin secreted by Gram-negative bacteria. In this method, an aliquot of an animal body sample is provided, and is admixed with an unmasking reagent to to unmask any endotoxin present in the sample aliquot. The aliquot containing unmasked endotoxin is admixed in an aqueous medium with a purified binding protein as described hereinbefore. The admixture so formed is maintained for a predetermined time period sufficient for the purified binding protein to react with lipopolysaccharide that may be present in the aliquot and form a complex. The presence of a complex formed between the binding protein and lipopolysaccharide is then determined, the presence of such a complex indicating that the lipopolysaccharide was present in the body sample aliquot.

The above assay method can be carried out using techniques analogous to those of receptor-ligand assays such as antibody-antigen assays wherein the purified binding protein is treated as the receptor and the lipopolysaccharide is the ligand. The assay method can also be utilized in a centrifugal density gradient assay where the presence of a formed complex can be determined by its density relative to the densitites of the admixed protein or binding protein.

Still another aspect of the invention consists essentially of a synthetic polypeptide corresponding in sequence to all or a portion of the amino-terminal 39 residues of the rabbit (lapine) binding protein whose amino residue sequence is shown below (A and B), from left to right and in the direction from amino-terminus to carboxy-terminus:

```
         1                                              10
A: Thr—Asn—Pro—Gly—Leu—Ile—Thr—Arg—Ile—Thr—
B: Thr—Asn—Pro—Gly—Leu—Ile—Thr—Arg—Ile—Thr—

11                                              20
A: Asp—Lys—Gly—Leu—Glu—Tyr—Ala—Ala—Arg—Glu—
B: Asp—Lys—Gly—Leu—Glu—Tyr—Ala—Ala—Arg—Glu—

21                                              30
A: Gly—Leu—Leu—Ala—Leu—Gln—Arg—Lys—Leu—XXX—
B: Gly—Leu—Leu—Ala—Leu—Gln—Arg—Lys—Leu—Leu 31                                              39
A: Gly—Val—Thr—Leu—Pro—Asp—Phe—Asp—Gly
B: Gly—Val—Thr—Leu—Pro—Asp—Phe—Asp—Gly
``` wherein residue number 30 (XXX) in sequence A is indeterminate, and believed to be asparagine (Asn).

The sequence A was obtained by the present inventors, whereas the B sequence was subsequently determined by Dr. Ralf Schumann of the inventors' laboratory working under the direction and control of the present inventors. The sequence differences at positions 30 and 37 are presently unexplained and may be simply due to differences in protein sequence of the animals studied.

The lapine polypeptide of this invention can contain a sequence of about 6 to about 39 residues corresponding to the above sequences, and more preferably contains about 10 to about 25 residues.

Antibodies to the above polypeptides A and B, and the human homologous polypeptide from the N-terminus to position 20 from that terminus are also contemplated.

The complete amino acid sequence of lapine LBP, which contains 482 residues including a 26 residue leader or signal peptide at the amino-terminus, is shown in FIG. 17, with the DNA coding sequence being shown in FIG. 18.

The complete human LBP contains a sequence of about 477 residues, including a 25 residue leader or signal sequence at the amino-terminus. The complete amino acid residue sequence is shown in FIG. 19, with the DNA coding sequence being shown in FIG. 20.

BRIEF DESCRIPTION OF THE DRAWINGS

In the drawings forming a portion of this disclosure.

Figure 1A:
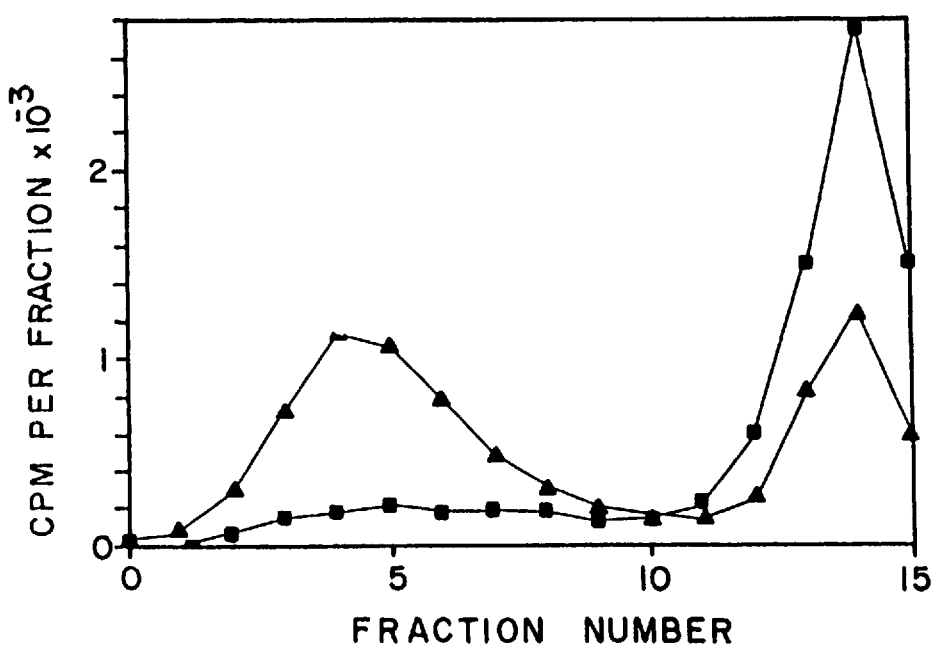
FIG. 1 contains two graphs that illustrate the observation and quantitation of the 1.3 grams/cubic centimeter (g/cc) complex (C1.3) formed between the lipopolysaccharide endotoxin (LPS) secreted by *Salmonella minnesota* Re595 and human serum components in which the serum was collected before and after acute phase induction.

The graph of FIG. 1a is a plot of individual cesium chloride (CsCl) density gradients showing the ability of normal (■) and acute (▲) human sera, respectively, to form C1.3. The ordinate of that graph is in counts per minute (CPM) times $10^{-3}$ observed from $^3$H-LPS in each fraction collected from the gradient. The abscissa lists the fraction numbers in which the counts were observed.

Figure 1B:
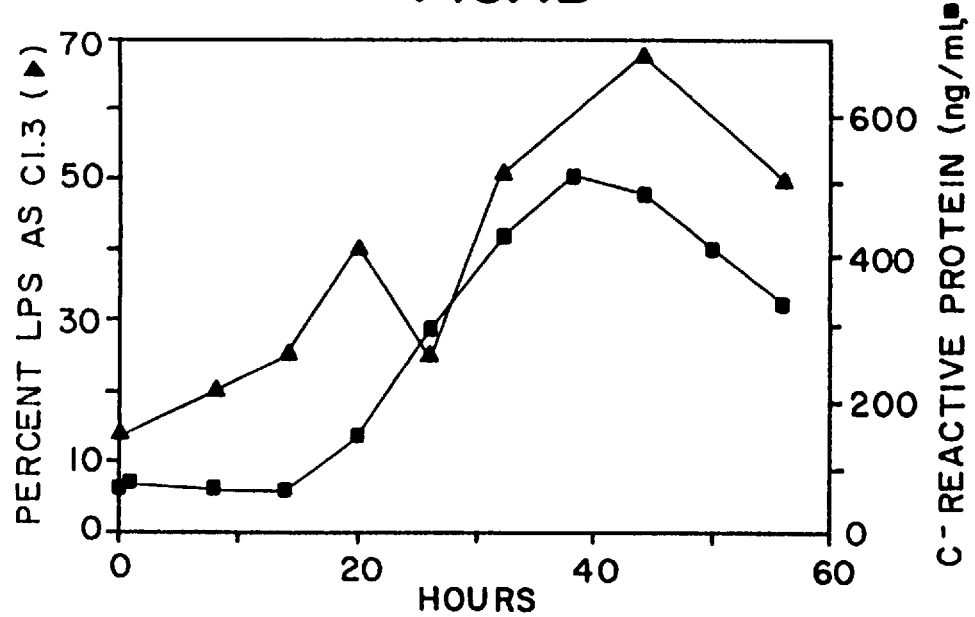

FIG. 1b shows the time dependence of (i) the ability of human serum to form C1.3 after acute phase was induced by etiocholanolone (▲) and (ii) the C- reactive protein (CRP) concentration in human serum after similar acute phase induction (■). The left-hand ordinate is in units of percent $^3$H- LPS present as C1.3, while the right-hand ordinate shows the concentration of CRP in nanograms per milliliter (ng/ml). The abscissa is in units of hours after acute phase induction.

Figure 2:
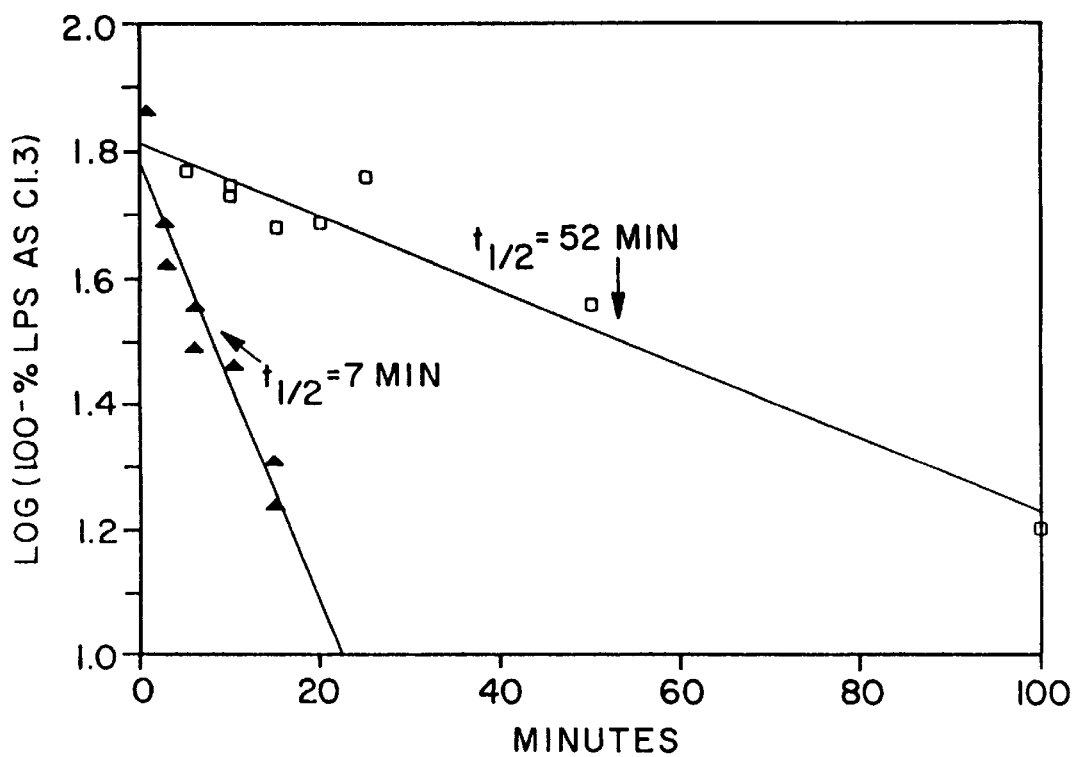

FIG. 2 is a graph showing plots of the kinetics of Re595 LPS-HDL complex formation in normal human serum that was collected immediately prior to injection of etiocholanolone (▲) and in acute phase serum that was collected 32 hours after the etiocholanolone injection (■). The ordinate is in units of log(100-percent $^3$H-LPS present as C1.3), while the abscissa is time in minutes after admixture of the $^3$H-LPS with either serum. Arrows indicate the first order one-half times ($t_{1/2}$) in minutes (min) for the respective plots.

Figure 3:
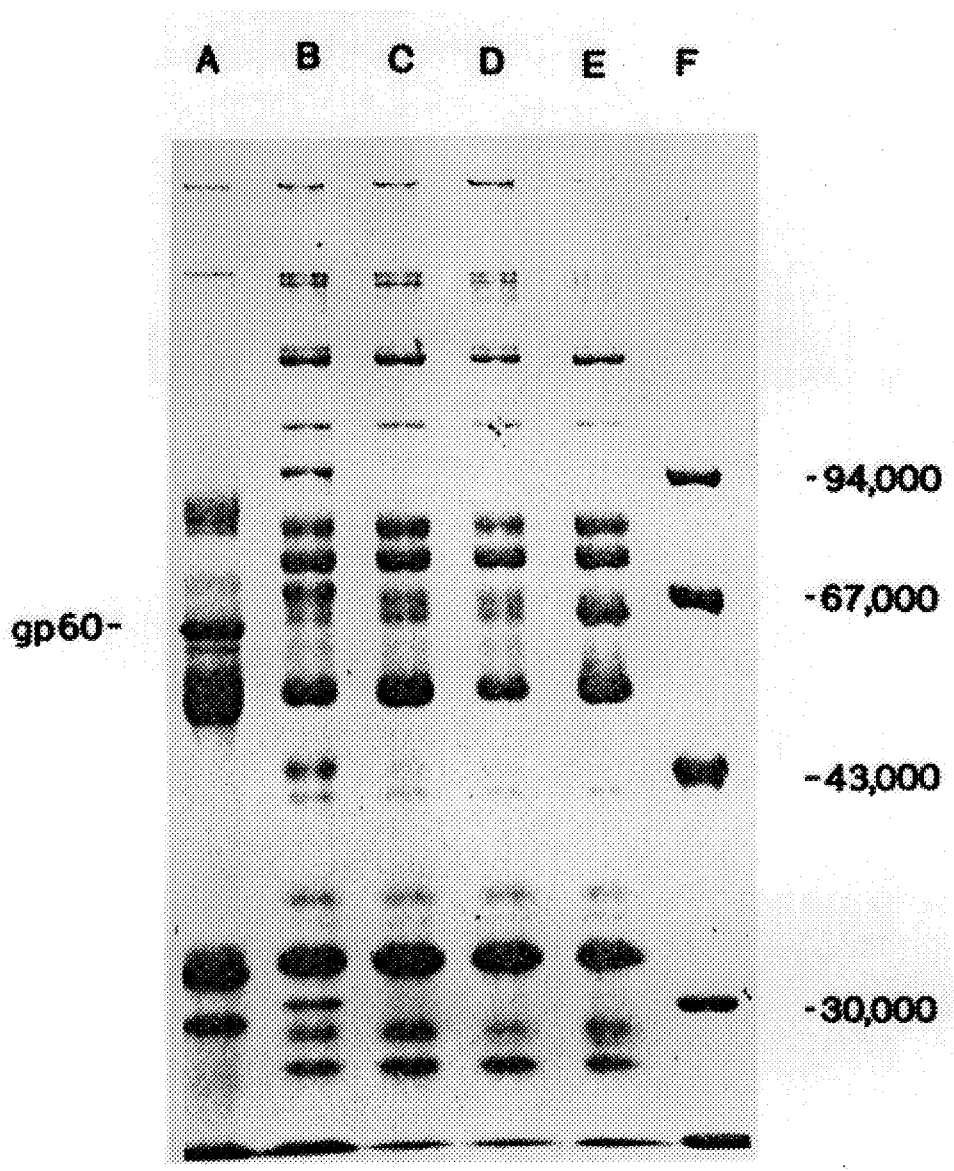

FIG. 3 is a photograph of a polyacrylamide gel electrophoresis analysis carried out in the presence of sodium dodecyl sulfate (SDS-PAGE) as described by Laemmli (1970) *Nature (London)* 222:680. A 5 percent stacking gel was used in conjunction with a 10 percent separating gel. Protein-containing bands were visualized with Coomassie blue. Apparent relative molecular weight markers are shown in the right-hand lane. Those markers were phosphorylase B (94,000), bovine serum albumin (67,000), ovalbumin (40,000), and soybean trypsin inhibitor (30,000). The position of the gp60 material described herein and in Tobias and Ulevitch (1983) *J. Immun.* 131:1913 is indicated on the left by the designation "gp60-".

Protein preparations fractionated by the SDS- PAGE analysis of this figure were: Lane A-rabbit euglobulin precipitated from APRS with LPS; Lane B- euglobulin precipitated from normal human serum (NHS); Lane C-euglobulin precipitated from NHS with LPS; Lane D-euglobulin precipitated from acute phase human serum (APHS); Lane E-euglobulin precipitated from APHS with LPS; and Lane F-molecular weight markers.

Figure 4:
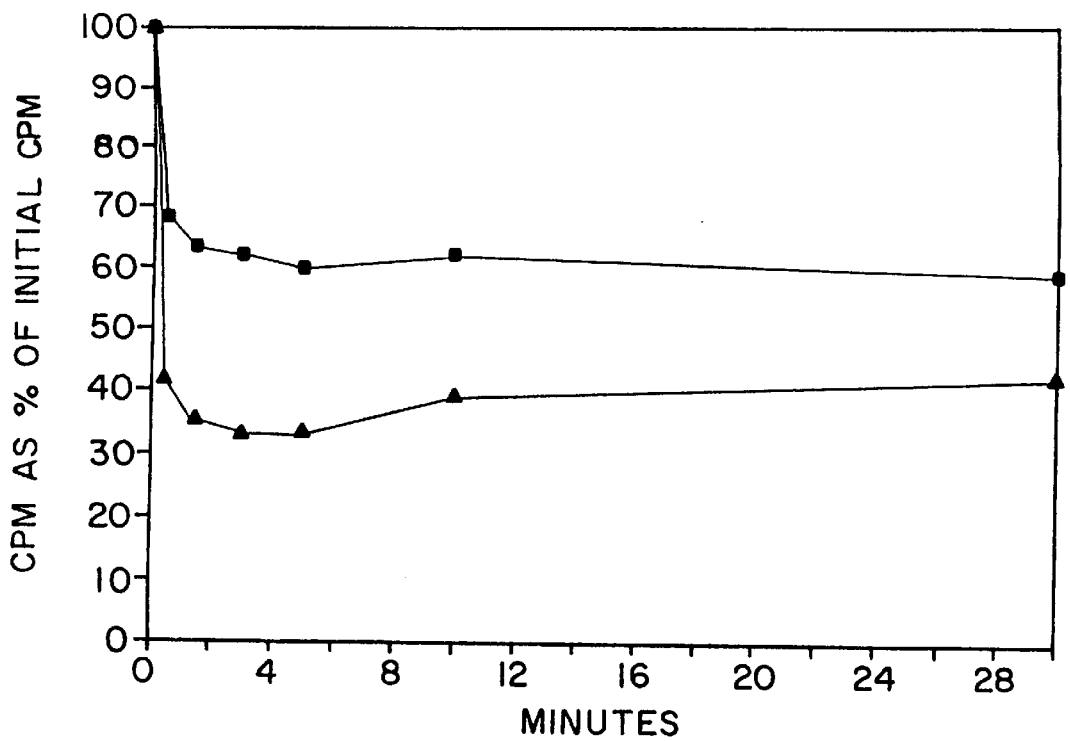

FIG. 4 is a graph showing the in vivo clearance from rabbits of $^3$H-LPS preincubated with delipoproteinated NRS (■) and APRS (▲). Each point in the graphs is the averaged value from 4 to 6 normal rabbits. A catheter was placed in a femoral artery of each rabbit from which blood samples could be taken at desired times.

30 Micrograms (ug) of $^3$H-LPS in 3 milliliters (ml) NRS or APRS that additionally contained 20 millimolar (mM) ethylenediaminetetraacetic acid (EDTA). The resultant admixtures were maintained for a time period of 10 to 30 minutes at room temperature to provide the preincubation. The preincubated admixtures were then injected into the rabbits (time zero).

Blood samples were taken at the times indicated and were allowed to clot. Sera were then collected and assayed by liquid scintillation. The ordinate of the graph is in units of percent of the initial counts per minute (CPM) detected in the blood, while the abscissa is in minutes after the injection of the radiolabeled LPS.

Figure 5:
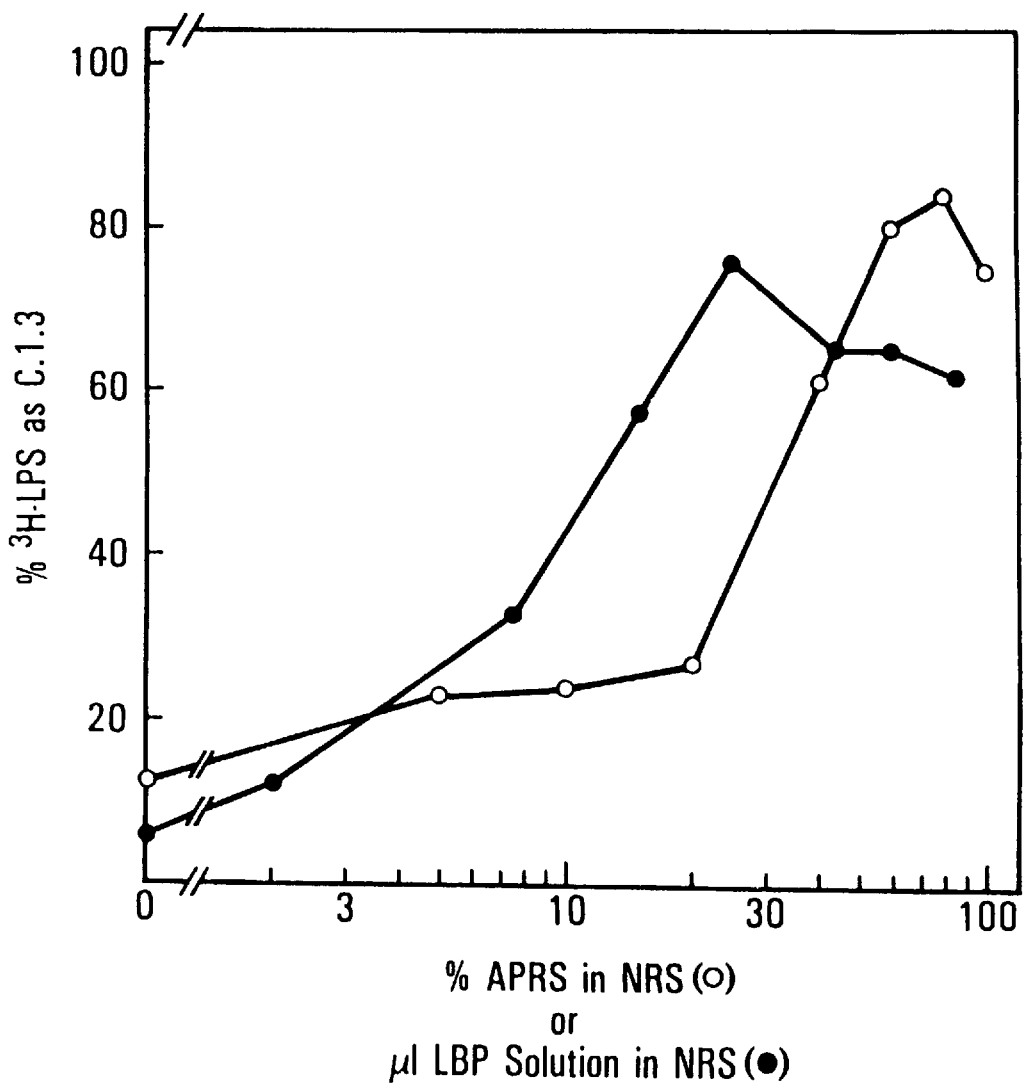

FIG. 5 illustrates examples of the NRS reconstitution assay for LBP activity in which mixtures of APRS with NRS (O) or reconstitution of NRS with LBP (O) are shown. Details are given hereinafter.

Figure 6A:
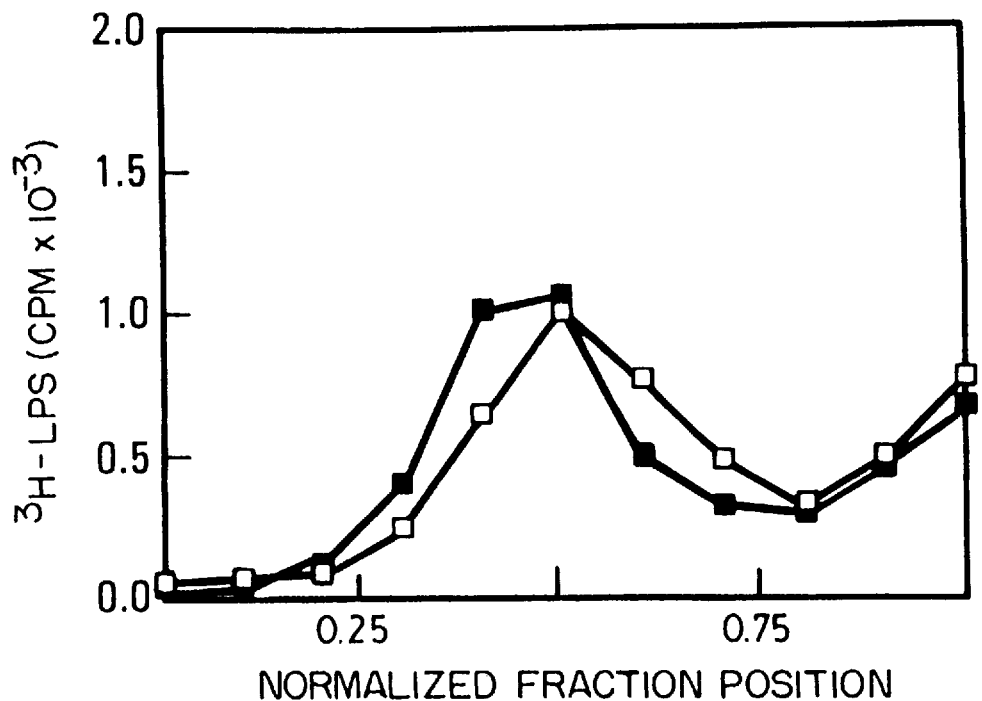
Figure 6B:
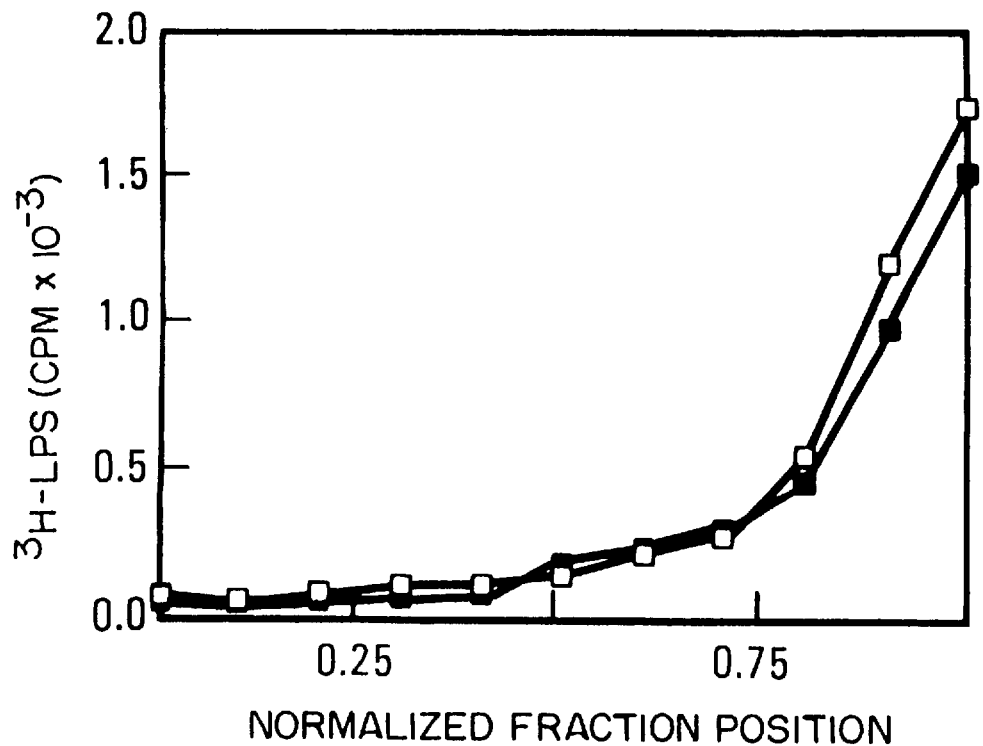

FIG. 6 illustrates CsCl density gradient analyses for C1.3 formation in delipoproteinated APRS (A, upper panel) or delipoproteinated NRS (B, lower panel) reconstituted with lipoproteins from NRS (solid squares) or APRS (open squares).

Figure 7A:
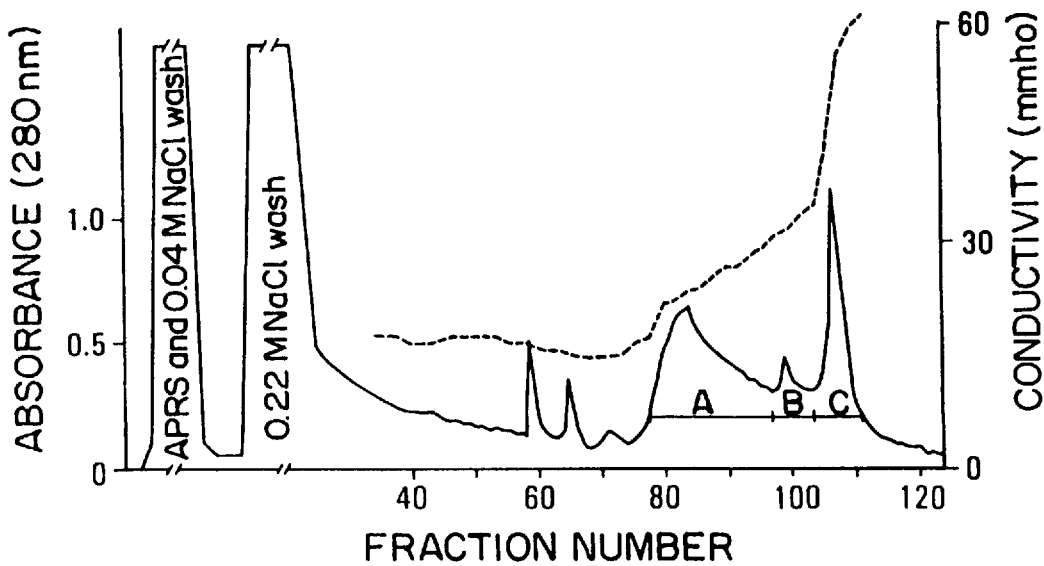

FIG. 7 illustrates ion exchange chromatography on Bio-Rex 70 resin of APRS (A, upper panel) or NRS (B, lower panel). Fractions pooled are denoted by the horizontal lines and letters with the graph. Solid lines, absorbance at 280 nanometers (nm); broken lines, conductivity.

FIG. 8 illustrates CsCl density gradient analyses of LBP activity in pools from Bio-Rex 70 chromatography of APRS (left set of panels) or NRS (right set of panels). Pools tested for activity are identified in FIG. 7. Not all gradients yielded exactly the same numbers of fractions. Thus, the x- axis, "relative fraction position" is used to standardize display of the gradients. A value of zero (0) represents the bottom of the gradient and 1 the top of the gradient.

Figure 9A:
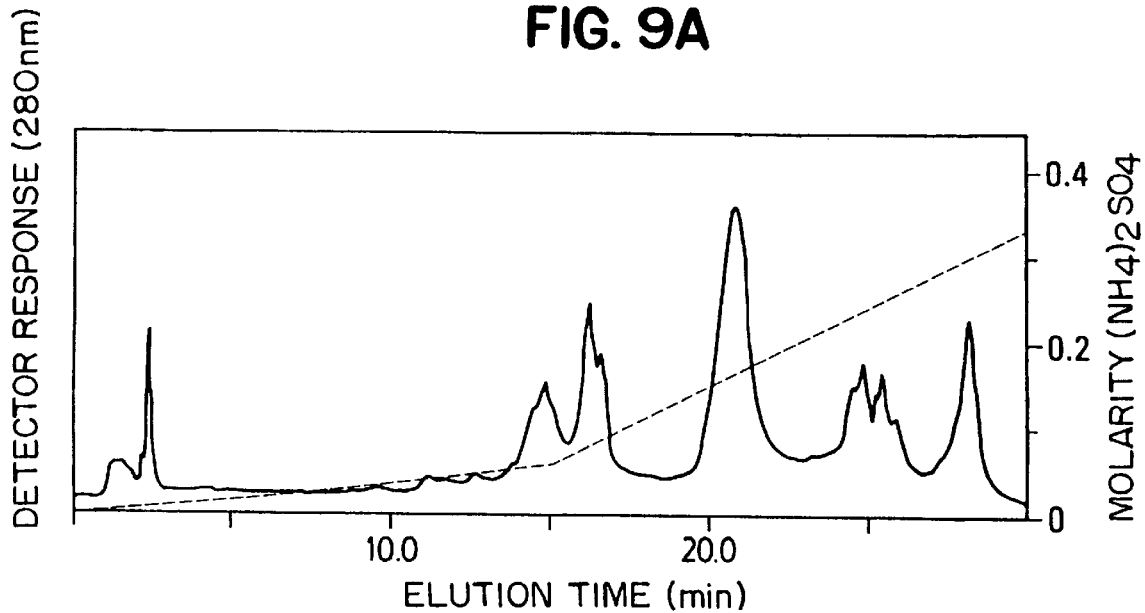
Figure 9B:
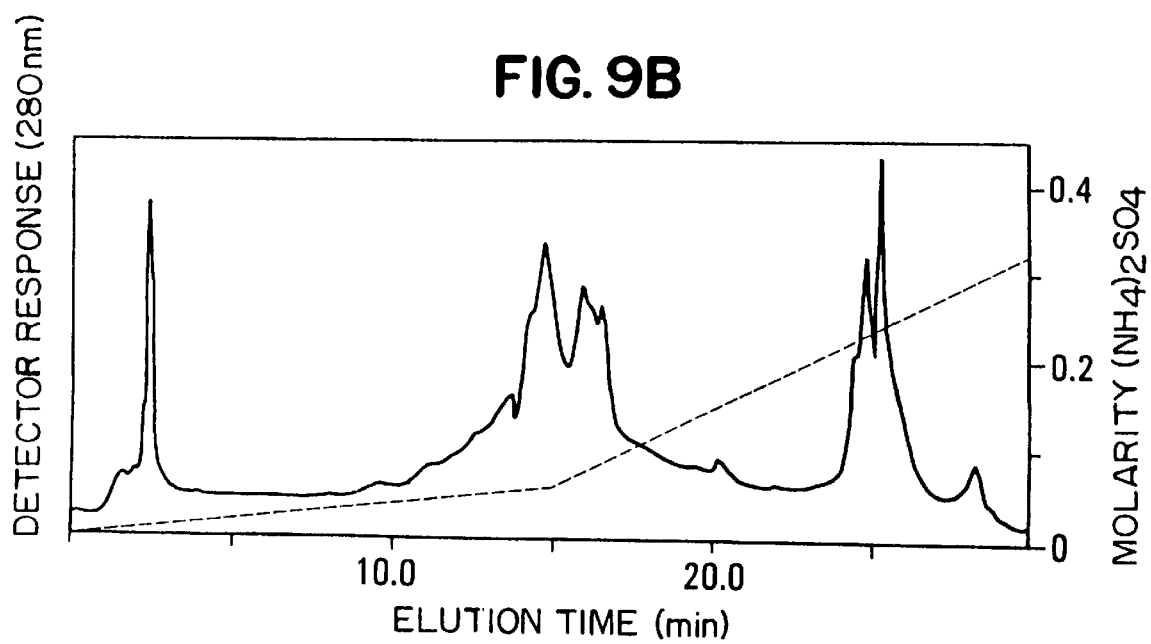

FIG. 9 illustrates ion exchange chromatography on Mono-Q resin of Pools C from Bio-Rex 70 chromatography of APRS (A, upper panel) or NRS (B, lower panel). Solid lines, absorbance at 280 nm; broken lines, molarity of ammonium sulfate. One milliliter (ml) fractions were taken using a 1 milliliter per minute (ml/min) flow rate.

Figure 10A:
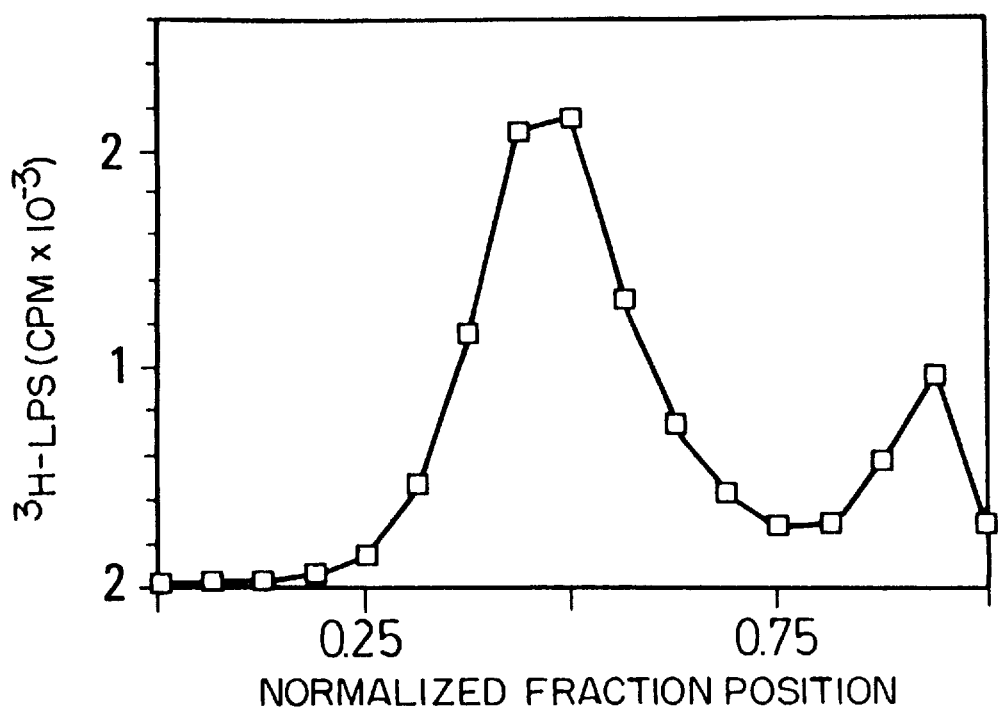
Figure 10B:
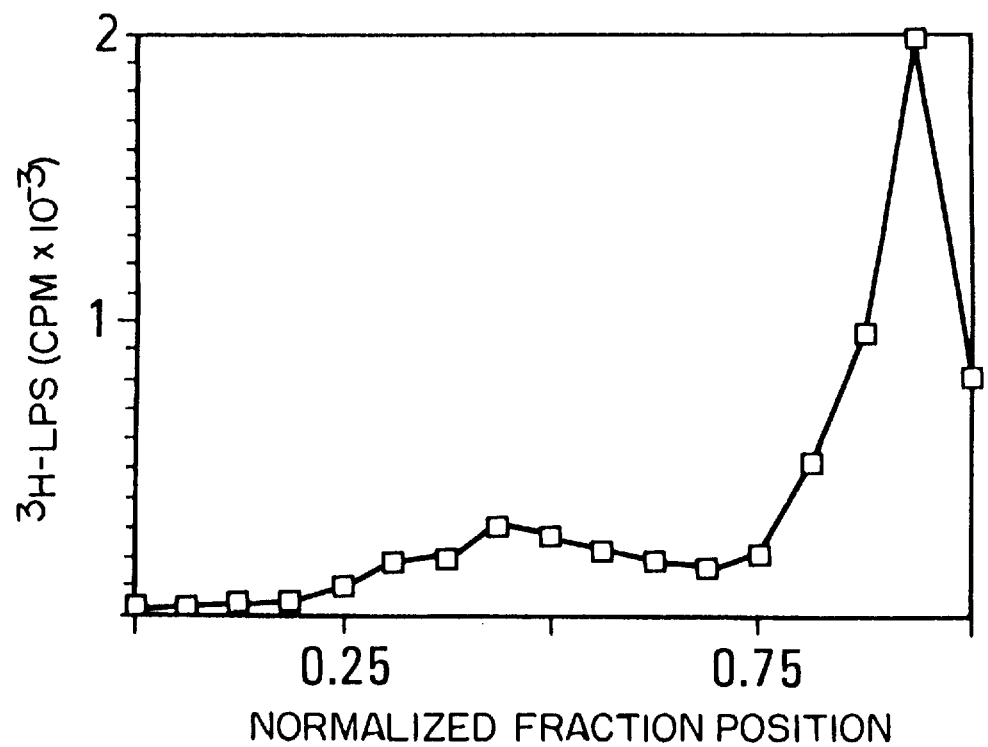

FIG. 10 shows CsCl density gradient analyses of LBP activity in fractions eluting at 20 minutes from Mono-Q chromatography as shown in FIG. 9. Panel A, fractions collected from APRS; Panel B, fractions collected from NRS.

Figure 11:
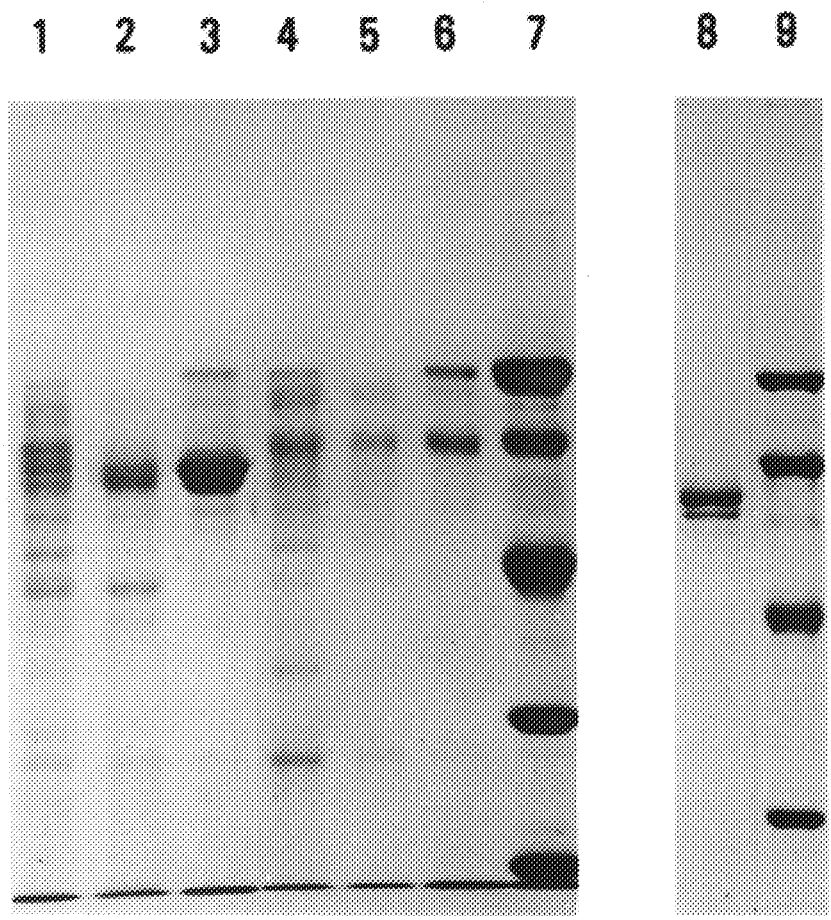

FIG. 11 illustrates SDS-PAGE analyses of chromatography fractions. Lanes 1, 2 and 3 are pools A, B and C from Bio-Rex 70 chromatography of APRS, respectively. Lanes 4, 5 and 6 are pools A, B and C from Bio-Rex 70 chromatography of NRS, respectively. Lane 8 is from the 20 minute fraction from Mono-Q chromatography of pool C, APRS. Lanes 7 and 9 are molecular weight markers having the following apparent molecular masses in kilodaltons (kD): 94 kD, 67 kD, 43 kD, 30 kD.

Figure 12:
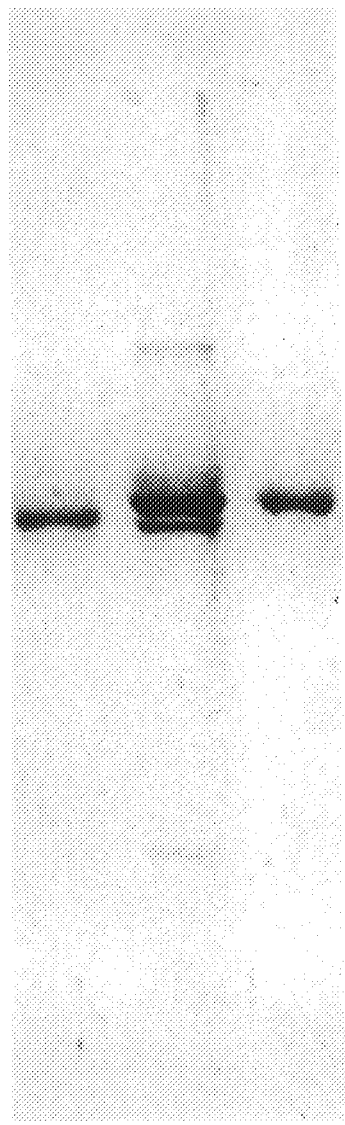

FIG. 12 shows further SDS-PAGE analysis of the 58 kD (lane 1) and 60.5 kD (lane 3) proteins separated electrophoretically from the mixture (lane 2) obtained after Mono-Q chromatography. Details are given hereinafter.

Figure 13:
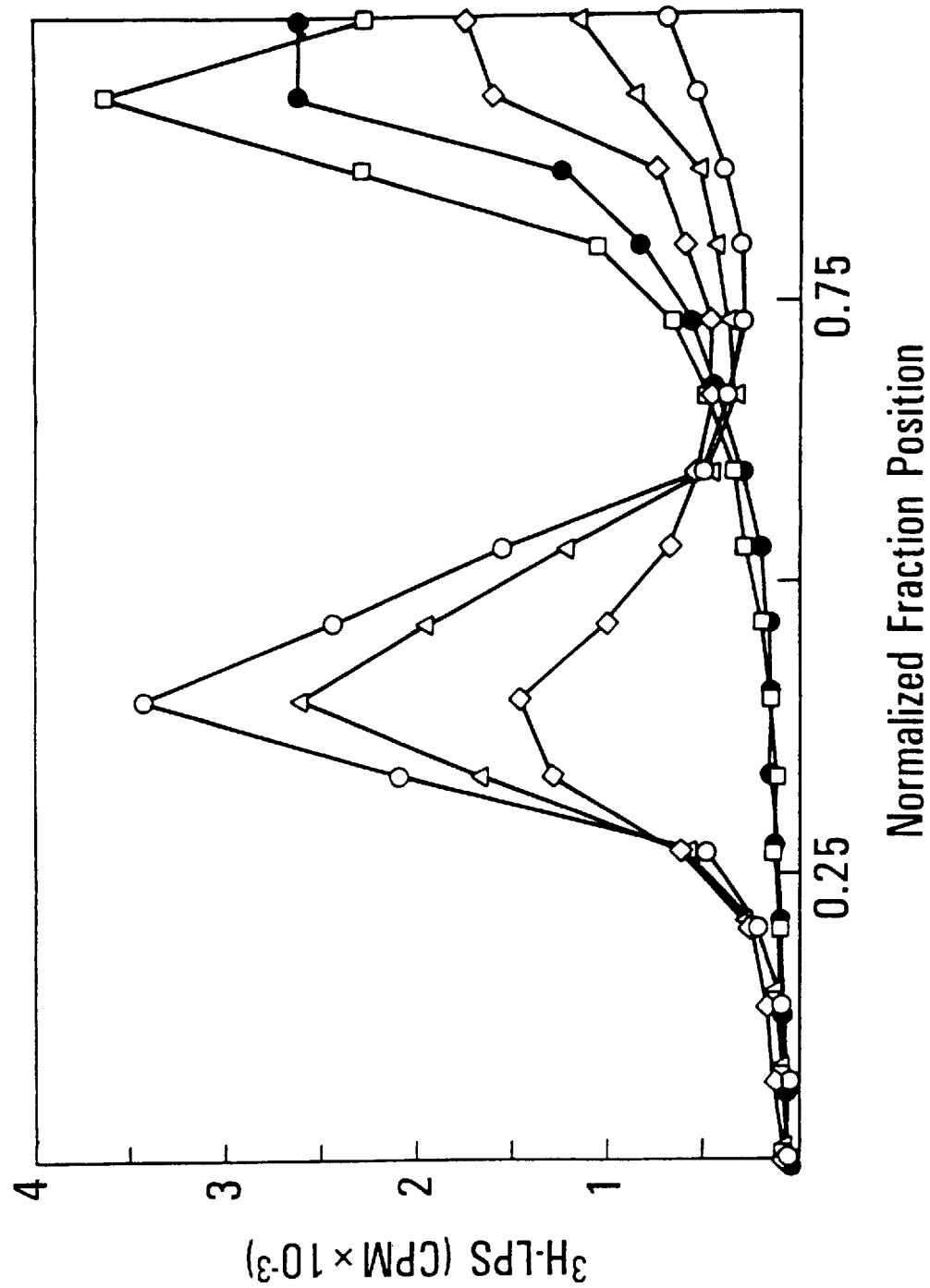

FIG. 13 illustrates CsCl density gradient analyses for LBP activity of immunoprecipitate supernates obtained from mixtures of APRS or NRS and rat anti-LBP antiserum. APRS, no antiserum, O;APRS, 1.7% (v/v) antiserum, ; APRS, 4.6% (v/v) antiserum, ; APRS, 14% (v/v) antiserum, ; NRS, 14% (v/v) antiserum, O.

Figure 14:
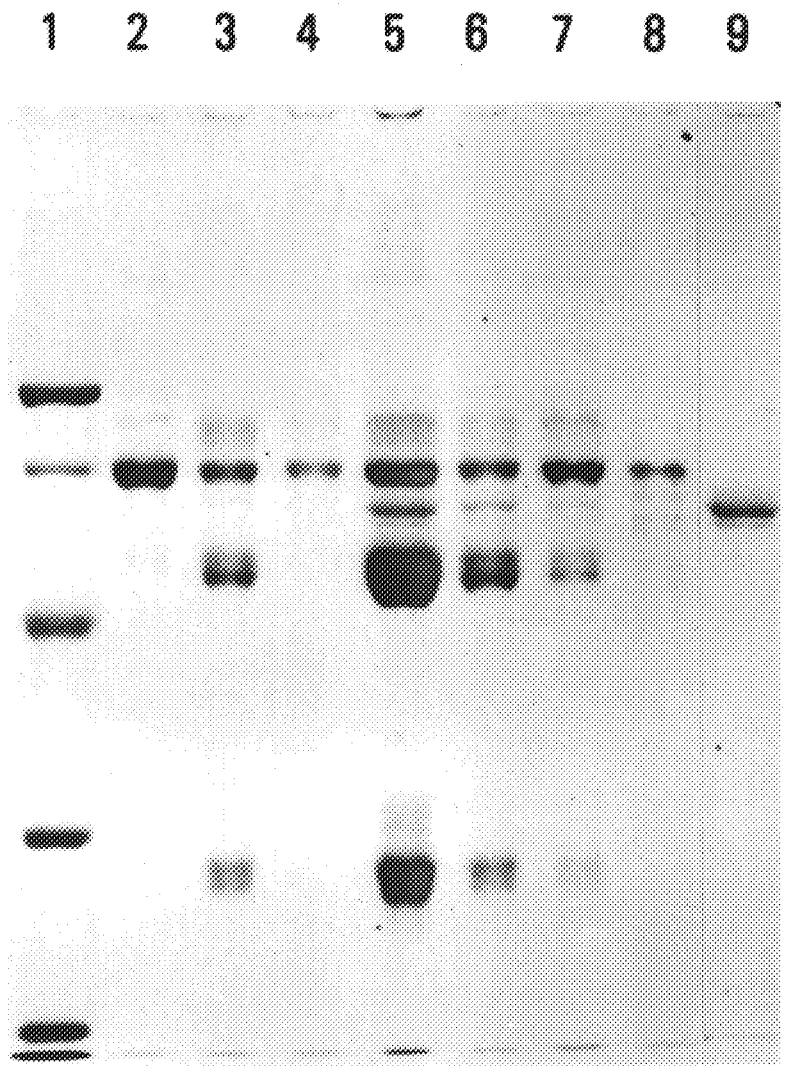

FIG. 14 shows SDS-PAGE analyses of immunoprecipitates obtained from APRS or NRS and anti- LBP antisera. Lane 1, molecular weight (94 kD, 62 kD, 43 kD, 30 kD) markers; lane 2, NRS plus 14% (v/v) pre- immune serum; lane 3, NRS plus 14% (v/v) antiserum; lane 4, APRS plus 14% (v/v) pre-immune serum; lane 5, APRS plus 14% (v/v) antiserum; lane 6, APRS plus 4.6% (v/v) antiserum; lane 7, APRS plus 1.7% (v/v) antiserum; lane 8, APRS plus 0.6% (v/v) antiserum; lane 9, purified LBP.

Figure 15:
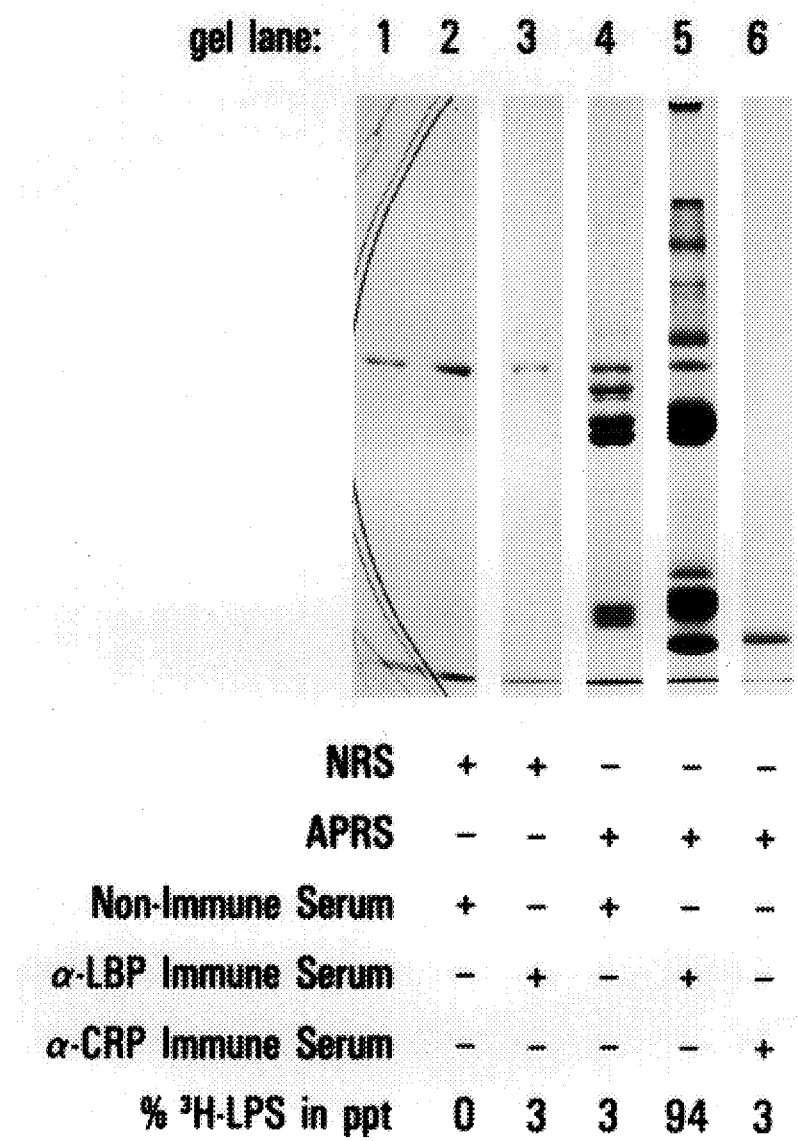

FIG. 15 shows SDS-PAGE analyses of and quantitation of $^3$H-LPS immunoprecipitates obtained from mixtures of APRS or NRS and anti-LBP antisera. Reaction mixtures and $^3$H-LPS precipitation are shown below SDS-PAGE gel lanes. Lane 6 contained CRP.

Figure 16:
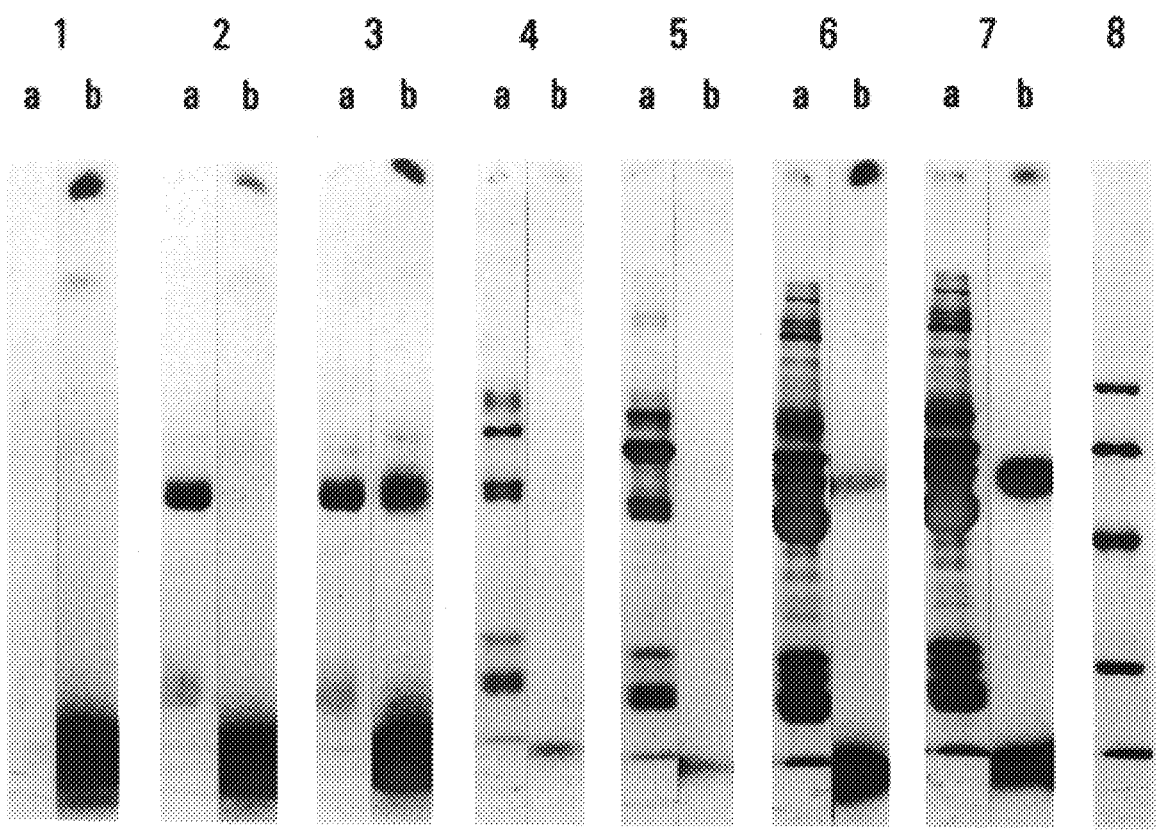

FIG. 16 illustrates SDS-PAGE analysis of $^{125}$I-ASD-LPS reaction mixtures. Lanes 1–3 contained samples of the reaction mixtures in which samples were applied directly to the gels. Lanes 4–7 contained immunoprecipitates of the reaction mixtures precipitated with 14% (v/v) anti-LBP antiserum. Each pair of lanes, a and b, represents the Coomaassie Blue stained gel and the autoradiographic print, respectively. Lane 1, $^{125}$I-ASD-LPS; lane 2, $^{125}$I-ASD- LPS pre-photolysed and then admixed with immunopurified anti-LPS; lane 3, $^{125}$I-ASD-LPS photolysed with immunopurified anti-LPS; lane 4, pre-photolysed $^{125}$I-ASD-LPS with NRS; lane 5, $^{125}$I-ASD-LPS photolysed with NRS; lane 6 pre-photolysed $^{125}$I-ASD-LPS with APRS; lane 7, $^{125}$I-ASD-LPS admixed with APRS; and lane 8, molecular weight markers, 94 kD, 43 kD, 30 kD.

FIG. 17 shows the single-letter amino acid residue sequence, from left to right and in the direction from amino-terminus to carboxy-terminus, of lapine LBP from the amino-terminus of the leader sequence peptide through the carboxy-terminus of the protein. The vertical line between residues 26 and 27 indicates that the mature protein begins at residue position 27.

FIG. 18 shows the DNA coding sequence for lapine LBP, from the 5'-terminus toward the 3'-terminus.

FIG. 19 shows the single-letter amino acid residue sequence, from left to right and in the direction from amino-terminus to carboxy-terminus, of human LBP from the amino-terminus of the leader sequence peptide through the carboxy-terminus of the protein. The vertical line between residues 25 and 26 indicates that the mature protein begins at residue position 26.

FIG. 20 shows the DNA coding sequence for human LBP, from the 5'-terminus toward the 3'-terminus.

DETAILED DESCRIPTION OF THE INVENTION

I. INTRODUCTION

The present invention contemplates a lipopolysaccharide binding protein (LBP), and an assay using LBP for the presence of LPS in an animal host that is susceptible of Gram-negative bacterial infection, as well as polypeptides and antibodies.

This invention relates to the finding that a glycoprotein present in acute phase serum, but substantially absent from normal serum retards the binding of lipopolysaccharide endotoxins to the high density lipoprotein present in blood serum.

During the first few days following an insult to an animal, a vast number of systemic and metabolic changes occur that are referred to as the acute phase response. Kushner (1982) Ann. N. Y. Acad. Sci. 389:39. Insults leading to an acute phase response include tissue-injuring infection, surgical or other trauma, drug-related effects, burns, tissue infarction and various idiopathic inflammatory states.

The liver is particularly affected during the acute phase response, and causes a rise in concentration of a large number of plasma proteins that have been grouped together as acute phase plasma proteins. Proteins whose concentrations rise by as much as 25 percent have been included in the group of acute phase plasma proteins.

The best studied acute phase proteins rise in concentration still more. Among those proteins are ceruloplasmin and complement component C3 whose concentrations increase by about 50 percent; alpha$_1$- acid glycoprotein, alpha$_1$-antitrypsin, alpha$_1$-antichymotrypsin, fibrinogen and haptoglobin whose concentrations increase about two to about four fold; and C-reactive protein (CRP) and serum amyloid A protein (SAA) whose concentrations usually increase several hundred times.

Serum obtained from an animal in an acute phase response is referred to as acute phase serum (APS). Animals that are free from infection, or tissue injury as described before are referred to as normal animals. Serum from such a normal animal is referred to as normal serum (NS).

II. THE GLYCOPROTEIN AND ITS USES

A. The Binding Protein and Assay

The compositions and methods of the present invention utilize a purified binding protein that is often referred to herein as lipopolysaccharide binding protein (LBP). LBP is often referred to herein as a "glycoprotein" even though it is useful in non-glycosylated form as obtained, for example, by recombinant techniques from E. coli.

Non-glycosylated LBP is useful in several ways, including as a control antigen in a LBP immunoassay using antibodies raised to a purified LBP or a polypeptide described herein, as well as for raising antibodies that immunoreact with purified LBP obtained from humans, rabbits or the like.

The terms "purified glycoprotein" or "purified binding protein" are used herein to mean that the protein (LBP) moves as a single band in SDS-PAGE analysis. Preferably, the purified protein contains no more than about 30 weight percent of other proteinaceous material that is stainable by Coomassie blue, more preferably no more than about 20 weight percent of such other material, and most preferably no more than about 10 weight percent of such other material. The protein is thus substantially homogeneous. The foregoing percentages are based on the total weight of proteinaceous material present in the single band.

The binding protein is present in impure form in acute phase serum (APS) of animals susceptible to infection by Gram-negative lipopolysaccharide-secreting bacterial infections. In humans, the impure glycoprotein is present in an amount of about 5 to about 10 micrograms per milliliter (ug/ml) of APS, whereas in rabbits, impure LBP is present in an amount of about 10–50 ug/ml.

The glycoprotein is substantially absent from normal serum (NS) of such animals. By "substantially absent", it is meant that less than about 0.5 ug/ml of the glycoprotein is present in such sera.

Since the concentration of the useful, but impure glycoprotein rises many-fold from substantial absence in NS to an identifiable presence in APS, the useful glycoprotein can be classed as an acute phase protein, as discussed hereinbefore.

The useful purified glycoprotein can be further identified by its binding to LPS secreted by Gram-negative bacteria; i.e., complex formation, when the purified glycoprotein and LPS are admixed in vitro in a normal animal serum (e.g., a non-acute phase serum) such as that of an animal host to be treated, as is discussed hereinafter. The binding of the glycoprotein to LPS; i.e., complex formation, can be assayed in several ways as is also discussed hereinafter. However, the centrifugation density gradient method described hereinafter and in Tobias and Ulevitch (1983) J. Immunol. 131:1913, whose disclosures are incorporated by reference, is preferred. The LBP-LPS complex so formed has a density of 1.3 g/cc.

The purified glycoprotein, also retards the in vitro binding of LPS to high density lipoprotein (HDL) that is present in a normal animal serum. Again, the method of determining the binding rate retardation caused by the glycoprotein can be assessed in several manners. However, the centrifugation density gradient technique that assesses rates of density shifts from 1.33 (LPS alone) or 1.30 (LBP-LPS complex) to less than 1.2 g/cc (LPS-HDL) described in Tobias and Ulevitch (1983) J. Immunol. 131:1913 is preferred.

The purified glycoprotein, while being pure relative to other proteins and glycoproteins generally, is also substantially free from other acute phase proteins such as those mentioned hereinbefore. Particularly absent are CRP, SAA, murine serum glycoprotein gp70 and their homologs obtained from other animal species.

Still further, antibodies raised to the 39-residue polypeptide, or to shorter polypeptides as described hereinafter, immunoreact with LBP in glycosylated or non-glycosylated forms. That immunoreaction takes place at least when the LBP molecule is in denatured form as when treated with 2-mercaptoethanol in SDS-PAGE analysis. Most preferably, those antibodies immunoreact with human, lapine and other LBP molecules (homologs) in denatured and non-denatured forms, and whether the molecule is glycosylated or non-glycosylated.

The purified glycoprotein has a molecular weight of about 55,000 to about 70,000 daltons. Exemplary of such materials are the lapine glycoprotein having an apparent relative molecular weight of about 60,000 daltons and the human glycoprotein having an apparent relative molecular weight of about 59,500 daltons when glycosylated, and about 53,000 daltons when expressed as a recombinant without glycosylation, both of which are discussed further hereinafter. Apparent relative molecular weights (masses), "$M_r$" are hereinafter referred to as "molecular weights" or "molecular masses".

It was previously believed that the useful human glycoprotein was the material first reported by Iwasaki and Schmid (1970) J. Biol. Chem. 245:1814 and later noted by Schwick and Haupt, Chapter 3, "Human Plasma Proteins of Unknown Function", in The Plasma Proteins IV, Academic Press, Inc. (1984) page 196, both of which disclosures are hereby incorporated by reference. Amino acid and carbohydrate analyses of that glycoprotein are provided in Table II, whereas further physical properties and solubilities in various media are found in Table I of the Iwasaki and Schmid paper. This belief was erroneous. LBP is now believed to be a newly discovered glycoprotein with only some characteristics similar to those of the material reported by the above authors.

As can be seen from a comparison of the numbers of amino acids per molecule of both proteins, human LBP and the $alpha_2$, $beta_1$-glycoprotein of Iwasaki and Schmid, shown in Table I below, are not the same proteins. A similar comparison of the amino acids per molecule of the $alpha_2$, $beta_1$- glycoprotein and the lapine LBP shows that those two proteins are too dissimilar to be homologs.

TABLE I

Comparison of Amino Acid Composition of
$Alpha_2$-$Beta_1$-Glycoprotein and LBP[1]-$Alpha_2$-$Beta_1$-

| Amino Acid | Glycoprotein[2] | LBP |
| --- | --- | --- |
| Alanine | 25.1 | 30.0 |
| Arginine | 9.1 | 22.0 |
| Asparagine | — | 21.0 |
| Aspartic Acid | 46.2 | 22.0 |
| Cysteine | — | 4.0 |
| Half Cysteine | 11.7 | — |
| Glutamine | — | 18.0 |
| Glutamic Acid | 46.2 | 24.0 |
| Glycine | 19.1 | 28.0 |
| Histadine | 5.0 | 10.0 |
| Isolencine | 19.9 | 24.0 |
| Leucine | 32.2 | 71.0 |
| Lysine | 22.7 | 22.0 |
| Methionine | 3.3 | 10.0 |

TABLE I-continued

Comparison of Amino Acid Composition of
Alpha$_2$-Beta$_1$-Glycoprotein and LBP[1]-Alpha$_2$-Beta$_1$-

| Amino Acid | Glycoprotein[2] | LBP |
|---|---|---|
| Phenylalanine | 15.7 | 25.0 |
| Proline | 28.9 | 27.0 |
| Serine | 21.1 | 48.0 |
| Threonine | 27.7 | 21.0 |
| Tryptophan | 8.4 | 2.0 |
| Tyrosine | 13.9 | 16.0 |
| Valine | 30.1 | 32.0 |
| No. of Residues | 386.3 | 477.0 |

[1]Values are stated as number of residues/molecule of protein.
[2]Data from Iwasaki and Schmid (1970) J. Biol. Chem., 245: 1814.

Since the useful glycoprotein is not alpha$_2$, beta$_1$-glycoprotein, it is believed to be a newly identified glycoprotein, lipopolysaccharide binding protein (LBP).

Several studies have reported homologies among the acute phase serum proteins across many animal species. See, for example Baltz et al. (1982) *Ann. N.Y. Acad. Sci.* 389:49 as to phylogenetic aspects of CRP and serum amyloid P component (SAP).

It is believed from the concentrations of the glycoprotein in human, and rabbit sera; the formation of complexes having a density of 1.3 g/cc in APS of humans, rabbits and mice that respond to LPS; the observed binding retardation between LPS and HDL shown in rabbits and humans; and the before-mentioned acute phase serum protein homologies, that a protein homologous to LBP is present in all animals that are susceptible or respond to LPS and can mount an acute phase response.

A recent paper [Tobias et al. (1988) *J. Biol. Chem.*, 263:(27):13479] discussed LBP in relation to a family of LPS binding proteins, and particularly a protein referred to as bactericidal/permeability increasing protein (BPI). BPI was shown in that paper to immunocross-react with antibodies to LBP and to share some sequence identities and homologes to LBP, as well as bind to LPS to form a complex having a density of 1.29 g/cc.

However, the LPS-BPI complex does not dissociate in the presence of HDL to form a LPS-HDL complex. In addition, BPI kills Grain-negative bacteria, whereas LBP exhibits no bactericidal effects under similar conditions. Still further, LBP is a product of hepatocytes, whereas BPI is a product of neutrophils.

Thus, LBP and BPI are different proteins. Similarly, LBP also appears to differ from other, known, LPS binding proteins.

B. Assay Methods

The purified glycoprotein described before is also useful in assay methods for the presence of lipopolysaccharide endotoxin secreted by Gram-negative bacteria in a liquid animal body sample or other aqueous sample that may be contaminated by LPS. Exemplary liquid animal body samples include blood, serum, plasma, abdominal exudate, saliva, urine, cerebrospinal fluid, tears and joint fluid. Serum and plasma are preferred liquid animal body samples.

In accordance with this method, an aliquot of a liquid animal body sample is provided, and is admixed with an endotoxin unmasking reagent to unmask any endotoxin present in the sample aliquot and form a liquid aliquot containing unmasked endotoxin.

Unmasking reagents and techniques for their use are described in U.S. Pat. No. 4,276,050 to Firca and Rudbach whose teachings are incorporated by reference. Briefly, exemplary unmasking reagents include aqueous solutions containing 2 percent Tween-80 [polyoxyethylene (20) sorbitan monooleate], 2 percent dextransulfate, 3 percent sodium chloride, 2 percent ammonium thiocyanate, and most preferably 0.002 molar benzamidine and its biologically compatible acid addition salts. The unmasking reagent is preferably admixed with about an equal volume of body sample aliquot, and the composition is agitated gently.

The unmasked endotoxin-containing body sample aliquot is thereafter admixed with a before-described glycoprotein to form an admixture. The admixture so formed is maintained for a predetermined time period sufficient for the purified glycoprotein to react and form a complex with lipopolysaccharide endotoxin present in the body sample; an exemplary time period being about 10 minutes. As is well known in the art, the maintenance or incubation time is a function, inter alia, of the amounts of both materials that are present in the admixture, e.g., LPS and glycoprotein (LBP), with lower amounts typically requiring longer maintenance times. Maintenance times of about 5 minutes to about 3 hours are exemplary, with about 10 to about 30 minutes being more usual.

The presence of the complex formed between the admixed, purified glycoprotein and lipopolysaccharide endotoxin is determined. The admixed, purified glycoprotein preferably includes a covalently-linked label that provides a means for indicating the formation of the complex, and preferably the amount of complex formed.

Exemplary of such covalently-linked labels are radioisotopes such as $^3$H and $^{125}$I whose methods of covalent linkage to proteins are well known.

The discussion hereinafter in Section III relates primarily to formation of LPS/glycoprotein complexes in which the LPS bears a radiolabel ($^3$H) and in which the complex formation was assessed by measuring radioactivity in various fractions taken following CsCl density gradient centrifugation. Similar assays can be performed using modifications of the above method in which the admixed glycoprotein contains the radiolabel.

Enzyme labels and their substrates can also be used. Exemplary enzymes and substrates include horseradish peroxidase normally used with hydrogen peroxide and an oxidative dye precursor such as o- phenylenediamine and alkaline phosphatase that is typically used with p-nitrophenyl phosphate. Methods for covalently linking enzymes to proteins are also well known in the art.

Substantially any assay method similar to those receptor-ligand assays used in immunological tests between antibody and antigen is also useful herein. Particularly preferred receptor-ligand assays are solid phase assays.

Thus, in one method, a known amount of LPS as ligand is affixed to a solid matrix as a solid phase support. The liquid body sample aliquot and a known, excess amount of the purified, labeled glycoprotein over that of any amount of LPS expected in the sample are admixed to form a liquid phase admixture, and the liquid phase admixture is maintained as described before for a time sufficient for the purified, labeled glycoprotein to react and complex with LPS present in the body sample. An unmasking agent is preferably admixed with the body sample prior to admixture of the body sample and purified glycoprotein.

The maintained liquid phase admixture is then admixed with the solid phase to form a solid/liquid phase admixture. That admixture is maintained for a further time period sufficient for a further complex to form between the LPS of the solid phase support and the excess glycoprotein that did not bind with LPS present in the body sample. Separation of the phases and determination of the amount of solid phase-bound, labeled glycoprotein provides a measure of the amount of LPS in the aliquot and therefore in the body sample.

It is to be understood that the glycoprotein can also be used as the solid phase-affixed portion and a known amount of labeled LPS can be added to the body sample aliquot.

It is often convenient to augment the amount of LPS originally present in the body sample. This can conveniently be done by culturing the body sample in a culture medium that promotes growth of Gram-negative bacteria that produce the LPS and are present in the sample. After a suitable growth period such as one or two days, the culture medium is concentrated to provide a concentration of solids having a molecular weight greater than about 10,000 of at least about one milligram per milliliter. The aliquot can then be provided from the concentrated culture medium.

The amount of LPS present in the liquid body sample can also frequently be augmented by concentrating the sample or its aliquot prior to use in the method. Convenient methods for performing such concentrations include air drying and lyophilization followed by redissolution in a smaller amount of solvent than the original volume, and ultrafiltration as described in Section V F. Ultrafiltration removes many unwanted salts and low molecular weight species.

Useful solid matrices are well known in the art. Such materials include the cross-linked dextran available under the trademark SEPHADEX from Pharmacia Fine Chemicals (Piscataway, N.J.), agarose, beads of glass, polyvinyl chloride, polystyrene, cross-linked acrylamide, nitrocellulose or nylon-based webs such as sheets or strips, or the wells of a microtiter plate such as those made from polystyrene or polyvinyl chloride.

Latex particles useful in agglutination-type assays are also useful solid matrices. Such materials are supplied by the Japan Synthetic Rubber Company of Tokyo, Japan, and are described as carboxy-functional particles dispersed in an anionic soap. Typical lots of such particles have an average diameter of 0.308 microns, and may have an average carboxy-functional group distribution of about 15 to about 30 square Angstroms per carboxy group.

Prior to use, the particles are reacted with a diamine such as 1,3-diamino-2-propanol to form a plurality of amide bonds with the particle carboxy groups while maintaining free amine groups. The free amines are thereafter reacted with a dialdehyde such as glutaraldehyde and the glycoprotein to form Schiff base reaction products. The Schiff base reaction products are thereafter reduced with a water-soluble reductant such as sodium borohydride to provide a useful solid support.

C. LBP Polypeptides and Antibodies

The discussion that follows in Section IV describes work with the lapine (rabbit) homolog of the human glycoprotein (LBP) discussed earlier herein and in the following Section III. The studies described in Section IV particularly describe the amino-terminal thirty-nine residues of lapine LBP.

A synthetic polypeptide that consists essentially of 6 to about 39 amino acid residues, and more preferably about 10 to about 25 amino acid residues, corresponding to all or a portion of those 39 amino-terminal residues of rabbit (lapine) LBP constitutes another aspect of the present invention. The complete amino-terminal lapine LBP 39-residue sequence of the mature protein, from left to right and in the direction from amino-terminus to carboxy-terminus, is shown below. This polypeptide is referred to as polypeptide A.

Thr—Asn—Pro—Gly—Leu—Ile—Thr—Arg—Ile—Thr—
Asp—Lys—Gly—Leu—Glu—Tyr—Ala—Ala—Arg—Glu—
Gly—Leu—Leu—Ala—Leu—Gln—Arg—Lys—Leu—XXX—
Gly—Val—Thr—Leu—Pro—Asp—Phe—Asp—Gly wherein the residue denominated XXX is indeterminate, and believed to be an asparagine (Asn) residue. A synthetic polypeptide of this invention corresponding in sequence to a portion of the amino- terminal 39 residues of lapine LBP that includes position 30 with its indeterminate residue (XXX) includes an Asn residue at that position.

Using a sequenator, the residue at position 30 of the mature lapine LBP could not be positively identified and was thought to be asparigine (Asn). However, translation of the genetic code in the sample used by Dr. Ralf Schumann, the residue at position 30 was determined to be leucine (Leu). Similarly, the residue at position 37 was found to be phenylalanine (Phe) using the sequenator and serine (Ser) by translation of the genome. The reasons for finding these differences are unknown and could be due to genetic variations among the rabbits utilized in the studies.

Although the above differences are not conservative, as discussed hereinafter, antibodies raised to one polypeptide cross-react with the other polypeptide, as well as reacting with LBP from any source.

Exemplary synthetic polypeptides containing 6 to about 39 residues include those having the sequences shown below, from left to right and in the direction from amino-terminus to carboxy-terminus, (1–6) Thr-Asn-Pro-Gly-Ile-Thr;

(7–13) Thr-Arg-Ile-Thr-Asp-Lys-Gly;

(1–29) Thr-Asn-Pro-Gly-Leu-Ile-Thr-Arg-Ile-Thr Asp-Lys-Gly-Leu-Glu-Tyr-Ala-Ala-Arg-Glu-Gly-Leu-Leu-Ala Leu-Gln-Arg-Lys-Leu; and (1–39) as already shown, wherein "XXX" is asparagine (Asn) or Leucine (Leu) and the residue at position 37 is phenylalanine (Phe) or serine (Ser).

Exemplary more preferred synthetic polypeptides having about 10 to about 25 residues that correspond in sequence to a portion of the amino- terminal 39 residue sequence of the lapine LBP molecule, from left to right and in the direction from amino-terminus to carboxy-terminus, are shown below.

(1–13) Thr-Asn-Pro-Gly-Leu-Ile-Thr-Arg-Ile Thr-Asp-Lys-Gly;

(8–21) Arg-Ile-Thr-Asp-Lys-Gly-Leu-Glu-Tyr-Ala-Ala-Arg-Glu-Gly;

(8–29) Arg-Ile-Thr-Asp-Lys-Gly-Leu-Glu-Tyr-Ala-Ala-Arg-Glu-Gly-Leu-Leu-Ala-Gln-Arg-Lys-Leu; and (26–39) Gln-Arg-Lys-Leu-Asn(Leu)-Gly-Val-Thr-Leu-Pro-Asp-Phe(Ser)-Asp-Gly, wherein the parenthesized amino acid residues are each independently alternative to the immediately preceding residues in the sequence.

The parenthesized numerals before the two sets of polypeptide sequences above refer to the numbered positions from the amino-terminus of LBP to which those polypeptides correspond.

Prior to obtaining the DNA sequences for either the human or lapine LBP molecules, a sequence for the amino-terminal portion of human LBP was determined using the human protein isolated as described herein. This human LBP sequence was obtained as described for the lapine protein and was utilized to confirm the sequence of recombinant DNA molecule discussed hereinafter.

The amino acid residue sequence of the mature human LBP molecule defines a further polypeptide of this invention referred to herein as polypeptide C. The sequence of polypeptide C is shown below:

C: Ala-Asn-Pro-Gly-Leu-Val-Ala-Arg-Ile-Thr-Asp-Lys-Gly-Leu-Gln-Tyr-Ala-Ala-Gln-Glu

As can be seen by comparison to the sequences of polypeptides A and B, the sequences of all three polypeptides are homologous and nearly identical.

A polypeptide consisting essentially of 6 to about the entire 20-mer sequence of polypeptide C constitutes a further polypeptide of this invention, with a polypeptide having a length of about 10 to about 20 residues being preferred. Exemplary polypeptides are listed below, shown as discussed previously and with parenthesized numerals having the meaning discussed above as applied to human LBP.

(1–6) Ala-Asn-Pro-Gly-Leu-Val
(5–12) Leu-Val-Ala-Arg-Ile-Thr-Asp-Lys
(2–15) Asn-Pro-Gly-Leu-Val-Ala-Arg-Ile-Thr-Asp-Lys-Gly-Leu-Gln
(5–19) Leu-Val-Ala-Arg-Ile-Thr-Asp-Lys-Gly-Leu-Gln-Tyr-Ala-Ala-Gln
(1–18) Ala-Asn-Pro-Gly-Leu-Val-Ala-Arg-Ile-Thr-Asn-Lys-Gly-Leu-Gln-Tyr-Ala-Ala

The full names for individual amino acid residues are sometimes used herein as are the well-known three-letter abbreviations. Single-letter abbreviations (code) are also utilized. The Table of Correspondence, below, provides the full name as well as the three-letter and single-letter abbreviations for each amino acid residue named herein [See, for example, L. Stryer, *Biochemistry,* 2nd ed., W. H. Freeman and Company, San Francisco, (1981), page 16.]. The amino acid residues utilized herein are in the natural, L, form unless otherwise stated.

Table of Correspondence

| Amino acid | Three-letter abbreviation | One-letter symbol |
|---|---|---|
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The term "corresponds" in its various grammatical forms is used herein and in the claims in relation to polypeptide sequences to mean the polypeptide sequence described containing only conservative substitutions in particular amino acid residues along the polypeptide sequence. In addition, one polypeptide "corresponds" to another if antibodies raised to one polypeptide immunoreact with the other polypeptide.

The term "conservative substitution" as used above is meant to denote that one amino acid residue has been replaced by another, biologically similar residue. Examples of conservative substitutions include the substitution of one hydrophobic residue such as Ile, Val, Leu or Met for another, or the substitution of one polar residue for another such as between Arg and Lys, between Glu and Asp or between Gln and Asn, and the like.

In some instances, the replacement of an ionic residue by an oppositely charged ionic residue such as Asp by Lys has been termed conservative in the art in that those ionic groups are thought to merely provide solubility assistance. In general, however, since the replacements discussed herein are on relatively short synthetic polypeptide antigens, as compared to a whole protein, replacement of an ionic residue by another ionic residue of opposite charge is considered herein to be "radical replacement", as are replacements between nonionic and ionic residues, and bulky residues such as Phe, Tyr or Trp and less bulky residues such as Gly, Ile and Val.

The terms "nonionic" and "ionic" residues are used herein in their usual sense to designate those amino acid residues that normally either bear no charge or normally bear a charge, respectively, at physiological pH values. Exemplary nonionic residues include Thr and Gln, while exemplary ionic residues include Arg and Asp.

A synthetic polypeptide of the present invention can be prepared by several solid and liquid phase techniques as are well known in the art. Preferably, however, the solid phase so-called "Merrifield" method is utilized. Exemplary syntheses are discussed in U.S. Pat. No. 4,545,931 and No. 4,544,500, whose disclosures are incorporated herein by reference.

A polypeptide of the present invention is preferably linked to an immunogenic carrier such as a protein as a conjugate for use in production of antibodies and antibody preparations. Immunogenic carriers are well known in the art and include keyhole limpet hemocyanin (KLH), edestin, curcubin, human serum albumin, tetanus toxoid, sheep erythrocytes, polyamino acids such as poly(D-lysine D-glutamic acid) and the like.

Methods of linking the polypeptide to the immunogenic carrier to form the conjugate are also well known. Exemplary techniques include use of glutaraldehyde, a water-soluble carbodiimide, and those described in U.S. Pat. No. 4,544,500 and No. 4,545,931.

The polypeptide-carrier conjugate is dissolved or dispersed in an aqueous composition of a physiologically tolerable diluent when used to induce the production of antibodies. Suitable physiologically tolerable diluents are well known in the art and include phosphate-buffered saline (PBS) and 0.9 normal saline, and preferably also include an adjuvant such as complete Freund's adjuvant or incomplete Freund's adjuvant.

An effective amount of a conjugate-containing composition is introduced into a host animal such as a goat, rabbit, mouse, rat, horse or the like to induce the production (secretion) of antibodies to the polypeptide. Effective amounts of immunogens useful for inducing antibody secretions in host animals are well known in the art. Methods of introduction into the host animal are also well known and are typically carried out by parenteral administration as by injection. A plurality of such introductions is normally utilized so that the host is hyperimmunized to the immunogenic polypeptide-containing conjugate. For example, weekly introductions over a one-to-two-month time period can be utilized until a desired anti-polypeptide antibody titer is achieved.

The antibodies so induced are thereafter recovered from the host animal. The recovered antibodies can be utilized as a preparation in the host serum as recovered, or can be in substantially pure form; i.e., substantially free from host serum proteins, polypeptides and cellular debris. The latter antibody preparation can be conveniently prepared by passage of the recovered serum over an affinity column as prepared from Sepharose 4B (Pharmacia Fine Chemicals, Piscataway N.J.) linked to the polypeptide of the conjugate, as is known.

The recovered preparation of antibodies immunoreacts with a synthetic polypeptide of the invention, such as the polypeptide of the conjugate, as well as with denatured rabbit or human LBP. Exemplary denatured LBP is that material that has been treated with 2-mercaptoethanol in SDS-PAGE analysis, and typically has a protein structure that is relatively more open or expanded than is that of native protein. In more preferred practice, the antibodies also immunoreact with native, non-denatured rabbit LBP as is present in APRS. Most preferably, the antibodies immunoreact with human LBP in denatured and/or non-denatured forms. Those immunoreactions occur whether the LBP molecule is glycosylated or non-glycosylated.

An antibody preparation of this invention prepared from a polypeptide as described above can be in dry form as obtained by lyophilization. However, the antibodies are normally used and supplied in an aqueous liquid composition in serum or a suitable buffer such as PBS.

The antibodies and polypeptides described herein are useful in assay methods for the determination of the presence and amount of rabbit and human lipopolysaccharide binding protein (LBP).

The polypeptides are particularly useful in these assays for blocking studies as in connection with the Western blot-type assays. Similar blocking can also be carried out in solid phase assays such as the ELISA-type studies that are also described hereinafter.

The antibodies are particularly useful in assays because of their unique specificity for immunoreacting with LBP. For example, a liquid body sample as described before can be admixed and contacted with the antibodies affixed to a solid matrix as a solid support to form a solid/liquid phase admixture. After passage of a predetermined maintenance time for the contact, the phases are separated to remove any materials that did not immunoreact. The non- immunoreacted antibodies are thereafter visualized or otherwise assayed as with a label linked to a polypeptide of this invention.

Solid phase assays, such as enzyme-linked immunosorbant assays (ELISA), radio-labeled immunosorbant assays (RIA) or flurochrome-linked immunosorbant assays (FIA) are particularly contemplated.

Thus, the amount of LBP present in a liquid body sample is assayed in an embodiment of this invention. Here, a solid phase matrix such as the sides and bottom of a polystyrene or polyvinylchloride microtiter plate is provided. Antibodies of this invention are affixed to the solid matrix as by physical binding to form a solid phase support, as is known.

A predetermined amount of a liquid body sample such as plasma or serum to be assayed for LBP is admixed with the solid phase support to form a solid/liquid admixture. Exemplary predetermined amounts typically are about 25 to about 150 microliters neat, or more preferably present at a known dilution in an aqueous medium such as PBS that contains a total volume of about 25 to about 150 microliters.

That solid/liquid admixture is maintained for a period of time sufficient for LBP present in the sample to immunoreact with the solid phase-affixed antibody to form a solid phase-bound immunoreactant, and a liquid phase depleted of LBP. Exemplary maintenance (incubation) times typically range from about 5 minutes to about 6 hours, with the temperature of that maintenance typically being from about 4° C. to about 40° C., with room temperature (about 20° C.) being exemplary.

The solid and liquid phases are then separated as by rinsing to remove any materials from the sample that were not bound to the solid support. The solid phase containing the bound immunoreactant is retained for further use in the assay.

The amount of solid phase-bound immunoreactant formed is then determined, and thereby determines the amount of LBP present in the assayed sample. That amount can be determined in a number of well known manners.

For example, where the amount of antibodies affixed to the solid matrix is known, an aqueous composition containing a polypeptide of this invention operably linked to a label (labeling means) can be immunoreacted with the unreacted affixed antibodies to form a second solid/liquid phase admixture.

The second solid/liquid phase admixture is maintained for a second time period sufficient for the labeled polypeptide to immunoreact with the previously unreacted solid phase-bound antibodies and form a second solid phase-bound immunoreactant. Maintenance times and temperatures useful for this maintenance step are similar to those described before.

The solid and liquid phases are again separated to remove any labeled polypeptide not present in the second solid phase-bound immunoreactant, and the amount of labeled polypeptides bound is determined. That determination is conveniently accomplished by use of a label such as an enzyme, flurochrome dye or a radiolabel operably linked to the second antibodies. To obtain the most accurate results in such assays, it is preferred that non-specific binding sites on the solid supports be blocked after the solid support is prepared. Such non-specific site blockage can be achieved by known techniques such as by admixture of an aqueous composition of a protein free from immunoreaction in the assay such as bovine serum albumin (BSA) with the solid support prior to admixture of the liquid body sample. The admixture so formed is typically maintained for the time period and at the temperature described before. The solid phase having its non-specific binding sites blocked and the liquid phase are then separated as by rinsing, and the liquid body sample is admixed.

The discussion above has included a label operably linked to a polypeptide. The term "operably linked" is used herein to mean that the label molecules are linked or bonded to the polypeptide molecules so that antibody binding of the polypeptide is not substantially impaired nor is the action of the label substantially impaired. Thus, polypeptides containing operably linked label molecules bind to their antibodies and the linked label molecules operate to indicate the presence of the bound polypeptide in the immunoreactant.

For an ELISA, typically used enzymes operably linked to a polypeptide as a label include horseradish peroxidase, alkaline phosphatase and the like. Each of those enzymes is used with a color-forming reagent or reagents (substrate) such as hydrogen peroxide and o- phenylenediamine; and p-nitrophenyl phosphate, respectively.

Similar assays can also be carried out using a fluorochrome dye operably linked to a polypeptide as a label to signal the presence of polypeptides bound in an immunoreaction product. The fluorochrome dye is typically linked by means of an isothiocyanate group to form the conjugate. Exemplary fluorochrome dyes include fluorescein isothiocyanate (FITC), rhodamine B isothiocyanate (RITC) and tetramethylrhodamine isothiocyanate (TRITC).

In another technique, biotin operably linked to an a polypeptide is utilized as a label to signal the presence of the immunoreactant in conjunction with avidin that is itself linked to a signalling means such as horseradish peroxidase.

A radioactive element such as $^3$H or $^{125}$I as utilized herein can also be operably linked to the polypeptide to form the label. In this instance, the radioactive decay of the element serves to quantify the assay of bound polypeptide, and thereby bound LBP.

D. Recombinant LBP

1. DNA Segments

In living organisms, the amino acid residue sequence of a protein or polypeptide is directly related via the genetic code to the deoxyribonucleic acid (DNA) sequence of the structural gene that codes for the protein. Thus, a structural gene can be defined in terms of the amino acid residue sequence, i.e., protein or polypeptide, for which it codes.

An important and well known feature of the genetic code is its redundancy. That is, for most of the amino acids used to make proteins, more than one coding nucleotide triplet (codon) can code for or designate a particular amino acid residue. Therefore, a number of different nucleotide sequences, both RNA and DNA, can code for a particular amino acid residue sequence. Such nucleotide sequences are considered functionally equivalent since they can result in the production of the same amino acid residue sequence in all organisms. Occasionally, a methylated variant of a purine or pyrimidine may be incorporated into a given nucleotide sequence. However, such methylations do not affect the coding relationship in any way.

The DNA segments of the present invention are characterized as including a DNA sequence that encodes a lipopolysaccharide binding protein such as the human and lapine homologs. In preferred embodiments, the DNA segment includes a DNA sequence that encodes a LBP precursor protein (pre-LBP) that includes the amino-terminal leader or signal sequence. That is, the DNA segments of the present invention are characterized by the presence of a LBP or a pre-LBP, structural gene. Preferably, the gene is present as an uninterrupted linear series of codons where each codon codes for an amino acid residue found in LBP or pre-LBP protein, i.e., a gene free of introns.

Thus, a DNA segment consisting essentially of the sequence shown in FIGS. 18 or 20 from about position 1 at its 5'-terminus to about position 1446 in FIG. 18 and 1431 in FIG. 20 at its 3'-terminus, and capable of expressing pre-LBP constitutes one embodiment of the present invention. A DNA segment consisting essentially of the sequence shown in FIGS. 18 or 20 from about position 79 to about position 1446 in FIG. 18 and from about position 76 to about position 1431 in FIG. 20, and capable of expressing pre-LBP constitutes another embodiment of the invention.

Homologous DNA and RNA sequences that encode the above LBP and pre-LBP proteins are also contemplated, as discussed before.

DNA segments that encode LBP and pre-LBP proteins can easily be synthesized by chemical techniques, for example, the phosphotriester method of Matteucci et al., *J. Am. Chem. Soc.,* 103:3185 (1981). (The disclosures of the art cited herein are incorporated herein by reference.) Of course, by chemically synthesizing the coding sequence, any desired modifications can be made simply by substituting the appropriate bases for those encoding the native amino acid residue sequence. However, DNA molecules including sequences exactly homologous to those shown in FIGS. 18 and 20 are preferred. Furthermore, DNA segments consisting essentially of structural genes encoding LBP and pre-LBP proteins can be obtained from recombinant DNA molecules containing those genes.

A DNA segment that includes a DNA sequence encoding LBP or pre-LBP can be prepared by operatively linking (ligating) appropriate restriction fragments from each of the above deposited plasmids using well known methods. The DNA molecules of the present invention produced in this manner typically have cohesive termini, i.e., "overhanging" single-stranded portions that extend beyond the double-stranded portion of the molecule. The presence of cohesive termini on the DNA molecules of the present invention is preferred.

2. Recombinant DNA Molecules

The recombinant DNA molecules of the present invention can be produced by operatively linking a vector to a DNA segment of the present invention.

As used herein, the term "vector" refers to a DNA molecule capable of autonomous replication in a cell and to which another DNA segment can be operatively linked so as to bring about replication of the attached segment. Vectors capable of directing the expression of LBP and pre-LBP genes are referred to herein as "expression vectors". Thus, a recombinant DNA molecule (rDNA) is a hybrid DNA molecule comprising at least two nucleotide sequences not normally found together in nature.

The choice of vector to which a DNA segment of the present invention is operatively linked depends directly, as is well known in the art, on the functional properties desired, e.g., protein expression, and the host cell to be transformed, these being limitations inherent in the art of constructing recombinant DNA molecules. However, a vector contemplated by the present invention is at least capable of directing the replication, and preferably also expression, of the LBP or pre-LBP structural genes included in DNA segments to which it is operatively linked.

In preferred embodiments, a vector contemplated by the present invention includes a procaryotic replicon, i.e., a DNA sequence having the ability to direct autonomous replication and maintenance of the recombinant DNA molecule extrachromosomally in a procaryotic host cell, such as a bacterial host cell, transformed therewith. Such replicons are well known in the art. In addition, those embodiments that include a procaryotic replicon also include a gene whose expression confers drug resistance to a bacterial host transformed therewith. Typical bacterial drug resistance genes are those that confer resistance to ampicillin or tetracycline.

Those vectors that include a procaryotic replicon can also include a procaryotic promoter capable of directing the expression (transcription and translation) of the LBP or pre-LBP genes in a bacterial host cell, such as *E. coli,* transformed therewith. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical of such vector plasmids are pUC8, pUC9, pBR322 and pBR329 available from Biorad Laboratories, (Richmond, Calif.) and pPL and pKK223 available from Pharmacia, Piscataway, N.J.

Expression vectors compatible with eucaryotic cells, preferably those compatible with vertebrate cells, can also be used to form the recombinant DNA molecules of the present invention. Eucaryotic cell expression vectors are well known in the art and are available from several commercial sources. Typically, such vectors are provided containing convenient restriction sites for insertion of the desired DNA segment. Typical of such vectors are pSVL and pKSV-10 (Pharmacia), pBPV-1/pML2d (International Biotechnologies, Inc.), and pTDT1 (ATCC, #31255).

In preferred embodiments, the eucaryotic cell expression vectors used to construct the recombinant DNA molecules of the present invention include a selection marker that is effective in an eucaryotic cell, preferably a drug resistance selection marker. A preferred drug resistance marker is the gene whose expression results in neomycin resistance, i.e., the neomycin phosphotransferase (neo) gene. Southern et al., *J. Mol. Appl. Genet.*, 1:327–341 (1982).

The use of retroviral expression vectors to form the rDNAs of the present invention is also contemplated. As used herein, the term "retroviral expression vector" refers to a DNA molecule that includes a promoter sequence derived from the long terminal repeat (LTR) region of a retrovirus genome.

In some preferred embodiments, the expression vector is typically a retroviral expression vector that is preferably replication-incompetent in eucaryotic cells. The construction and use of retroviral vectors has been described by Sorge et al., *Mol. Cell. Biol.*, 4:1730–37 (1984).

A variety of methods have been developed to operatively link DNA to vectors via complementary cohesive termini. For instance, complementary homopolymer tracts can be added to the DNA segment to be inserted and to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase or *E. coli* DNA polymerase I, enzymes that remove protruding, 3'-single-stranded termini with their 3',5'-exonucleolytic activities and fill in recessed 3'-ends with their polymerizing activities. The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies, Inc., New Haven, Conn.

Also contemplated by the present invention are RNA equivalents of the above described recombinant DNA molecules.

3. Recombinant LBP

Recombinant LBP (rLBP) prepared using the DNA segments and rDNA molecules as discussed before and illustrated hereinafter is also contemplated. Such rLBP molecules are prepared by use of a transcription vector transfected into a compatible procaryotic or eucaryotic host cell culture. Exemplary procaryotic cells are *E. coli* cells, whereas exemplary eurcaryotic cells include those of yeast such as *S. cerevisiae,* and more particularly mammalian cells such as CHO, COS, 3T3 and similar cells.

As is well known in the art, different cells require different media, growth conditions and vectors. However, those variations among cell types such as *E. coli, S. cerevisiae* and the different mammalian cells are all well known in the art, and workers of ordinary skill are well able to express proteins from the multitude of cell types once the structural gene is in hand.

rLBP having the sequence of the human or lapine homologs is particularly preferred herein. However, since all animals susceptible of infection by Gram-negative lipopolysaccharide-secreting bacteria are believed to have an impure LBP homolog in their sera during an acute phase reaction, other rLBP molecules are also contemplated. Such other rLBP molecules can be prepared using nucleic acid probes and antibodies as are discussed hereinafter.

An rLBP molecule can include the leader or signal peptide sequence as well as the mature molecule portion of LBP. For the lapine and human homologs, coding DNA sequences for both the pre-LBP and mature protein forms are shown in FIGS. 18 and 20, respectively. A rLBP molecule corresponding to the mature form of LBP is preferred.

A rLBP molecule can be glycosylated or not as is desired. For example, recombinant proteins prepared in *E. coli* are non-glycosylated, whereas proteins prepared by recombinant techniques in eurcaryotic cell hosts such as yeast or mammalian host cells are glycosylated, albeit the glycosylation differs between yeast and mammalian cell-produced recombinants.

rLBP preferably has all of the before-discussed biological activity of an LBP molecule. However, to be useful, a rLBP molecule need not have all of the biological activity such as binding to LPS and retarding LPS-HDL complex formation. Rather, all that is necessary for a rLBP molecule to be useful is that it immunoreact with antibodies raised to either purified LBP or a previously described polypeptide. More preferably, a rLBP molecule is capable of inducing antibodies that immunoreact with denatured or native human or lapine LBP. Most preferably, a rLBP molecule has all of the physical and biological properties of native, non-denatured LBP.

Transformation of appropriate cell hosts with a recombinant DNA molecule of the present invention is accomplished by well known methods that typically depend on the type of vector used. With regard to transformation of procaryotic host cells, see, for example, Cohen et al., *Proc. Natl. Acad. Sci. USA,* 69:2110 (1972); and Maniatis et al., *Molecular Cloning, A Laboratory Mammal,* Cold Spring Harbor Laboratory, Cold Spring Harbor, N.Y. (1982). With regard to transformation of vertebrate cells with retroviral vectors containing rDNAs, see, for example, Sorge et al., *Mol. Cell. Biol.,* 4:1730–37 (1984); Graham et al., *Virol.,* 52:456 (1973); and Wigler et al., *Proc. Natl. Acad. Sci. USA* 76:1373–76 (1979).

Successfully transformed cells, i.e., cells that contain a recombinant DNA molecule of the present invention, can be identified by well known techniques. For example, cells resulting from the introduction of an rDNA of the present invention can be cloned to produce monoclonal colonies. Cells from those colonies can be harvested, lysed and their DNA content examined for the presence of the rDNA using a method such as that described by Southern, *J. Mol. Biol.,* 98:503 (1975) or Berent et al., *Biotech.,* 3:208 (1985).

In addition to directly assaying for the presence of rDNA, successful transformation can be confirmed by well known immunological methods when the rDNA is capable of directing the expression of LBP or pre-LBP. For example, cells successfully transformed with an expression vector produce proteins displaying LBP or pre-LBP antigenicity. Samples of cells suspected of being transformed are harvested and assayed for LBP or pre-LBP using antibodies specific for those antigens, rabbit goat anti-rabbit antibodies, to LBP linked to horseradish peroxidase or FITC-conjugated antibodies.

Nutrient media useful for culturing transformed host cells are well known in the art and can be obtained from several commercial sources. In embodiments wherein the host cell is mammalian, a "serum-free" medium is preferably used.

III. LPS/HDL BINDING RETARDATION

As noted earlier, it was initially believed that a previously identified gp60 material isolated from acute phase rabbit serum (APRS) was responsible for the retardation of binding of rabbit HDL by exogenously supplied LPS. Tobias and Ulevitch (1983) *J. Immunol.* 131:1913. However, antibodies raised to the isolated gp60 when admixed with both NRS and APRS provided gp60-containing immunoreactants from both types of serum. The amounts of gp60 isolated from both serum types using those antibodies were similar. In addition, the isolated gp60, when reconstituted with NRS, provided a serum in which no retardation of LPS binding to HDL was observed.

Thus, it became apparent that the originally identified and isolated rabbit gp60 was not the material whose presence retards binding of LPS with HDL in rabbit sera. However, the original results that indicated the presence in APS of a material (i) that is substantially absent from NS (ii) that binds to gram-negative bacterially secreted lipopolysaccharide when both are admixed in vitro in normal serum, and (iii) retards the in vitro binding of LPS to HDL in serum is still thought to be correct, as is discussed hereinbelow.

Thus, further studies with the lapine system identified another protein of molecular weight of about 60,000 that is also glycosylated according to the periodic acid-Schiff stain. Preliminary data indicated that this glycoprotein is present in APRS in an amount of about 5–10 ug/ml, whereas further results indicated that it is present at about 30–35 ug/ml, and thereafter at about 10–50 ug/ml. This glycoprotein is substantially absent in NRS; i.e., the presence if any of this newly identified glycoprotein is in an amount of less than about one-twentieth of the amount present in APRS and is thus less than about 0.5 ug/ml. The newly found glycoprotein binds in vitro to LPS secreted by Gram-negative bacteria such as *Salmonella minnesota* Re595 when the glycoprotein and LPS are admixed in NRS, and it also retards the in vitro binding of LPS to HDL in NRS.

The further results discussed below relate to work in the human system that parallels work in the lapine system. The human homolog to the newly identified lapine glycoprotein appears to have a slightly higher molecular weight, but is functionally equivalent in its presence and substantial absence in acute phase serum and normal serum, respectively, its binding to LPS in vitro in normal human serum, and in its retardation of binding of LPS to serum HDL in in vitro determinations.

Etiocholanolone is a naturally occurring steroid metabolite experimentally useful for inducing local inflammatory reactions and fever in man. These responses typically begin within 8–20 hours after injection and last 2–6 hours [McAdam et al. (1978) *J. Clin. Invest.* 61:390; Wolff (1967) *Ann. Intern. Med.* 6:1268]. Etiocholanolone also induces typical plasma acute phase reactant responses, for example, CRP and serum amyloid A (SAA), within 24–48 hours after injection [McAdam et al. (1978) *J. Clin. Invest.* 61:390].

Samples of human serum collected at various times before and after etiocholanolone injection were surveyed for their ability to form an Re595-LPS protein complex of density 1.3 g/cc (C1.3) by admixing LPS with serum and maintaining the LPS serum admixture for a time period of 10 minutes prior to equlibrium density gradient centrifugation with CsCl. This reaction time was chosen from preliminary kinetic studies as a reaction time that would permit most of the Re595-LPS to complex with HDL in normal serum but trap C1.3 before its LPS transfers to HDL. Results of this survey are shown in FIG. 1.

FIG. 1a shows a CsCl density gradient using sera collected before and 32 hours after etiocholanolone injection; the appearance of a form of Re595-LPS in the bottom third of the gradient when APHS is used is evident. The density of this form of Re595-LPS was found to be 1.30 g/cc by measurement of refractive index.

The amount of Re595-LPS at d=1.3 g/cc as a function of time before or after etiocholanolone injection is shown in FIG. 1b. FIG. 1b also shows the CRP concentrations of the same samples surveyed for C1.3. The ability of serum to form C1.3 follows a time course similar to the acute phase CRP response that etiocholanolone induces [McAdam et al. (1978) *J. Clin. Invest.* 61:390].

The kinetics of Re595-LPS-HDL complexation of sera taken either before (in normal human serum; NHS) or 32 hours after (acute phase human serum; APHS) etiocholanolone injection was also studied. To obtain these data Re595-LPS serum mixtures were sampled at various times after mixing and examined using CsCl gradients.

The formation of Re595-LPS-HDL complexes is plotted as for a first order reaction in FIG. 2. Complexation of Re595-LPS with HDL in NHS has a one-half time (t ½) of about 7 minutes, whereas in APHS the reaction has a one-half time of about 52 minutes. This difference is virtually identical to that seen in rabbit serum where the one-half times are 2–4 minutes and 40–80 minutes for NRS and APRS, respectively [Tobias and Ulevitch (1983) *J. Immunol.* 131:1913].

The solubility properties of R595-LPS are different in NHS and APHS. The euglobulin precipitate dialysis procedure [Tobias and Ulevitch (1983) *J. Immunol.* 131:1913] results in Re595-LPS distributed in the dialyzed supernate, washes, and final precipitate as shown in Table II, below.

TABLE II

| | Percent Recovery of $^3$H-Re595 LPS from Euglobulin Precipitation[1] | |
|---|---|---|
| LPS Fraction | NHS (St. Dev.)[2] | APHS (St. Dev.)[2] |
| Not precipitated | 91.3 (4.7) | 39.5 (6.5) |
| Recovered in washes | 2.5 (0.25) | 1.5 (0.1) |
| In precipitate | 6.3 (4.4) | 59.0 (7) |

[1]Data are presented as a percentage of recovered LPS from two determinations. Overall recovery of reactant LPS was 52 percent.
[2]St. Dev. = Standard deviation.

Using NHS or APHS taken from the same volunteer before and after etiocholanolone injection, about 52 percent of the input LPS was recovered. Of this recovered LPS only 6.3 percent was recovered in the final precipitate when NHS was used, while 59 percent was recovered in the final precipitate when APHS was used. These results are thus similar to those discussed before from earlier work in the lapine system.

When the final euglobulin precipitates prepared from NHS and APHS in the absence as well as in the presence of Re595-LPS were examined by SDS-PAGE (FIG. 3), the precipitate from the LPS-APHS reaction mixture (lane E) contained a unique protein of apparent molecular weight 59,500 not found in any of the other precipitates.

Also run on the gel shown in FIG. 3 is a lane (A) containing rabbit LPS-APRS euglobulin precipitate with "gp60" marked. gp60 is the previously identified and isolated glycoprotein that precipitates from acute phase rabbit serum only in the presence of C1.3.

Whereas the human protein appears to be slightly smaller than rabbit LBP, this comparison might not have been valid since the molecular weights of glycoproteins do not dependably correlate with their mobility in SDS- PAGE [Bretscher (1971) *Nature New Biol.* 231:229]. However, now that the amino acid residue sequences of both proteins are known, it is found that the mature human protein contains five fewer residues than does the lapine homolog. The other difference noted between the lapine and human acute phase sera is that APRS C1.3-forming activity is stable at 4° C. for months, whereas APHS C1.3-forming activity is not stable even when sera are stored at −20° C. for more than several weeks.

It is concluded from these results, that as with the rabbit, a component of the human acute phase response interacts with Re595-LPS to reduce the rate of binding of LPS to HDL. The identity of the acute phase reactant in the human system was believed to be the before-discussed $alpha_2,beta_1$-glycoprotein. However, it has since been found to be LBP, a newly identified glycoprotein. It is further believed that a homolog of the human protein such as the newly identified glycoprotein in the lapine system carries out a similar function in other animals susceptible to Gram-negative bacterial infection.

Addition of rabbit CRP to normal rabbit serum to levels characteristic of acute phase serum does not reconstitute the observed phenomena. Additionally, reconstitution of ultracentrifugally delipoproteinated NRS with HDL from APRS does not reconstitute the observed phenomena. These observations argue that the prototypical acute phase reactants CRP and SAA are not involved. The remaining known acute phase reactants do not undergo large concentration changes between the normal and acute state and are therefore unlikely to be able to cause the qualitative differences between normal and acute phase serum observed.

Previous studies have shown that the mode of presentation of LPS; i.e., as a purified aggregated isolate or as an HDL complex, can significantly modify its endotoxic properties. An example of such presentation differences can be seen from FIG. 4 wherein it can be seen that LPS preincubated with delipoproteinated APRS is more rapidly cleared from a rabbit than is LPS preincubated with delipoproteinated NRS. Thus, the acute phase response appears to include a means for dealing with lipopolysaccharide endotoxins, and that means appears to be the lipopolysaccharide binding protein (LBP) discussed and described herein, and its homologs in other animals.

IV. LAPINE LBP

A. NRS Reconstitution Assay

Two examples of the NRS reconstitution assay for lipopolysaccharide binding protein (LBP) activity in the lapine (rabbit) system are shown in FIG. 5. In control studies, no systematic dependence on the assay results were observed when smaller total assay volumes; i.e., 0.5 or 0.25 ml rather than the standrard 1 ml, were used. Addition of 0.05 percent CHAPS [an N-alkyl sulfobetaine derivative of a bile acid amide reported to have an empirical formula of $C_{32}H_{58}N_2SO_7$, that is available from CALBIOCHEM, San Diego, Calif.] or 0.5M urea to NRS did not qualitatively block reconstitution although the quantitative effects were not studied. Reproducibility of the assay was found to be ±20 percent.

B. Purification of LBP

Since LPS added to serum forms a complex with HDL, it was determined whether an initial separation of the lipoprotein from APRS would be a useful first purification step. Mixing lipoproteins prepared from NRS or APRS with delipoproteinated NRS or APRS provided reconstituted sera with alternate sources of lipoproteins. As shown in FIG. 6, C1.3 formed only when delipoproteinated APRS was used and was independent of the source of the lipoproteins used to form the reconstituted serum. Therefore, whole APRS was used as the starting material for LBP isolation.

Chromatography of APRS on Bio-Rex 70 said by its distributor to be a weakly acidic cation exchanger containing carboxylic acid exchange groups on a macroreticular acrylic polymer lattice that is available from Bio-Rad, Richmond, Calif. proved to be a very effective initial step in purification of LBP. The absorbance profile of APRS and NRS passed over the column as well as the fractions pooled for analysis are shown in FIG. 7.

When 400 ml APRS were passed over a 50 ml bed of Bio-Rex 70, the ability to form C1.3 was largely removed. This can be seen in FIG. 8, where CsCl density gradient studies of the ability of the various pools to reconstitute NRS are shown. LBP activity was eluted only at salt concentrations above 300 millimolar (mM) NaCl, with the largest amount eluting in the 1 molar (M) NaCl wash; i.e., pool C, FIG. 8. Washing the column with 3M NaCl did not elute more LBP activity.

Assay results for the three pools eluted from the Bio-Rex 70 column are shown for a typical preparation of LBP in Table III, below. Overall, some 32 percent of the LBP activity was recovered for an increase in specific activity of 927 fold.

TABLE III

Purification of LBP

| | Volume (ml)[1] | LBP Activity (U/ml)[2] | Prot. (mg/ml)[3] | Total Sp.Act (U/mg)[4] | Total Activity (U)[5] | Total Protein (mg)[6] |
|---|---|---|---|---|---|---|
| Starting Material | | | | | | |
| APRS | 400 | 2.8 | 0.70 | 0.04 | 120 | 28000 |
| Bio-Rex 70 Pools | | | | | | |
| A | 6 | 13.9 | 0.65 | 21.4 | 83 | 3.93 |
| B | 6 | 14.3 | 0.45 | 31.8 | 86 | 2.73 |
| C | 6 | 32.9 | 0.54 | 60.9 | 197 | 3.21 |
| Overall for Bio-Rex: | | | | 37.1 | 366 | 9.87 |
| Overall purification factor = 927 | | | | | | |
| HPLC of Bio-Rex Pools | | | | | | |
| A | 2 | 4.6 | 0.12 | 38.3 | 9.2 | 0.24 |
| B | 2 | 15.1 | 0.20 | 75.5 | 30.2 | 0.40 |
| C | 2 | 40.6 | 0.44 | 92.3 | 81.2 | 0.88 |
| Overall for HPLC: | | | | 79.3 | 120.6 | 1.52 |
| Overall purification = 1982 fold | | | | | | |
| Purification of pool C through HPLC = 2307 fold | | | | | | |

[1]Sample volume in milliliters (ml).
[2]LBP activity in units per milliliter (U/ml) of the sample.
[3]Protein (Prot.) in the sample in milligrams per milliliter (mg/ml).
[4]Specific activity (Sp.Act.) of LBP in the sample in units per milligram (U/mg) of protein present.
[5]Total activity of LBP in the sample in units (U).
[6]Total protein in the sample in milligrams (mg).

Figure 7B:
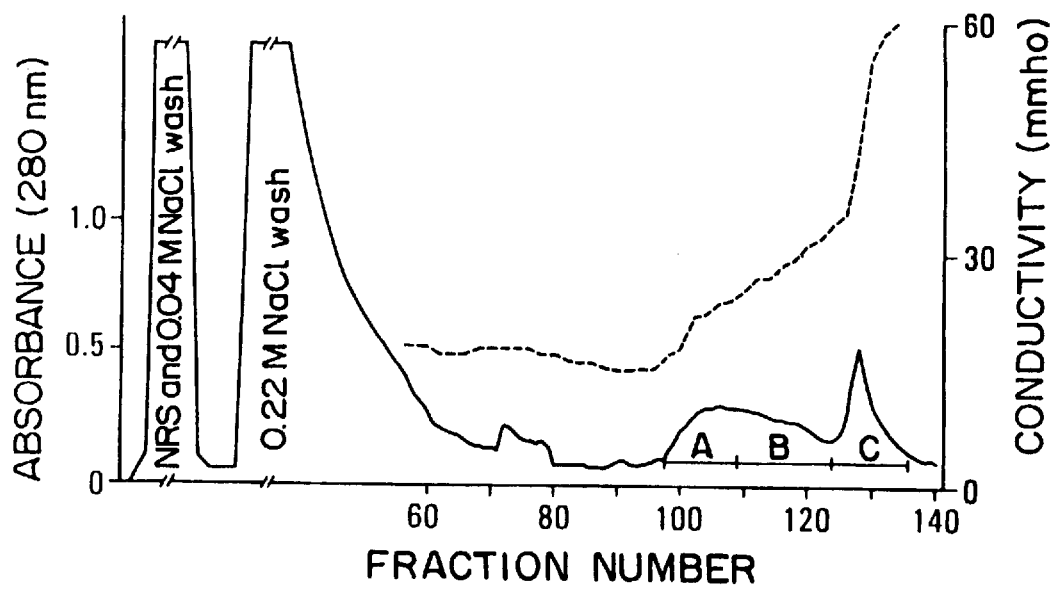
Figure 8A:
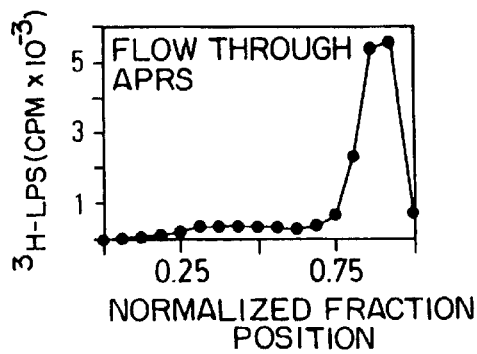
Figure 8E:
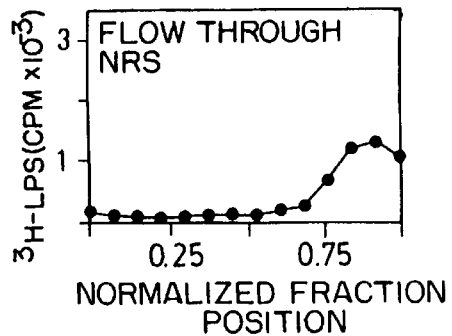
Figure 8B:
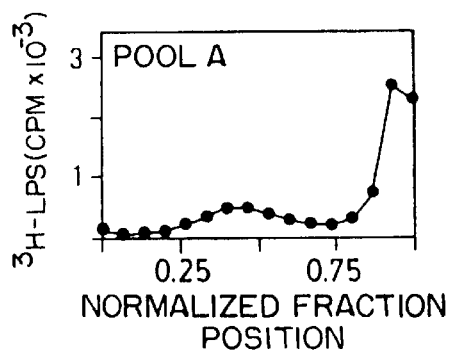
Figure 8F:
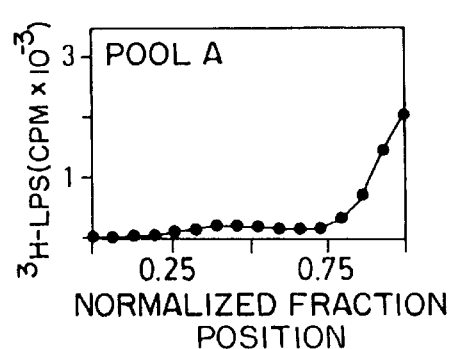
Figure 8C:
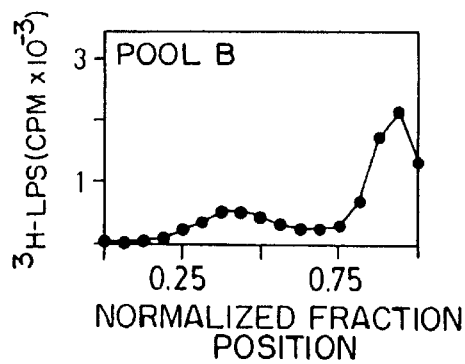
Figure 8G:
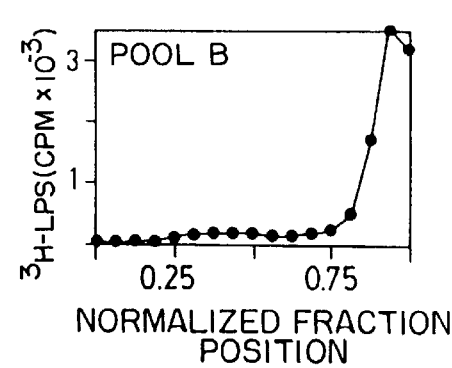
Figure 8D:
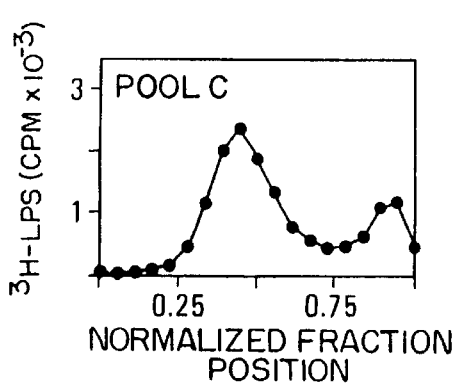
Figure 8H:
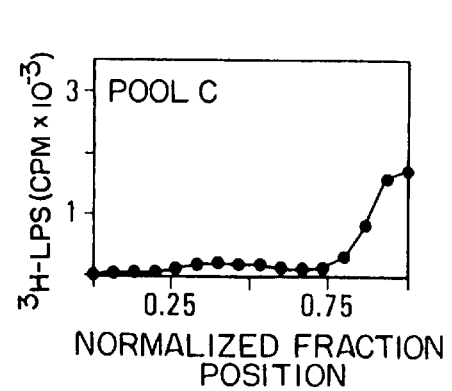

When NRS rather than APRS was chromatographed on the same column, an almost identical protein elution profile was obtained, as shown in FIG. 7B, but none of the pooled fractions had any significant LBP activity (FIG. 8). SDS-PAGE gels of the "C" pools from APRS and NRS are shown in FIG. 11, lanes 3 and 6, respectively.

Further purification of LBP was accomplished with HPLC using a Mono-Q column, said to be a strong anion exchanger, specially designed for rapid, high resolution chromatography of proteins that is available from Pharmacia Fine Chemicals, Piscataway, N.J. When an aliquot of Pool C from Bio-Rex 70 chromatography of NRS or APRS was run on the Mono-Q column and eluted with a gradient of ammonium sulphate, the absorbance profile of the eluate was as shown in FIG. 9. The profile obtained with Bio-Rex 70 Pool C derived from APRS shows a peak eluting near 20 minutes not seen in the profile obtained with Pool C derived from NRS.

Fractions containing the unique APRS-derived peak as well as the analogous fractions from the NRS material were assayed for LBP activity. As shown in FIG. 10, the unique protein peak from APRS showed good LBP activity. All other fractions tested had no LBP activity.

An SDS-PAGE gel analysis of the LBP-containing peak is shown in FIG. 11, lane 8. From the mobilities of the two bands in lane 8, relative to the standards in lane 9, the apparent relative masses ($M_r$) (molecular weights) of the two proteins are 60,500 and 58,000 daltons (D). Judging by staining intensity, the 60.5 kilodalton (kD) band usually comprises 90 percent of the mixture.

Final resolution of the two proteins present in the active pool from Mono-Q chromatography was accomplished by SDS-PAGE, slicing the two bands apart after staining and recovering the proteins by electroelution. The separation of the two bands is shown in FIG. 12.

Amino acid sequence data, described below, suggests that both bands have very similar primary structures, arguing that both bands may be LBP. Both bands stain with periodic acid-Schiff reagent, thus they are both glycoproteins.

The above separation procedure, while carried out using lapine LBP is also effective for purification of human LBP from APHS. However, a more efficacious purification of human LPB results when eluted from Bio-Rex 70 columns with a 0.04M to 0.5M NaCl gradient. The column is first washed with a 0.04M NaCl solution containing 2 mM EDTA in 0.05M phosphate buffer. The NaCl gradient, diluted in the same buffer, is then passed through the column. The final wash consists of 2M NaCl in the same buffer. Human LBP elutes in the NaCl gradient fraction.

C. Amino Acid Sequence Data

Partial amino acid sequence data were obtained for two preparations of LBP, the mixture of 60.5 kD and 58 kD proteins obtained from Mono-Q chromatography and the 58 kD protein purified by SDS-PAGE. Initially, material collected from Mono-Q chromatography was sequenced. Since this material consists of 80–90 percent of the 60.5 kD protein, these data reflect the sequence of the major component recovered from the column.

The amino acid residue sequence of the first 39 amino acids from the amino-terminus of lapine LBP were determined to be as shown below. With the exception of positions 1,36,38, and 39, all positions were determined in duplicate for two different preparations. Positions 1,36,38, and 39 were identifiable in only one run of the sequenator. Position 30 did not yield an identifiable residue and may represent a site of glycosylation, most probably an asparagine (Asn) residue, although a leucine residue was found from the DNA sequence. Sequence data for the 58 kD minor protein was obtained for 36 residues. The sequence of the 58 kD protein agreed completely with that of the mixture of proteins, even to the indeterminate residue 30. This polypeptide is refered to as polypeptide A.

1                                             10
Thr—Asn—Pro—Gly—Leu—Ile—Thr—Arg—Ile—Thr—

11                                            20
Asp—Lys—Gly—Leu—Glu—Tyr—Ala—Ala—Arg—Glu—

21                                            30
Gly—Leu—Leu—Ala—Leu—Gln—Arg—Lys—Leu—XXX—

21                                            39
Gly—Val—Thr—Leu—Pro—Asp—Phe—Asp—Gly

The 39 amino acid residue sequence was used to search for homologous sequences in the National Biomedical Research Foundation protein sequence database using the Wordsearch program from the University of Wisconsin Genetics Computer Group. To distinguish between random and non-random matches found by the computer search, the Wordsearch program was submitted to a randomized sequence having the same composition as the peptide shown above. Those matches found with the LBP sequence were eliminated from consideration whose "quality scores" were not better than the matches found with the randomized sequence.

This procedure resulted in two matches to portions of sequences of previously reported proteins (as shown below) i.e., human influenza virus b hemagglutinin precursor (INFLUENZA) [Krysal et al., *Proc. Natl. Acad. Sci. USA* 80:4527 (1983)] and baker's yeast glyceraldehyde 3-phosphate dehydrogenase (BAKER'S YEAST). Holland et al., *J. Biol. Chem.* 258:5291 (1983). (The hyphen in the second LBP sequence represents the indeterminate residue at position 30 from the amino-terminus.)

| | |
|---|---|
| 5 LITRITDKGLEYAAREGLLALQRKLXGVTLP | 35 LBP |
| 459 LAVLLSNEGIINSEDEHLLALERKLKKMLGP | 489 INFLUENZA |
| 8 RITDKGLEYAAREGL-LALQRKLXGV | 32 LBP |
| 2 RIAINGFGRIGRLVLRLALQRKDIEV | 27 BAKER'S YEAST |

The Wordsearch program was also used to look for homology between the sequences of LBP and rabbit CRP [Wang et al., *J. Biol. Chem.* 257:13610 (1982)], human serum amyloid P [Mantzouranis et al., *J. Biol. Chem.* 260:7752 (1985)], human serum amyloid a [Sipe et al., *Biochemistry* 24:2931 (1985)], syrian hamster female acute phase protein [Dowton et al., *Science* 228:1206 (1985)], human alpha-1-antichymotrypsin precursor [Chandra et al., *Biochem* 22:5055 (1983)], human alpha-1 acid glycoprotein [Dente et al., *Nucleic Acid Res.* 13:3941 (1985)], and the major acute phase alpha-1 glycoprotein of the rat. Cole et al., *FEBS Lett.* 182:57 (1985). No significant homology was found with any of these acute phase reactants.

LBP has recently been found to be structurally similar to bactericidal/permeability increasing protein (BPI) Tobias et al. (1988) *J. Biol. Chem.* 263:13479, whose disclosures are incorporated by reference. A comparison of the two proteins shows that both bind to the lipid region of LPS, have a high degree of amino-terminal sequence homology, and are immunologically cross-reactive. However, the cellular origins, localization and function of the two proteins are different, and the proteins are considered to be different.

Comparison of the first 20 amino-terminal residues show rabbit LBP and human BPI have eleven identical residues. Five other residues are chemically conservative substitutes that can be accomplished by simple base changes in DNA. BPI also cross-reacts with two components of anti-LBP serum.

However, BPI is isolated from neutrophils, where it is bound tightly in the membranes of myeloperoxidase-containing primary granules. In contrast, LBP synthesis is detected in rabbit liver and rabbit hepatocytes after an acute phase stimulus.

BPI has two functions, killing and permeabilizing Gram-negative bacteria. LPS shows no bactericidal activity.

LBP binds to LPS in acute phase serum and retards binding of LPS to high density lipoprotein. Centrifugation density techniques combining LPS, HDL and LBP show a density shift from 1.33 to less than 1.2 g/cc as stated previously. BPI alters density only from 1.33 to 1.29 g/cc when used to replace LBP. Therefore, the functional similarity of the two proteins appears to be limited to the ability to bind LPS.

D. Depletion of APRS with Rat Polyclonal Anti-LBP

When examined by radial immunodiffusion, rat antisera induced by introduction of whole, substantially purified lapine LBP were reactive with APRS and LBP-containing fractions of APRS isolated by Bio-Rex 70 and Mono-Q columns, but not with NRS or NRS fractions corresponding to the fractions isolated from APRS. The antisera were then tested for their ability to immunoprecipitate LBP and simultaneously remove LBP activity from APRS. In these studies, both NRS and APRS were admixed with immune and non-immune rat sera. After precipitation, the supernates were collected to determine their ability to form C1.3 (FIG. 13), indicating the presence or absence of LBP activity, and the precipitates were saved for analysis by SDS-PAGE (FIG. 14).

When the supernates from the immunoprecipitates were assayed for their ability to form C1.3, the amount of C1.3 observed was inversely proportional to the amount of immune serum added to the APRS (FIG. 13). Rat sera, immune or not, did not inhibit the binding of $^3$H-LPS to HDL in NRS.

When the constituent proteins of the immunoprecipitate were visualized by SDS-PAGE, only the admixtures of immune rat serum reacted with APRS yielded significant immunoprecipitates with bands corresponding to LBP (FIG. 14, lanes 5–7). The intensity of the LBP band in the immunoprecipitates correlated positively with the amount of immune serum admixed (FIG. 14, lanes 5–8), and correlated negatively with the ability of the residual supernate to form C1.3 (see FIG. 13).

Bands other than LBP observed in the immunoprecipitates are attributable to rat albumin and rat heavy and light immunoglobulin chains. The combination of NRS with immune rat serum did yield very weak bands corresponding to rat immunoglobulin chains and to LBP (FIG. 14, lane 3). Non-immune rat serum reacted with either NRS or APRS yielded only bands corresponding to albumin (FIG. 14, lanes 2 and 4).

Thus, immunoprecipitation of LBP and APRS decreased the ability of APRS to form C1.3 in a dose dependent manner.

E. Interaction of LPS with LBP

Two types of studies were performed to determine whether LPS and LBP interact directly; immunoprecipitation of $^3$H-LPS as C1.3 in APRS by anti-LBP sera, and delivery of $^{125}$I to LBP by photolysis of $^{125}$I-ASD-LPS [LPS coupled to sulfosuccinimidyl-2-(p-azidosalicylamido)-1,3'-dithiopropionate that was radio-iodinated after coupling] as C1.3 in APRS.

In the immunoprecipitation studies, $^3$H-LPS and APRS (or NRS) were admixed, allowed to react and form a complex at 37 degrees C. for 10 minutes, and the admixture was then cooled to zero degrees C. before rat anti-LBP was added. The $^3$H-LPS content of a portion of the immunoprecipitate was determined by liquid scintillation counting while the remainder of the precipitate was taken for SDS-PAGE. Since LPS may bind non-specifically to immune precipitates [Ginsberg et al., J. Immunol. 120:317 (1978)], immunoprecipitation of rabbit C-reactive protein (CRP) from APRS by goat anti-CRP in the presence of $^3$H-LPS was used as a control experiment.

The SDS-PAGE analysis of the immunoprecipitates is shown in FIG. 15 together with the data for $^3$H-LPS recovered with the immunoprecipitate. The results show a clear positive correlation between LBP precipitation and $^3$H-LPS precipitation.

However, in preliminary studies, $^{125}$I-ASD-LPS was shown to cosediment with underivatized LPS in a CsCl gradient, form C1.3 with APRS, and bind to HDL in APRS more slowly than in NRS.

Further evidence for interaction of LPS with LBP was obtained through the use of $^{125}$I-ASD-LPS. APRS (or NRS) was admixed and allowed to react with $^{125}$I-ASD-LPS for 5 minutes at 37 degrees C. in the dark to form a complex, then chilled to stop further transfer to HDL, and photolyzed. Anti-LBP antiserum was then added to collect LBP for SDS-PAGE for autoradiographic analysis. The results as well as the results of control studies, are presented in FIG. 16.

Lane 1 of FIG. 16 shows that $^{125}$I-ASD-LPS photolyzed in 20 mM EDTA, 150 mM NaCl, pH 7.4 does not yield a Coomassie blue stainable band (1a) and the 125I runs with the dye front (1b). Lanes 2 and 3 show that $^{125}$I-ASD-LPS mixed with immunopurified anti-LPS labels immunoglubulin heavy chains if photolyzed after admixing (lane 3), but only very weakly if photolyzed also before admixing (lane 2). For lanes 1–3, aliquots of the reaction mixtures were applied directly to the gels. For lanes 4–7, the reaction mixtures were immunoprecipitated with anti-LPS before application to the gel.

Lanes 4 and 5 show that $^{125}$I-ASD-LPS, whether photolyzed only after admixture with NRS (lane 5) or also photolyzed before with NRS did not label any material immunoprecipitable with anti-LBP; i.e., lanes 4b and 5b are clear. Lanes 6 and 7 show that $^{125}$I-ASD-LPS admixed with APRS labels LBP strongly if photolyzed after admixing with APRS (lane 7), but labels LBP only weakly if also photolyzed before admixing with APRS (lane 6).

The binding of purified lapine LBP to LPS immobilized on plastic microtiter plates has also been examined. The presence of LBP bound to LPS was detected with goat anti-rabbit LBP and peroxidase conjugated rabbit anti-goat IgG.

LBP was found to bind to a variety of LPS types from both rough and smooth strains of Gram-negative bacteria, to lipid A, and to the tetraacyl glucosamine disaccharide diphosphate precursor IVA, but only poorly to the diacyl glucosamine phosphate, lipid X. No binding to KDO was observed. Binding affinities of LBP for LPS are near $10^9$ $m^{-1}$.

The data from these studies are shown in Table IV, below, where the numerical results are the concentrations necessary to reduce the binding of 1 microgram (ug)/ml LBP to the plate by 50 percent; i.e., $ED_{50}$. It is noted that in some instances, the structure of the inhibitor is either not fully defined or the inhibitor is heterogeneous, thereby preventing a calculation of a molar concentration for $ED_{50}$.

TABLE IV

| Assay Substance | $ED_{50}$ ng/ml | nM |
|---|---|---|
| Re595-sugars | >200,000 | >840,000[a] |
| AMP | >1,000,000 | >2,800,000 |
| Lipid x | 2,800 | 3,900 |
| Dimyristoyl phosphatidic acid | 2,500 | 3,900 |
| DADG-BSA | 540 | 570 |
| IVA-BSA | 190 | 135 |
| S. typhimurium Rc (desacyl) | 266 | 78 |
| J5 LA (BSA) | 79 | 40 |
| J5 LA (synthetic) | 40 | 20 |
| J5 LA (isolated) | 79 | 40 |
| Re595-BSA | 26 | 12 |
| Re595 | 13 | 6 |
| E. coli D31m4(Re) | 13 | 6 |
| Salmonella typhiumurium Rc | 22 | 7 |
| Salmonella minnesota R5 (Rc) | 67 | |
| Salmonella minnesota R60 (Ra) | 12 | |
| Salmonella minnesota W.T. | 69 | |
| E. coli 0111:B4 | 50 | |
| E. coli K12 mm 294 | 18 | |
| E. coli 055.B5 | 48 | |
| Serratia marscesens | 25 | |
| Salmonella typhimurium | 107 | |
| Vibrio cholerae | 50 | |
| Klebsiella pneumoniae | 53 | |
| RNA | >300,000 | >850,000[b] |
| DNA | >300,000 | >850,000[b] |
| Heparin | 21,000 | |
| Lipoteichoic acid | 480 | |
| Dextran sulfate | 73 | |

[a]Molarity of the constituent 3 deoxy-D-mannooctulosonic acid.
[b]Molarity of the constituent monomers.

A qualitative analysis of the above data indicate that an intact lipid A moiety is essential for the strongest inhibition. Thus, as the lipid A moiety is dissected in the series lipid A, IVA, DADG, lipid X, the $ED_{50}$ values steadily increased.

In addition, when Salmonella typhimurium Rc LPS is enzymatically deacylated to a product analogous to IVA the $ED_{50}$ value also increases. By contrast, removing the O-antigen and the core oligosaccharide in the LPS from Salmonella minnesota wild type, R60, R5, and Re595 had no systematic effect and certainly does not diminish the affinity of LBP for these molecules.

The KDO moiety of Re595 LPS, presented as a mixture of the KDO mono- and dissachride, was completely ineffective as an inhibitor. Large negatively charged molecules such as DNA, RNA, and heparin were inhibitory only at high concentrations, whereas lipoteichoic acid and dextran sulfate were fairly good ligands for LBP. AMP, as a representative monomer of DNA and RNA was also ineffective.

Intentionally complexing J5 lipid A and Re595 to BSA had little effect on their ability to bind to LBP. Qualitatively this means either that the LBP-LPS interaction is much stronger than any BSA-LPS interaction or that BSA and LBP bind to different parts of the LPS in a non-interactive manner.

The results in Table IV thus support the concept that LBP contains a binding site for lipid A.

V. MATERIALS AND METHODS

Part I—Related to Sections II and III

A. Lipopolysaccharide Purification

LPS, either biosynthetically tritiated or unlabeled, was purified from Salmonella minnesota Re595 as described by Galanos et al. Euro. J. Biochem. (1969) 9:245 and modified by Ulevitch et al. (1981) J. Clin. Invest. 67:827. Briefly, 50 grams (g) of dried bacteria, prepared as described hereinafter, were admixed with 200 milliliters (ml) of extraction mixture [a monophasic solution containing aqueous phenol (90 g dry phenol+11.0 ml H2O), chloroform and petroleum ether (b.p. 40–60 degrees C.) in a volume ratio of 2:5:8, respectively]. The admixture was then stirred for 5 minutes producing a fine suspension of whole bacteria. The suspension was then centrifuged (5000 rpm for 15 minutes in a Sorvall GSA rotor) to form a bacterial pellet and an LPS-containing supernatant. The pellet and supernatant were separated and the supernatant was filtered to remove any remaining bacteria or cellular debris. The bacterial pellet was subjected to the same extraction procedure one or two more times with each resulting LPS-containing supernatant being admixed with the first.

Petroleum ether and chloroform were then removed from the pooled supernatants by rotary evaporation at 30–40 degrees C. To the resulting LPS-containing aqueous phenol solution was slowly admixed water until the LPS precipitated. The admixture was subsequently centrifuged (3000 rpm for 10 minutes in a Sorvall GSA rotor) so as to form a LPS pellet and supernatant.

The LPS pellet was separated from the supernatant and washed two or three times with about 5 ml of 80 percent phenol (w/v in H2O) by suspension and centrifugation. The LPS pellet was then washed three times with 5 ml of ether by suspension and centrifugation to remove any remaining phenol, and dried in vacuo.

The dried Re595 was then admixed with sufficient 20 mM EDTA (pH 7.5) to dissolve the LPS upon sonic oscillation in a model W-375 sonicator from Heat Systems-Ultrasonics, Inc., Plainview, N.Y. The LPS solution was dialyzed against 3 liters of sterile water for 72 hours, with a change of the dialysis bath every 12 hours, and then lyophilized. Fresh stock solutions of 5 mg/ml LPS were prepared by addition of the LPS to the appropriate buffer, followed by sonic oscillaiton at 25 degrees C.

B. Bacteria Production

The LPS-producing bacterial strain Salmonella minnesota Re595, obtained from New England Enzyme Center, Tufts University, Boston, Mass., was cultured in a growth medium containing Ardamine Z at 22.5 g/l, NZ amine NAK at 11.0 g/l, K2PO4 at 16.6 mg/l, KO4 at 4.0 g/l and Cerelose at 66.6 mg/l, all also obtained from New England Enzyme Center. Growth medium, typically one liter in a three liter flask with baffle plates, was inoculated with 20 ml of a confluent (plateau) S. minnesota Re595 culture and inoculated at 37 degrees C. with vigorous agitation for about 8 hours. Bacteria containing LPS were subsequently harvested by centrifuging the cultures to form a bacterial pellet and supernatant. The bacterial pellet was separated from the supernatant and washed three times by resuspension in deionized water and repelleting by centrifugation. The final washed pellet was resuspended in about 50 ml of deionized water and lyophlized, typically yielding about 4.5 g dry weight bacteria per liter of culture.

To prepare S. minnesota Re595 containing LPS biosynthetically labeled with tritium ($^3H$), about 62.5 mCi of 3H-sodium acetate (Amersham, Santa Ana, Calif.) were admixed with one liter of the growth medium just prior to inoculation. The bacteria were then cultured and harvested as previously described, typically yielding about 7–8 mCi $^3H$ per 4.5 g dry weight bacteria.

C. Complex Formation

Etiocholanolone was used to induce an acute phase response [McAdam et al. (1978) J. Clin. Invest. 61:390] in three human volunteers by intramuscular injection of 0.3 milligrams etiocholanolone per kilogram of volunteer body weight.

Serum was collected at various times from 24 hours previous to etiocholanolone injection, to 120 hours after injection. Observation and quantitation of Re595-LPS complex formation in sera using CsCl gradients was as described in Tobias and Ulevitch (1983) *J. Immunol.* 131:1913.

Preparation of euglobulin precipitate from Re595-LPS serum reaction mixtures was accomplished as described by Tobias and Ulevitch (1983) *J. Immunol.* 131:1913. Briefly, the reaction was allowed to proceed for 2 minutes at 37° C., followed by stopping the reaction by rapid chilling in an ice bath. The chilled reaction mixture was dialysed overnight at 4° C. versus 2.5 millimolar (mM) HEPES, 15 mM NaCl, at pH 7.65. The resulting precipitated euglobulin fraction was collected by centrifugation, washed twice with 10 mM HEPES, 140 mM NaCl, at pH 7.4, and was then suspended in distilled water for ease of handling. Re595-LPS in the supernate, washes, and euglobulin precipitate was quantitated by 3H measurement.

D. Electrophoresis and CRP Analysis

Polyacrylamide gel electrophoresis in the presence of sodium dodecyl sulfate (SDS-PAGE) was performed using the recipes of Laemmli [Laemmli (1970) *Nature (London)* 222:680]. Measurement of serum C- reactive protein (CRP) levels were performed in the clinical laboratory of Scripps Clinic and Research Foundation following usual procedures.

E. Purification of the Acute Phase Reactant from Rabbit Serum

Acute phase rabbit serum was prepared as described in Tobias and Ulevitch (1983) *J. Immunol.* 131:1913. The newly identified LBP material was purified from APRS as follows.

The primary purification step was ion-exchange chromatography on Bio-Rex 70 (Bio-Rad Laboratories, Richmond, Calif.). A 25 ml column of resin was equilibrated with 0.05 molar (M) sodium phosphate, 2 mM EDTA, pH 7.3 buffer (Pi/EDTA buffer) in the cold (about 4° C.). Thereafter, 200 ml of APRS was run through the column. The column was then washed first with Pi/EDTA buffer, and then with 0.22M NaCl, 0.05M sodium phosphate, 2 mM EDTA as a pH 7.3 buffer until the ultraviolet absorption of the eluate at 280 nanometers was less than 0.1.

A linear salt gradient of 30 ml each of 0.22M and 0.5M NaCl in Pi/EDTA buffer was then started followed by 50 ml of 1M NaCl in Pi/EDTA. The desired glycoprotein-LPS binding (complex forming) activity primarily eluted at the end of the gradient with 1M NaCl.

The active fractions were further purified by gel filtration using G-150 Sephadex (Pharmacia Fine Chemicals, Piscataway, N.J.) in 5 mM sodium phosphate at pH 7.3 to remove low molecular weight contaminants. The activity eluted from the gel filtration column was very close to the elution position of BSA. Thus, the activity-bearing glycoprotein had an apparent relative molecular weight of about 60,000.

The acute phase glycoprotein reactant bound to DE-52 cellulose (Whatman, Inc., Clifton, N.J.) equilibrated with 5 mM sodium phosphate pH 8.3 and eluted in active form with 1M NaCl. Salt gradient elution from the column provided a further purification step.

The presence of desired glycoprotein during the before-described purifications (Section D) was monitored by assaying the collected fractions for the ability of their components to form a complex with LPS. The presence of a complex-forming activity was ascertained by a centrifugal density gradient assay.

F. Sucrose Density Gradient Ultracentrifugation

The activity was recovered from a sucrose density gradient prepared with 5–20 percent sucrose and centrifugation for 2 hours at 45,000 RPM using a TV 865 rotor (DuPont Co., Instrument Products Biomedical Div., Newtown, Conn.) at an average value of 4 Svedbergs (S). Each gradient so prepared was divided into 8 fractions. Each fraction so obtained was assayed for its ability to form a 1.3 g/cc complex using a CsCl density gradient method analogous to that described hereinafter using $^3$H-LPS and APRS. These assays serve to confirm the roughly 60,000 dalton molecular weight of the activity-containing glycoprotein.

G. Analysis of LPS Binding to Newly Identified Glycoprotein

LPS binding to the newly identified glycoprotein in rabbit serum was carried out as follows.

An aliquot of an animal body sample to be assayed for LPS binding activity was first concentrated, as necessary, to provide a composition containing about 1 mg/ml of solids having a molecular weight greater than about 10,000 using an Amicon ultrafiltration apparatus with a YM 10 membrane (Amicon Corp., Scientific Systems Div., Danvers, Mass.). About 10 to about 250 microliters (ul) of the concentrated body sample were admixed with 0.5 ml of NRS containing 20 mM EDTA.

At time zero, 5 ug of $^3$H-LPS was admixed with the above admixture. Ten minutes thereafter, t=10, 4.3 ml of normal saline containing 1.8 g of CsCl previously maintained at 0° C. was admixed with the $^3$H-LPS/body sample aliquot admixture.

The resulting admixture was centrifuged for a time period of 16 hours at 45,000 RPM using a TV865 rotor. The resulting density gradient was fractionated and the counts in fractions of varying densities were determined as is shown in FIG. 1.

H. HDL Deficient Serum

High density lipoprotein (HDL) deficient (depleted) serum, from either normal or acute phase rabbits or humans, was prepared by methods well known in the art. Briefly, the density of 35 ml of serum was adjusted to about 1.24 g/cm$^3$ by admixing 13.2 g of KBr. The serum/salt admixture was then centrifuged to gradient equilibrium in a high gravitational field, i.e., about 113,000×gravity [48–60 hours at 40,000 rpm in a 60 ti rotor (Beckman Instruments, Palo Alto, Calif.]. HDL, being less dense than the other components of the admixture, concentrates as a stable band with a yellowish color at the top of the gradient. The HDL band was separated from the gradient and discarded. The volume of the remaining serum/salt admixture was then adjusted to 35 ml and its density adjusted to 1.24 g/cm$^3$ by admixture of an appropriate amount of KBr. The centrifugation and separation procedure was repeated. The resulting serum/salt admixture was then dialyzed against 0.9 percent saline to substantially remove KBr from the admixture. Finally, the admixture was adjusted to its original volume (35 ml) by admixture of an appropriate amount of 150 mM NaCl.

I. LPS Clearance Kinetics

The effects of acute phase reactants on the kinetics of LPS clearance from mammalian blood were studied in rabbits using biosynthetically labelled LPS ($^3$H-LPS). One hundred fifty micrograms of H-LPS were admixed with 15 ml of either (1) HDL deficient APRS; or (2) HDL deficient NRS. The admixtures were incubated for 10–30 minutes at 20 degrees C. to allow binding of $^3$H-LPS to any acute phase reactants in the admixtures.

Three groups of 5 rabbits each were catheterized and the described admixtures were injected into the femoral vein and artery. Three milliliters of one of the above described admixtures were injected into the femoral vein of all rabbits in one group. Blood samples were taken from the femoral artery catheter at the time intervals shown in FIG. 4. The serum was separated from each blood sample and the amount of $^3$H-LPS present in each serum sample was determined by liquid scintillation.

Part II—Related to SECTION IV

Materials:

Biosynthetically tritiated LPS ($^3$H-LPS) and unlabelled LPS were isolated from *Salmonella minnesota* Re595 as described previously. (Tobias et al., *Infect. Immun.* 50:73 (1985); Galanos et al. *Eur. J. Biochem.* 9:245 (1969). Rabbit blood was collected either by bleeding from the median ear artery or by heart puncture, allowed to clot at 37 degrees C. for 2–6 hours and at zero degrees C. overnight, centrifuged to remove clot fragments and cells, and the serum was stored frozen without preservative. Acute phase rabbit serum (APRS) was collected 24 hours after induction of an acute phase response by subcutaneous injection of 1 ml of 3% (W/V) silver nitrate in distilled water. Serum collected from non-induced rabbits was tested for "normality" before being used as normal rabbit serum (NRS). The initial assay used was immunodiffusion versus antiserum to rabbit c-reactive protein (CRP). Sera assaying negative for CRP were further assayed as described below to ensure a sufficiently rapid rate of binding of LPS to HDL. These precautions were instituted after observing that more than 50% of a batch of newly acquired rabbits had readily detectable acute phase reactants in their sera.

Polyclonal rat antisera to whole, substantially purified lapine LBP, as obtained from the two-column (Bio-Rex 70 and Mono-Q) purification procedure described herein, were raised in Lewis rats by intraperitoneal injection of each rat with 25 micrograms (ug) LBP in complete Freund's adjuvant, with 25 ug LBP in incomplete Freund's adjuvant at 3 weeks, and with 10 ug LBP in buffer at 6 weeks. Animals were bled by heart puncture under Innovar-Vets anesthesia and serum collected as described above. Immunoprecipitation studies using these sera were performed by incubating rabbit serum together with varying volumes of antiserum for at least 3 hours at 37 degrees or 4 hours at 4 degrees. Precipitates were collected by centrifugation and washed twice with 50 mM phosphate buffer, 150 millimolar (mM) NaCl, 0.1% Tween-20 [polyoxyethylene (20) sorbitan monolaurate], pH 7.4.

Unfractionated lipoproteins and deliproproteinated sera were prepared by ultracentrifugation. To 35 milliliters (ml) of serum were added 13.23 grams (g) of KBr, after which the serum was spun at 40,000 RPM in a 60 Ti (Beckman Instruments, Fullerton, Calif.) rotor for 36–60 hours at 4 degrees. After fractionation, protein assay, and cholesterol assay (CALBIOCHEM, La Jolla, Calif.), the lipoproteins and serum proteins were separately pooled and dialysed extensively against 10 mM HEPES, 150 mM NaCl, pH 7.4. Finally the delipoproteinated sera and the lipoproteins were brought to 75 percent and 25 percent of the original serum volumes, respectively, by dilution or concentration as required. Delipoproteinated sera and lipoproteins were recombined in a 3:1 ratio, respectively, to prepare lipoprotein reconstituted sera.

LPS was coupled to sulfosuccinimidyl-2-(p-azido salicylamido)-1,3'-dithiopropionate (Pierce) as described [Wollenweber et al. J. Biol. Chem. 260:5068 (1985)], and the resulting derivative (ASD-LPS) was radiolabelled with 125I using chloramine T [Ulevitch, *Immunochemistry* 15:157 (1978)] to yield $^{125}$I-ASD-LPS. The product had a specific activity of 7.1×109 counts per milligram (cpm/mg) LPS from which the incorporation of $^{125}$I into LPS is calculated to be approximately 0.3 moles percent. Preliminary data indicate that $^{125}$I-ASD-LPS co-sediments with LPS in CsCl gradients. $^{125}$I-ASD-LPS is quantitatively taken up by HDL and NRS and APRS, and ASD-LPS has the same mitogenicity as LPS when assayed with murine splenic B cells. Photolysis of $^{125}$I-ASD-LPS was accomplished using a Rayonet photochemical reactor (Southern N.E. Ultraviolet Co., Middletown, Conn.) equipped with General Electric F8T5.BLB lamps with a peak output at 370 nanometers (nm). Reaction mixtures were exposed for 10 minutes on ice.

Bovine serum albumin (BSA) conjugates of Re595-LPS, *Escherichia coli* J5 LPS, precursor IVa, and 0-[2-amino-2-deoxy-$N^2$-(3-hydroxytetradecanoyl)-beta-D-glucopyranosyl]-(1-6)-amino-2-deoxy-$N^2$-(3-hydroxytetradecanoyl)-alpha-D-glucopyranose 1,4'-bisphosphate, (DADG) prepared by a published method were obtained from Dr. T. Kirkland (University of California, San Diego, Calif.). *Salmonella typhimurium* Rc LPS and the desacyl form derived therefrom were provided by Dr. R. Munford (University of Texas, Dallas, Tex.). Commercial sources were used to obtain other lipopolysaccharides (List Biologicals, Campbell, Calif.), synthetic J5 lipid A (LA-15-PP, Daichi Pure Chemicals, Tokyo) lipid X (Lipidex, Middleton, Wis.), polymixin B (Calbiochem, La Jolla, Calif.), horseradish peroxidase coupled to rabbit anti-(goat IgG) (Cooper-Biomedical, Malvern, Pa.), o-phenylenediamine, lipoteichoic acid, salmon testes DNA, yeast transfer RNA, and adenosine-5'-monophosphate (AMP) (Sigma, St. Louis, Mo.), dextran sulfate (prepared from 500,000 kDA dextran, Pharmacia, Uppsala, Sweden) heparin (Liquaemin sodium, 140–165 u/mg, Organon, West Orange, N.J.) and dimyristoyl phosphatidic acid (Avanti Polar lipids, Pelham Ala.). Microtiter plates were Dynatech #001-010-2201. A mixture of 3-deoxy-D-mannooctulosonic acid (KDO) mono- and disaccharide was prepared from Re595 LPS by mild acid hydrolysis by the procedure of Brade et al. (1983) *Eur. J. Biochem.*, 131:201. A portion of the Re595 LPS hydrolyzed was biosynthetically tritiated using [$^3$H] acetate, which should result in label principally incorporated into the fatty acids of lipid A. No tritium was found in the KDO preparation, is interpreted as an absence of LPS and lipid A.

METHODS:

A. General

Sodium dodecyl sulfate polycrylamide gel electrophoresis (SDS-PAGE) with staining by Coomassie blue or periodic acid-Schiff reagent was performed by published procedures. Tobias et al. Immunol. 128:1420 (1982). All samples were reduced with 2-mercaptoethanol prior to SDS-PAGE concentration of LPS, and its derivatives were determined using the ketodeoxyoctanoate assay [Cyubin et al., *Nature (Lond.)* 186:155 (1960)] with LPS as standard. Protein concentrations were determined by either the Folin [Lowrey et al., *J. Biol. Chem.* 193:265 (1951)] or BCA (Pierce Chem. Co., Rockford, Ill.) reagents using bovine serum albumin as standard. All reactions of LPS or LPS derivatives with APRS or NRS were carried out at 10 milligrams per milliliter (mg/ml) unless otherwise noted.

B. Kinetics of LPS binding to HDL

The kinetics of LPS binding to HDL in serum were observed and quantitated by CsCl isopycnic density gradient ultracentrifugation. To 8 ml of rabbit serum were added 0.4 ml of 0.4M EDTA at pH 7.4, and the mixture was warmed to 37 degrees C. in a water bath. At time zero, 0.4 ml of 200 micrograms per milliliter (ug/ml) $^3$H-LPS in 0.02M EDTA, pH 7.4, were added. At suitable times, 1.0 ml aliquots of the reaction mixture were removed and added to 3.8 ml of ice cold 2.81M CsCl, 0.15M NaCl. These samples were then spun to equilibrium for 16 hours at 45,000 RPM in a TV-865 rotor (DuPont Sorvall, Wilmington, Del.) at 0–4 degrees C. Following centrifugation, the gradients were fractionated, the refractive index measured if the density profile of the gradient was to be determined, and the $^3$H-LPS in each fraction determined. The efficiency of measuring 3A-Re 595 LPS was found to be independent of the amount of CsCl in each vial. After graphing the $^3$H-LPS profile for each gradient, the amount of radioactivity in the body of the gradient; i.e., not bound to the HDL which floats at the gradient, was calculated as a percentage of the radioactivity recovered in the entire gradient. A logarithmic of this percentage as a function of the time of removal of the aliquot from the LPS serum reaction mixture yielded the half time for the binding of LPS to HDL.

C. Reconstitution Assay for LBP Activity

The basic method used during development of the purification procedure for LBP was a reconstitution assay in which fractions of acute phase serum were assayed for their ability to reconstitute "acute phase behavior" in NRS. The screening assay used was to mix a sample of the material to be tested with 1.0 ml of NRS at 37 degrees C. for 30 minutes. LPS and EDTA were then added to the concentrations given above, and the LPS-HDL binding reaction was allowed to proceed for ten minutes at 37 degrees before addition of CsCl and centrifugation. The 10 minute reaction time was chosen as a compromise between the times required for LPS to bind to HDL in NRS and APRS. Observation of a peak of $^3$H-LPS at a density of 1.30 g/cm$^3$ signalled the presence of LBP activity; i.e., complex 1.3 (C1.3) formed.

To quantitate LBP activity in purified fractions of APRS, the reconstitution assay just described was performed with a series of different amounts of the sample being assayed up to a maximum of 200 ul per ml NRS. After centrifugation and quantitation of the LPS in C1.3, a plot of percent LPS as C1.3 versus sample volume was made. One LBP unit is defined as that amount of LBP activity that causes 50% of the recovered LPS to be recovered as C1.3 in the above procedure. LBP activity in APRS was assayed similarly, except that the final volume of the NRS-APRS mixture was held constant and the final plot was then (percent LPS as C1.3) versus (percent APRS). On ocassion, to conserve materials, the total assay volume was reduced to 0.5 or 0.25 ml with proportional reduction of all components.

D. Purification of LPB

Two chromatographic procedures comprise the purification procedure for LBP. Serum was first fractionated using Bio-Rex 70 resin (Bio-Rad, Richmond, Calif.). Fifty milliliters of resin were equilibrated with 41 mM NaCl in 50 mM phosphate buffer, pH 7.3, containing 2 mM EDTA (phosphate/EDTA). Four hundred milliliters of APRS, containing 5 mM EDTA, was run over the column at approximately 65 ml/hour. The column was then washed with column equilibration buffer overnight (about 18 hours) or until the absorbance at 280 nm of the eluate was less than 0.2 absorbance units (AU). Washing was continued with 220 mM NaCl in phosphate/EDTA again until the absorbance was below 0.2, followed by a linear gradient formed from 60 ml each of 220 mM and 500 mM NaCl in phosphate/EDTA. Finally, the column was washed with 1M NaCl in phosphate/EDTA. Pools of fractions to be assayed for LBP activity were dialysed against 5 mM HEPES, pH 7.3, concentrated to 6 ml using PTGC (millipore, Bedford, Mass.) or YM10 (Amicon, Danvers, Mass.) membranes in an Amicon ultrafiltration cell, and any precipitate formed was removed by centrifugation.

The second chromatographic step used high performance liquid chromatography (HPLC) (Perkin-Elmer) with a Mono-Q column (Pharmacia, Piscataway, N.J.) as the adsorbent using the instructions provided with the pre- packed column. Unless otherwise noted, the flow rate was 1 ml per minute. The column was equilibrated with 20 mM diethanolamine buffer, pH 8.3. Injection of the sample was followed immediately by a 15 ml gradient of zero to 50 mM ammonium sulfate in 20 mM diethanolamine, pH 8.3. The gradient was then steepened, going in 15 minutes from 50 mM to 333 mM ammonium sulfate in the same buffer. Finally the column was washed for 5 minutes at a flow rate of 2 ml/min with 333 mM ammonium sulfate, again in 20 mM diethanolamine, pH 8.3. Fractions were collected and, on the basis of the absorbance profile of the column eluate, pooled into three pools, dialysed against 5 mM HEPES buffer, pH 7.4, and concentrated to 2 ml.

Final separation of the last two components of the LBP-containing fractions from Mono-Q chromatography was accomplished by SDS-PAGE using a 10 percent acrylamide gel. Following electrophoresis and light staining with Coomassie Blue the protein bands were cut apart and recovered from the gel by electroelution. Hunkapiller et al. *Meths. Enzymol.* 91:227 (1983).

Amino acid sequencing was carried out by the Protein Structure Core Laboratory of Scripps Research Foundation according to published procedures. Hewick et al., *J. Biol. Chem.* 256:7990 (1981).

E. Cloning and expression for human and rabbit LBP a) Libraries

The recombinant DNA studies discussed hereinafter were undertaken in collaboration with Dr. Ralf Schumann of the inventors' laboratory and Dr. Patrick Gray of Genentech, Inc.

The human library was obtained from liver biopsies from five trauma patients. The rabbit liver library was obtained from animals 24 hours after silver nitrate induction. RNA was extracted using the guanidine-hydrochloride method. Poly-A+m-RVA was enriched using oligo (dT)-columns. C-DNA was obtained with a c-DNA synthesis kit (Amersham), using reverse transcription for first strand synthesis. *E. coli* ribonuclease H, *E. coli* DNA polymerase 1 and T$^4$ DNA were used for second strand synthesis. C-DNA was labelled with $^{32}$P, gel-purified and linked and packaged with the Stratagene packaging system into GT-10-phage (Stratagene). This procedure yielded 1.2×10$^6$ PFUs.

b) Screening

Human and rabbit libraries were transferred to nitrocellulose and screened with a synthetic 5-prime probe based on the N-terminal sequence obtained from rabbit LPB. The human library was screened twice. Hybridizing phages were grown up and selected for those containing the largest inserts by cutting with a linker-specific restriction enzyme. The obtained DNA were gel-purified and subcloned into pUC 119 by transforming competent 294 cells with pUC 119, and ligated to the cut insert.

The rabbit library was also screened with a probe designed by cutting the human c-DNA with Eco RV and gel purifying the 3-prime end. After screening twice, 8 PFUs which hybridize with both probes were grown up. PFUs containing the largest inserts were grown up further and subcloned into pUC 119.

c) Subcloning and Sequencing:

The whole insert was digested with different restriction enzymes and subclones into M13 vector by transfecting competent SR101 cells. Sequencing was performed using the modified Sanger T7 method in part by sequencing the single stranded M13 material and in part by sequencing the PUC 119 fragment, using a series of synthesis primers.

The human gene was digested with Bam HI and Hind III in order to cut off untranslated regions. Missing 150 bp 5-prime bases were reconstituted with three 50-mer synthetic oligonucleotides. The religated gene was cloned into a pBR 322 expression vector, containing the trp-promotor. Competent 294 cells were transfected, mini-screened and grown up. Intracelluar LBP production was screened in cell lystates of (a) the transfected competent 294 cells, (b) a mock-transfected control and (c) a pBR control by SDS-PAGE with Coomassie blue staining and western-blot analyses using rabbit-anti-human LBP antibodies, goat anti-rabbit antisera and horseradish peroxide following usual procedures.

The rabbit gene was ligated into pRK5, an expression vector for mammalian cells, containing a sp-6 promotor. The vector was screened and grown up for transfection into a human kidney cell line which was grown to 30% confluency. One-half of these cells were radiolabelled with $^{35}$S-methionine. LBP production was screened in cell supernates and cell lysates by immunoprecipitation with goat-anti-rabbit LBP antiserum and protein A-sepharose. Results were compared to those of mock-transfected cells and cells transfected with pRK5, containing the LBP-gene in the opposite orientation (antisense). Unlabelled whole cells were screened using goat-anti-rabbit antiserum LBP and a rabbit-anti-goat FITC labelled antibody using a fluorescence-activated cell sorter (FACS).

F. Microtiter Binding Assay

Microtiter plates were coated with LPS by incubating 100 ul/well of 30 ug/ml Re595 LPS in 0.1M $Na_2Co_3$, 20 mM EDTA, pH 9.6 for 3 hours at 37°. The LPS solution was flicked out, the plates rinsed thoroughly under running water and air dried overnight. The binding properties of the dried, LPS-coated plates remain unchanged for up to eight weeks. Excess binding sites were then blocked with 200 ul/well of 10 mg/ml BSA in 50 mM HEPES, 0.15M NaCl, pH 7.4 (HS buffer) for 30 minutes at 37° temperature with agitation, after which the BSA solution was flicked out.

LBP samples, APRS, or NRS were added in a total volume of 100 ul/well diluted in 1 mg/ml BSA in HS buffer. Binding of LBP was allowed to occur for 3 hours at 37°. The plate was then rinsed 3 times with 200 ul/well of 1 mg/ml BSA in HS buffer with agitation over a 10 minute interval.

Goat anti-LBP serum, 100 ul/well, diluted 2000 times in 1 mg/ml BSA in HS buffer was then incubated in the wells for 2 hours at 37°. The anti-LBP antiserum was then rinsed out as above and replaced for 1 hour at room temperature with 100 ul/well of peroxidase conjugated rabbit anti-goat IgG diluted 2500 times in 1 mg/ml BSA.

Finally, 100 ul/well o-phenylenediamine solution (4 mM o-phenylenediamine, 2.3 mM $H_2O_2$, 50 mM citric acid, 133 mM $Na_2HPO_4$, pH 5.0) were added and the resulting composition maintained until sufficient color had developed (5–15 minutes). The reaction was stopped by addition of 100 ul/well 5M $H_2SO_4$ and the absorbance at 490 nm of each well was quantitated in a microtiter plate reader. Mean absorbances and standard errors of the means were calculated from 4–8 replicates of each well.

Inhibition of LBP binding to the plate was studied by premixing the compound under study at the desired concentration with 1 ug/ml purified LBP for 10 minutes at 37° before adding the mixture to the microtiter plate.

Significant differences were found in the utility of different brands of microtiter plates for these studies. Most brands avidly bound LBP, but not LBP-LPS complexes, without any LPS bound to the plate. In one set of studies, polymixin B at 10 ug/ml with 1 mg/ml BSA in HS buffer was incubated in the LPS coated, BSA blocked wells for 30 minutes at room temperature. Before addition of LBP to the wells the polymixin B solution was removed.

The present invention has been described with respect to preferred embodiments. It will be clear to those skilled in the art that modifications and/or variations of the disclosed subject matter can be made without departing from the scope of the invention set forth herein.

SUMMARY OF SEQUENCES

Sequence ID No. 1 is the nucleic acid sequence and the deduced amino acid sequence of a DNA fragment encoding a human LBP of the present invention.

Sequence ID No. 2 is the deduced amino acid sequence of a human LBP of the present invention.

What is claimed is:

1. A method of detecting lipopolysaccharide binding protein (LBP) in a mammalian sample comprising:
   a) contacting the sample with an LBP binding ligand under conditions sufficient to allow an LBP:ligand complex to form; and
   b) detecting the LBP; ligand complex.

2. The method of claim 1, wherein the LBP binding ligand is lipopolysaccharide (LPS).

3. The method of claim 1, wherein the LBP binding ligand is an antibody which binds LBP.

4. The method of claim 3, wherein the antibody is polyclonal.

5. The method of claim 3, wherein the antibody is monoclonal.

6. The method of claim 1, wherein the LBP is human.

7. The method of claim 6, wherein the LBP comprises the polypeptide of FIG. 19.

8. The method of claim 1, wherein the LBP is lapine.

9. The method of claim 8, wherein the LBP comprises the polypeptide of FIG. 17.

10. The method of claim 1, wherein the detecting is in vitro.

11. The method of claim 1, wherein the detecting is in vivo.

12. The method of claim 1, wherein the ligand is detectably labelled.

13. The method of claim 12, wherein the detectable label is selected from the group consisting of enzymes, radioisotopes, fluorescent compounds, colloidal metals, chemiluminescent compounds, phosphorescent compounds, and bioluminescent compounds.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1801 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: M-35533

( i x ) FEATURE:
        ( A ) NAME/KEY: CDS
        ( B ) LOCATION: 1..1431

( x i ) SEQUENCE DESCRIPTION: SEQ ID NO:1:

| | | | | | | | | | | | | | | | | |
|---|---|---|---|---|---|---|---|---|---|---|---|---|---|---|---|---|
| ATG | GGG | GCC | TTG | GCA | AGA | GCC | CTG | CCG | TCC | ATA | CTG | CTG | GCA | TTG | CTG | 48 |
| Met | Gly | Ala | Leu | Ala | Arg | Ala | Leu | Pro | Ser | Ile | Leu | Leu | Ala | Leu | Leu | |
| 1 | | | | 5 | | | | | 10 | | | | | 15 | | |
| CTT | ACG | TCC | ACC | CCA | GAG | GCT | CTG | GGT | GCC | AAC | CCC | GGC | TTG | GTC | GCC | 96 |
| Leu | Thr | Ser | Thr | Pro | Glu | Ala | Leu | Gly | Ala | Asn | Pro | Gly | Leu | Val | Ala | |
| | | | 20 | | | | | 25 | | | | | 30 | | | |
| AGG | ATC | ACC | GAC | AAG | GGA | CTG | CAG | TAT | GCG | GCC | CAG | GAG | GGG | CTA | TTG | 144 |
| Arg | Ile | Thr | Asp | Lys | Gly | Leu | Gln | Tyr | Ala | Ala | Gln | Glu | Gly | Leu | Leu | |
| | | 35 | | | | | 40 | | | | | 45 | | | | |
| GCT | CTG | CAG | AGT | GAG | CTG | CTC | AGG | ATC | ACG | CTG | CCT | GAC | TTC | ACC | GGG | 192 |
| Ala | Leu | Gln | Ser | Glu | Leu | Leu | Arg | Ile | Thr | Leu | Pro | Asp | Phe | Thr | Gly | |
| | 50 | | | | | 55 | | | | | 60 | | | | | |
| GAC | TTG | AGG | ATC | CCC | CAC | GTC | GGC | CGT | GGG | CGC | TAT | GAG | TTC | CAC | AGC | 240 |
| Asp | Leu | Arg | Ile | Pro | His | Val | Gly | Arg | Gly | Arg | Tyr | Glu | Phe | His | Ser | |
| 65 | | | | | 70 | | | | | 75 | | | | | 80 | |
| CTG | AAC | ATC | CAC | AGC | TGT | GAG | CTG | CTT | CAC | TCT | GCG | CTG | AGG | CCT | GTC | 288 |
| Leu | Asn | Ile | His | Ser | Cys | Glu | Leu | Leu | His | Ser | Ala | Leu | Arg | Pro | Val | |
| | | | | 85 | | | | | 90 | | | | | 95 | | |
| CCC | GGC | CAG | GGC | CTG | AGT | CTC | AGC | ATC | TCC | GAC | TCC | TCC | ATC | CGG | GTC | 336 |
| Pro | Gly | Gln | Gly | Leu | Ser | Leu | Ser | Ile | Ser | Asp | Ser | Ser | Ile | Arg | Val | |
| | | | 100 | | | | | 105 | | | | | 110 | | | |
| CAG | GGC | AGG | TGG | AAG | GTG | CGC | AAG | TCA | TTC | TTC | AAA | CTA | CAG | GGC | TCC | 384 |
| Gln | Gly | Arg | Trp | Lys | Val | Arg | Lys | Ser | Phe | Phe | Lys | Leu | Gln | Gly | Ser | |
| | | 115 | | | | | 120 | | | | | 125 | | | | |
| TTT | GAT | GTC | AGT | GTC | AAG | GGC | ATC | AGC | ATT | TCG | GTC | AAC | CTC | CTG | TTG | 432 |
| Phe | Asp | Val | Ser | Val | Lys | Gly | Ile | Ser | Ile | Ser | Val | Asn | Leu | Leu | Leu | |
| | 130 | | | | | 135 | | | | | 140 | | | | | |
| GGC | AGC | GAG | TCC | TCC | GGG | AGG | CCC | ACA | GGT | TAC | TGC | CTC | AGC | TGC | AGC | 480 |
| Gly | Ser | Glu | Ser | Ser | Gly | Arg | Pro | Thr | Gly | Tyr | Cys | Leu | Ser | Cys | Ser | |
| 145 | | | | | 150 | | | | | 155 | | | | | 160 | |
| AGT | GAC | ATC | GCT | GAC | GTG | GAG | GTG | GAC | ATG | TCG | GGA | GAT | TCG | GGG | TGG | 528 |
| Ser | Asp | Ile | Ala | Asp | Val | Glu | Val | Asp | Met | Ser | Gly | Asp | Ser | Gly | Trp | |
| | | | | 165 | | | | | 170 | | | | | 175 | | |
| CTC | TTG | AAC | CTC | TTC | CAC | AAC | CAG | ATT | GAG | TCC | AAG | TTC | CAG | AAA | GTA | 576 |
| Leu | Leu | Asn | Leu | Phe | His | Asn | Gln | Ile | Glu | Ser | Lys | Phe | Gln | Lys | Val | |
| | | | 180 | | | | | 185 | | | | | 190 | | | |
| CTG | GAG | AGC | AGG | ATT | TGC | GAA | ATG | ATC | CAG | AAA | TCA | GTG | TCC | TCC | GAT | 624 |
| Leu | Glu | Ser | Arg | Ile | Cys | Glu | Met | Ile | Gln | Lys | Ser | Val | Ser | Ser | Asp | |
| | | 195 | | | | | 200 | | | | | 205 | | | | |
| CTA | CAG | CCT | TAT | CTC | CAA | ACT | CTG | CCA | GTT | ACA | ACA | GAG | ATT | GAC | AGT | 672 |
| Leu | Gln | Pro | Tyr | Leu | Gln | Thr | Leu | Pro | Val | Thr | Thr | Glu | Ile | Asp | Ser | |
| | 210 | | | | | 215 | | | | | 220 | | | | | |
| TTC | GCC | GAC | ATT | GAT | TAT | AGC | TTA | GTG | GAA | GCC | CCT | CGG | GCA | ACA | GCC | 720 |
| Phe | Ala | Asp | Ile | Asp | Tyr | Ser | Leu | Val | Glu | Ala | Pro | Arg | Ala | Thr | Ala | |
| 225 | | | | | 230 | | | | | 235 | | | | | 240 | |
| CAG | ATG | CTG | GAG | GTG | ATG | TTT | AAG | GGT | GAA | ATC | TTT | CAT | CGT | AAC | CAC | 768 |
| Gln | Met | Leu | Glu | Val | Met | Phe | Lys | Gly | Glu | Ile | Phe | His | Arg | Asn | His | |
| | | | | 245 | | | | | 250 | | | | | 255 | | |
| CGT | TCT | CCA | GTT | ACC | CTC | CTT | GCT | GCA | GTC | ATG | AGC | CTT | CCT | GAG | GAA | 816 |
| Arg | Ser | Pro | Val | Thr | Leu | Leu | Ala | Ala | Val | Met | Ser | Leu | Pro | Glu | Glu | |
| | | | 260 | | | | | 265 | | | | | 270 | | | |
| CAC | AAC | AAA | ATG | GTC | TAC | TTT | GCC | ATC | TCG | GAT | TAT | GTC | TTC | AAC | ACG | 864 |
| His | Asn | Lys | Met | Val | Tyr | Phe | Ala | Ile | Ser | Asp | Tyr | Val | Phe | Asn | Thr | |
| | | 275 | | | | | 280 | | | | | 285 | | | | |
| GCC | AGC | CTG | GTT | TAT | CAT | GAG | GAA | GGA | TAT | CTG | AAC | TTC | TCC | ATC | ACA | 912 |
| Ala | Ser | Leu | Val | Tyr | His | Glu | Glu | Gly | Tyr | Leu | Asn | Phe | Ser | Ile | Thr | |
| | 290 | | | | | 295 | | | | | 300 | | | | | |
| GAT | GAC | ATG | ATA | CCG | CCT | GAC | TCT | AAT | ATC | CGA | CTG | ACC | ACC | AAG | TCC | 960 |
| Asp | Asp | Met | Ile | Pro | Pro | Asp | Ser | Asn | Ile | Arg | Leu | Thr | Thr | Lys | Ser | |
| 305 | | | | | 310 | | | | | 315 | | | | | 320 | |

| | | | | | | | | | | | | | | | | |
|---|---|---|---|---|---|---|---|---|---|---|---|---|---|---|---|---|
| TTC | CGA | CCC | TTC | GTC | CCA | CGG | TTA | GCC | AGG | CTC | TAC | CCC | AAC | ATG | AAC | 1008 |
| Phe | Arg | Pro | Phe | Val | Pro | Arg | Leu | Ala | Arg | Leu | Tyr | Pro | Asn | Met | Asn | |
| | | | | 325 | | | | 330 | | | | | | 335 | | |
| CTG | GAA | CTC | CAG | GGA | TCA | GTG | CCC | TCT | GCT | CCG | CTC | CTG | AAC | TTC | AGC | 1056 |
| Leu | Glu | Leu | Gln | Gly | Ser | Val | Pro | Ser | Ala | Pro | Leu | Leu | Asn | Phe | Ser | |
| | | | 340 | | | | | 345 | | | | | 350 | | | |
| CCT | GGG | AAT | CTG | TCT | GTG | GAC | CCC | TAT | ATG | GAG | ATA | GAT | GCC | TTT | GTG | 1104 |
| Pro | Gly | Asn | Leu | Ser | Val | Asp | Pro | Tyr | Met | Glu | Ile | Asp | Ala | Phe | Val | |
| | | 355 | | | | | 360 | | | | | 365 | | | | |
| CTC | CTG | CCC | AGC | TCC | AGC | AAG | GAG | CCT | GTC | TTC | CGG | CTC | AGT | GTG | GCC | 1152 |
| Leu | Leu | Pro | Ser | Ser | Ser | Lys | Glu | Pro | Val | Phe | Arg | Leu | Ser | Val | Ala | |
| | 370 | | | | | 375 | | | | | 380 | | | | | |
| ACT | AAT | GTG | TCC | GCC | ACC | TTG | ACC | TTC | AAT | ACC | AGC | AAG | ATC | ACT | GGG | 1200 |
| Thr | Asn | Val | Ser | Ala | Thr | Leu | Thr | Phe | Asn | Thr | Ser | Lys | Ile | Thr | Gly | |
| 385 | | | | | 390 | | | | | 395 | | | | | 400 | |
| TTC | CTG | AAG | CCA | GGA | AAG | GTA | AAA | GTG | GAA | CTG | AAA | GAA | TCC | AAA | GTT | 1248 |
| Phe | Leu | Lys | Pro | Gly | Lys | Val | Lys | Val | Glu | Leu | Lys | Glu | Ser | Lys | Val | |
| | | | | 405 | | | | | 410 | | | | | 415 | | |
| GGA | CTA | TTC | AAT | GCA | GAG | CTG | TTG | GAA | GCG | CTC | CTC | AAC | TAT | TAC | ATC | 1296 |
| Gly | Leu | Phe | Asn | Ala | Glu | Leu | Leu | Glu | Ala | Leu | Leu | Asn | Tyr | Tyr | Ile | |
| | | | 420 | | | | | 425 | | | | | 430 | | | |
| CTT | AAC | ACC | CTC | TAC | CCC | AAG | TTC | AAT | GAT | AAG | TTG | GCC | GAA | GGC | TTC | 1344 |
| Leu | Asn | Thr | Leu | Tyr | Pro | Lys | Phe | Asn | Asp | Lys | Leu | Ala | Glu | Gly | Phe | |
| | | 435 | | | | | 440 | | | | | 445 | | | | |
| CCC | CTT | CCT | CTG | CTG | AAG | CGT | GTT | CAG | CTC | TAC | GAC | CTT | GGG | CTG | CAG | 1392 |
| Pro | Leu | Pro | Leu | Leu | Lys | Arg | Val | Gln | Leu | Tyr | Asp | Leu | Gly | Leu | Gln | |
| | 450 | | | | | 455 | | | | | 460 | | | | | |
| ATC | CAT | AAG | GAC | TTC | CTG | TTC | TTG | GGT | GCC | AAT | GTC | CAA | TACATGAGAG | | | 1441 |
| Ile | His | Lys | Asp | Phe | Leu | Phe | Leu | Gly | Ala | Asn | Val | Gln | | | | |
| 465 | | | | | 470 | | | | | 475 | | | | | | |
| TTTGAGGACA | AGAAAGATGA | AGCTTGGAGG | TCACAGGCTG | GATCTGCTTG | TTGCATTTCC | 1501 |
| AGCTGTGCAG | CACGTCTCAG | AGATTCTTGA | AGAATGAAGA | CATTTCTGCT | CTCAGCTCCG | 1561 |
| GGGGTGAGGT | GTGCCTGGCC | TCTGCCTCCA | CCCTCCTCCT | CTTCACCAGG | TGCATGCATG | 1621 |
| CCCTCTCTGA | GTCTGGACTT | TGCTTCCCCT | CCAGGAGGGA | CCACCCTCCC | CGACTGGCCT | 1681 |
| GGGATATCTT | TACAAGCAGG | CACTGTATTT | TTTTATTCGC | CATCTGATCC | CCATGCCTAG | 1741 |
| CAGAGTGCTG | GCACTTAGTA | GGTCCTCAAT | AAATATTTAG | GTCGACGAGC | TCGAGAATTC | 1801 |

( 2 ) INFORMATION FOR SEQ ID NO:2:

( i ) SEQUENCE CHARACTERISTICS:
        ( A ) LENGTH: 477 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Gly | Ala | Leu | Ala | Arg | Ala | Leu | Pro | Ser | Ile | Leu | Leu | Ala | Leu | Leu |
| 1 | | | | 5 | | | | | 10 | | | | | 15 | |
| Leu | Thr | Ser | Thr | Pro | Glu | Ala | Leu | Gly | Ala | Asn | Pro | Gly | Leu | Val | Ala |
| | | | 20 | | | | | 25 | | | | | 30 | | |
| Arg | Ile | Thr | Asp | Lys | Gly | Leu | Gln | Tyr | Ala | Ala | Gln | Glu | Gly | Leu | Leu |
| | | 35 | | | | | 40 | | | | | 45 | | | |

```
Ala Leu Gln Ser Glu Leu Leu Arg Ile Thr Leu Pro Asp Phe Thr Gly
     50                  55                  60

Asp Leu Arg Ile Pro His Val Gly Arg Gly Arg Tyr Glu Phe His Ser
 65              70                  75                      80

Leu Asn Ile His Ser Cys Glu Leu Leu His Ser Ala Leu Arg Pro Val
                 85                  90                  95

Pro Gly Gln Gly Leu Ser Leu Ser Ile Ser Asp Ser Ser Ile Arg Val
             100                 105                 110

Gln Gly Arg Trp Lys Val Arg Lys Ser Phe Phe Lys Leu Gln Gly Ser
             115                 120                 125

Phe Asp Val Ser Val Lys Gly Ile Ser Ile Ser Val Asn Leu Leu Leu
     130                 135                 140

Gly Ser Glu Ser Ser Gly Arg Pro Thr Gly Tyr Cys Leu Ser Cys Ser
145                 150                 155                 160

Ser Asp Ile Ala Asp Val Glu Val Asp Met Ser Gly Asp Ser Gly Trp
                 165                 170                 175

Leu Leu Asn Leu Phe His Asn Gln Ile Glu Ser Lys Phe Gln Lys Val
             180                 185                 190

Leu Glu Ser Arg Ile Cys Glu Met Ile Gln Lys Ser Val Ser Ser Asp
         195                 200                 205

Leu Gln Pro Tyr Leu Gln Thr Leu Pro Val Thr Thr Glu Ile Asp Ser
     210                 215                 220

Phe Ala Asp Ile Asp Tyr Ser Leu Val Glu Ala Pro Arg Ala Thr Ala
225                 230                 235                 240

Gln Met Leu Glu Val Met Phe Lys Gly Glu Ile Phe His Arg Asn His
                 245                 250                 255

Arg Ser Pro Val Thr Leu Leu Ala Ala Val Met Ser Leu Pro Glu Glu
             260                 265                 270

His Asn Lys Met Val Tyr Phe Ala Ile Ser Asp Tyr Val Phe Asn Thr
         275                 280                 285

Ala Ser Leu Val Tyr His Glu Glu Gly Tyr Leu Asn Phe Ser Ile Thr
     290                 295                 300

Asp Asp Met Ile Pro Pro Asp Ser Asn Ile Arg Leu Thr Thr Lys Ser
305                 310                 315                 320

Phe Arg Pro Phe Val Pro Arg Leu Ala Arg Leu Tyr Pro Asn Met Asn
                 325                 330                 335

Leu Glu Leu Gln Gly Ser Val Pro Ser Ala Pro Leu Leu Asn Phe Ser
             340                 345                 350

Pro Gly Asn Leu Ser Val Asp Pro Tyr Met Glu Ile Asp Ala Phe Val
         355                 360                 365

Leu Leu Pro Ser Ser Ser Lys Glu Pro Val Phe Arg Leu Ser Val Ala
     370                 375                 380

Thr Asn Val Ser Ala Thr Leu Thr Phe Asn Thr Ser Lys Ile Thr Gly
385                 390                 395                 400

Phe Leu Lys Pro Gly Lys Val Lys Val Glu Leu Lys Glu Ser Lys Val
                 405                 410                 415

Gly Leu Phe Asn Ala Glu Leu Leu Glu Ala Leu Leu Asn Tyr Tyr Ile
             420                 425                 430

Leu Asn Thr Leu Tyr Pro Lys Phe Asn Asp Lys Leu Ala Glu Gly Phe
         435                 440                 445
```

-continued

| Pro | Leu | Pro | Leu | Leu | Lys | Arg | Val | Gln | Leu | Tyr | Asp | Leu | Gly | Leu | Gln |
|-----|-----|-----|-----|-----|-----|-----|-----|-----|-----|-----|-----|-----|-----|-----|-----|
|     | 450 |     |     |     | 455 |     |     |     |     | 460 |     |     |     |     |     |
| Ile | His | Lys | Asp | Phe | Leu | Phe | Leu | Gly | Ala | Asn | Val | Gln |
| 465 |     |     |     |     | 470 |     |     |     |     | 475 |     |     |